US009113912B1

United States Patent
Mehta et al.

(10) Patent No.: US 9,113,912 B1
(45) Date of Patent: Aug. 25, 2015

(54) SYSTEMS AND DEVICES TO IDENTIFY AND LIMIT NERVE CONDUCTION

(71) Applicants: Bankim H. Mehta, San Ramon, CA (US); Mark McCall, San Ramon, CA (US); Scott A. McGill, San Ramon, CA (US)

(72) Inventors: Bankim H. Mehta, San Ramon, CA (US); Mark McCall, San Ramon, CA (US); Scott A. McGill, San Ramon, CA (US)

(73) Assignee: Serene Medical, Inc., San Ramon, CA (US)

( * ) Notice: Subject to any disclaimer, the term of this patent is extended or adjusted under 35 U.S.C. 154(b) by 0 days.

(21) Appl. No.: 14/602,187

(22) Filed: Jan. 21, 2015

(51) Int. Cl.
*A61B 18/14* (2006.01)
*A61N 1/36* (2006.01)
*A61B 18/00* (2006.01)

(52) U.S. Cl.
CPC ........ *A61B 18/1492* (2013.01); *A61N 1/36017* (2013.01); *A61B 2018/00029* (2013.01); *A61B 2018/0047* (2013.01); *A61B 2018/00321* (2013.01); *A61B 2018/00434* (2013.01); *A61B 2018/00577* (2013.01); *A61B 2018/00642* (2013.01); *A61B 2018/00702* (2013.01); *A61B 2018/00839* (2013.01); *A61B 2018/00958* (2013.01)

(58) Field of Classification Search
CPC ............. A61B 2018/00434; A61B 2018/0044; A61B 2018/00446; A61N 1/0456; A61N 1/0502; A61N 1/0526
USPC .................. 606/28, 41; 607/99, 113, 115, 118
See application file for complete search history.

(56) References Cited

U.S. PATENT DOCUMENTS

| | | |
|---|---|---|
| 3,104,879 A | 9/1963 | Jetton |
| 4,306,111 A | 12/1981 | Lu et al. |
| 4,411,266 A | 10/1983 | Cosman |
| 4,674,499 A | 6/1987 | Pao |
| 4,896,671 A | 1/1990 | Cunningham et al. |
| 4,936,842 A | 6/1990 | D'Amelio et al. |
| 5,078,717 A | 1/1992 | Parins |
| 5,098,431 A | 3/1992 | Rydell |
| 5,122,137 A | 6/1992 | Lennox |
| 5,364,393 A | 11/1994 | Auth et al. |
| 5,397,339 A | 3/1995 | Desai |
| 5,403,311 A | 4/1995 | Abele et al. |
| 5,439,224 A | 8/1995 | Bertoncino |
| 5,450,846 A | 9/1995 | Goldreyer |
| 5,454,809 A | 10/1995 | Janssen |
| 5,458,597 A | 10/1995 | Edwards et al. |
| 5,540,681 A | 7/1996 | Strul et al. |

(Continued)

FOREIGN PATENT DOCUMENTS

| | | |
|---|---|---|
| WO | WO 99/48046 | 9/1999 |
| WO | WO 02/40111 | 5/2002 |

(Continued)

*Primary Examiner* — Michael Peffley
*Assistant Examiner* — Thomas Giuliani
(74) *Attorney, Agent, or Firm* — Levine Bagade Han LLP

(57) ABSTRACT

Methods and devices for improved precision in finding one or more nerves and then interrupting the transmission of neural signals through the target nerve. The treated nerve can be rendered incapable of transmitting neural signals for a select duration of time, where such a duration can be on a temporarily basis (e.g., hours, days or weeks) or a longer term/ permanent basis (e.g., months or years). One embodiment of the apparatus includes a precise energy source system which features energy transfer elements that are capable of creating areas of nerve destruction, inhibition and ablation with precision.

30 Claims, 38 Drawing Sheets

(56) References Cited

U.S. PATENT DOCUMENTS

| | | |
|---|---|---|
| 5,540,734 A | 7/1996 | Zabara |
| 5,674,191 A | 10/1997 | Edwards et al. |
| 5,697,536 A | 12/1997 | Eggers et al. |
| 5,697,882 A | 12/1997 | Eggers et al. |
| 5,697,909 A | 12/1997 | Eggers et al. |
| 5,749,914 A | 5/1998 | Janssen |
| 5,782,826 A | 7/1998 | Swanson |
| 5,843,019 A | 12/1998 | Eggers et al. |
| 5,895,386 A | 4/1999 | Odell et al. |
| 5,897,552 A | 4/1999 | Edwards et al. |
| 5,906,614 A | 5/1999 | Stern et al. |
| 5,971,983 A | 10/1999 | Lesh |
| 6,004,319 A | 12/1999 | Goble et al. |
| 6,016,452 A | 1/2000 | Kasevich |
| 6,023,638 A | 2/2000 | Swanson |
| 6,096,035 A | 8/2000 | Sodhi et al. |
| 6,099,524 A | 8/2000 | Lipson et al. |
| 6,102,907 A | 8/2000 | Smethers et al. |
| 6,122,549 A | 9/2000 | Sharkey et al. |
| 6,139,545 A | 10/2000 | Utley et al. |
| 6,146,380 A | 11/2000 | Racz et al. |
| 6,149,620 A | 11/2000 | Baker et al. |
| 6,149,647 A | 11/2000 | Tu et al. |
| 6,159,194 A | 12/2000 | Eggers et al. |
| 6,161,048 A | 12/2000 | Sluijter et al. |
| 6,165,169 A | 12/2000 | Panescu et al. |
| 6,165,173 A | 12/2000 | Kamdar et al. |
| 6,197,021 B1 | 3/2001 | Panescu et al. |
| 6,241,753 B1 | 6/2001 | Knowlton |
| 6,246,912 B1 | 6/2001 | Sluijter et al. |
| 6,259,945 B1 | 7/2001 | Epstein et al. |
| 6,259,952 B1 | 7/2001 | Sluijter et al. |
| 6,292,695 B1 | 9/2001 | Webster et al. |
| 6,312,428 B1 | 11/2001 | Eggers et al. |
| 6,337,994 B1 | 1/2002 | Stoianovici et al. |
| 6,379,349 B1 | 4/2002 | Mueller et al. |
| 6,381,498 B1 | 4/2002 | Knowlton |
| 6,384,384 B1 | 5/2002 | Conolly |
| 6,405,732 B1 | 6/2002 | Edwards et al. |
| 6,432,986 B2 | 8/2002 | Levin |
| 6,466,817 B1 | 10/2002 | Kaula et al. |
| 6,524,308 B1 | 2/2003 | Mueller et al. |
| 6,564,096 B2 | 5/2003 | Mest |
| 6,569,028 B1 | 5/2003 | Nichols |
| 6,575,969 B1 | 6/2003 | Rittman, III et al. |
| 6,618,626 B2 | 9/2003 | West, Jr. et al. |
| 6,663,627 B2 | 12/2003 | Francischelli et al. |
| 6,706,016 B2 | 3/2004 | Cory et al. |
| 6,719,754 B2 | 4/2004 | Underwood et al. |
| 6,735,475 B1 | 5/2004 | Whitehurst et al. |
| 6,740,084 B2 | 5/2004 | Ryan |
| 6,749,604 B1 | 6/2004 | Eggers et al. |
| 6,911,027 B1 | 6/2005 | Edwards et al. |
| 6,989,010 B2 | 1/2006 | Francischelli et al. |
| 7,115,124 B1 | 10/2006 | Xiao |
| 7,177,677 B2 | 2/2007 | Kaula et al. |
| 7,282,049 B2 | 10/2007 | OrszuJak et al. |
| 7,300,435 B2 | 11/2007 | Wham et al. |
| RE40,279 E | 4/2008 | Sluijter et al. |
| 8,512,715 B2 | 8/2013 | Papay |
| 8,521,295 B2 | 8/2013 | Laufer |
| 8,666,498 B2 | 3/2014 | Newman |
| 2002/0065481 A1 | 5/2002 | Cory et al. |
| 2002/0065567 A1 | 5/2002 | Kodera |
| 2002/0068930 A1 | 6/2002 | Tasto et al. |
| 2002/0120260 A1 | 8/2002 | Morris et al. |
| 2004/0059328 A1 | 3/2004 | Daniel et al. |
| 2005/0033137 A1 | 2/2005 | Oral et al. |
| 2005/0177211 A1 | 8/2005 | Leung et al. |
| 2005/0283148 A1 | 12/2005 | Janssen et al. |
| 2006/0089688 A1 | 4/2006 | Panescu |
| 2006/0153876 A1 | 7/2006 | Sanders |
| 2007/0060921 A1 | 3/2007 | Janssen et al. |
| 2007/0167943 A1 | 7/2007 | Janssen et al. |
| 2008/0051859 A1 | 2/2008 | Sharkey et al. |
| 2009/0062886 A1 | 3/2009 | O'Handley et al. |
| 2010/0114095 A1 | 5/2010 | Janssen et al. |
| 2010/0114191 A1 | 5/2010 | Newman |
| 2013/0046292 A1 | 2/2013 | Janssen et al. |
| 2014/0058372 A1* | 2/2014 | Belson .................... 606/32 |
| 2014/0303617 A1* | 10/2014 | Shimada .................... 606/41 |

FOREIGN PATENT DOCUMENTS

| | | |
|---|---|---|
| WO | WO 02/41240 | 5/2002 |
| WO | WO 03/068095 | 8/2003 |
| WO | WO 2008/011730 | 1/2008 |
| WO | WO 2008/014465 | 10/2008 |

* cited by examiner

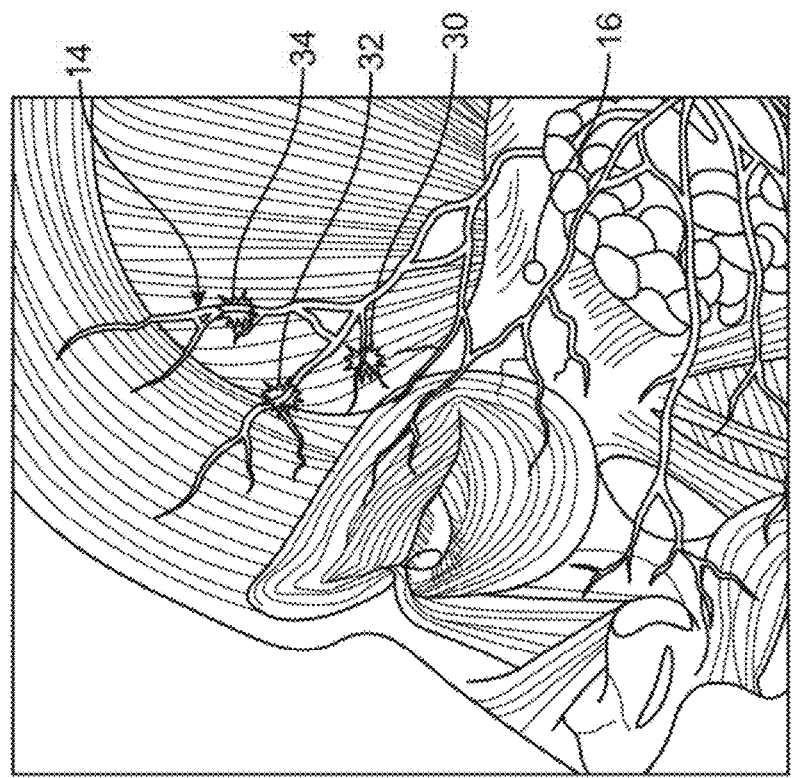
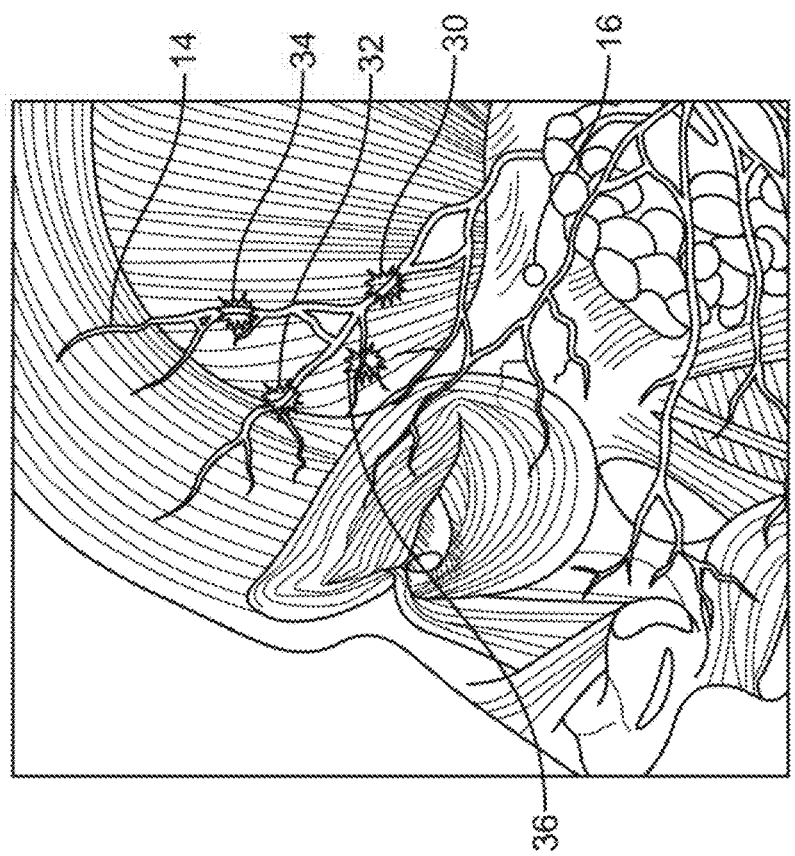
FIG. 6A
FIG. 6B

SYSTEMS AND DEVICES TO IDENTIFY AND LIMIT NERVE CONDUCTION

CROSS-REFERENCE TO RELATED APPLICATIONS n/a

BACKGROUND OF THE INVENTION

The present invention relates to methods and devices for improved precision in finding one or more nerves and then interrupting the transmission of neural signals through the target nerve. The treated nerve can be rendered incapable of transmitting neural signals for a select duration of time, where such a duration can be on a temporarily basis (e.g., hours, days or weeks) or a longer term/permanent basis (e.g., months or years). One embodiment of the apparatus includes a precise energy source system which features energy transfer elements that are capable of creating areas of nerve destruction, inhibition and ablation with precision.

The human nervous system sends and receives signals to convey both sensory information, such as pain, heat, cold and touch, as well as command signals that control muscle movement. There are many cases where disrupting the neural signal can provide preventative, therapeutic, and/or cosmetic benefits to an individual. For example, extraneous, undesired, or abnormal signals can be generated (or are transmitted) along nervous system pathways. For example, the pinching of a minor nerve in the back can cause extreme back pain. Similarly, the compression or other activation of certain nerves can induce significant or constant pain. Certain diseases also may compromise the lining of nerves such that neural signals spontaneously generate. This spontaneous generation can cause a variety of maladies, from seizures to pain or (in extreme conditions) even death. Abnormal signal activations can cause many other problems including (but not limited to) twitching, tics, seizures, distortions, cramps, disabilities (in addition to pain), other undesirable conditions, or other painful, abnormal, undesirable, socially or physically detrimental afflictions.

In some situations, the normal conduction of neural signals causes undesirable 4muscle causes frown lines that can result in permanent distortion of the brow (or forehead); giving the appearance of premature aging. Interrupting the neural signal of the corrugator supercilli activation nerves can alleviate the distortion of the brow or forehead.

Traditional electrosurgical procedures use either a unipolar or bipolar device connected to an energy source. A unipolar electrode system includes a small surface area electrode, and a return electrode placed in contact with the body at a location separate and spaced from the small surface area electrode. The return electrode is generally larger in size, and is either resistively or capacitively coupled to the body. Since the same amount of current must flow through each electrode to complete the circuit. Because the return electrode is typically a large surface area the decreased current density allows heat to be dissipated over the larger surface area. In some cases, it is desirable to locate return electrodes in areas of high blood flow (such as the biceps, buttocks or other muscular or highly vascularized area) so that any generated heat generated is rapidly carried dissipated. One advantage of a unipolar system is the ability to place the unipolar probe exactly where it is needed and optimally focus electrosurgical energy where desired. A resistive return electrode would typically be coated with a conductive paste or jelly. If the contact with the patient is reduced or if the jelly dries out, a high-current density area may result, increasing the probability for burns at the contact point.

Typical bipolar electrode systems are generally based upon a device having electrodes of opposite polarity. Each electrode is connected to one of the two poles of the electrosurgical generator. When the electrosurgical energy is applied, it is concentrated (and focused) so that current flows between the electrodes of opposite polarity in the region of the device. Assuming the instrument has been designed and used properly, the resulting current flow will be constrained within the target tissue between the two surfaces.

Treatments for the elimination of glabellar furrowing have included surgical forehead lifts, resection of corrugator supercilli muscle, as described by Guyuron, Michelow and Thomas in Corrugator Supercilli Muscle Resection Through Blepharoplastyincision, Plastic Reconstructive Surgery 95 691-696 (1995). Also, surgical division of the corrugator supercilli motor nerves is used and was described by Ellis and Bakala in Anatomy of the Motor innervation of the Corrugator Supercilli Muscle: Clinical Significance and Development of a New Surgical Technique for Frowning, J Otolaryngology 27; 222-227 (1998). These techniques described are highly invasive and sometimes temporary as nerves regenerate over time and repeat or alternative procedures are required.

Another less invasive procedure to treat glabellar furrowing involves injection of botulinum toxin (Botox) directly into the muscle. This produces a flaccid paralysis and is best described in The New England Journal of Medicine, 324: 1186-1194 (1991). While minimally invasive, this technique is predictably transient; so, it must be re-done every few months.

Specific efforts to use RF energy via a two needle bipolar system has been described by Hernandez-Zendejas and Guerrero-Santos in: Percutaneous Selective Radio-Frequency Neuroablation in Plastic Surgery, Aesthetic Plastic Surgery, 18:41 pp 41-48 (1994) The authors described a bipolar system using two parallel needle type electrodes. Utley and Goode described a similar system in Radio-frequency Ablation of the Nerve to the Corrugator Muscle for Elimination of Glabellar Furrowing, Archives of Facial Plastic Surgery, January-March, 99, VI P 46-48, and U.S. Pat. No. 6,139,545. These systems were apparently unable to produce permanent results possibly because of limitations inherent in a two needle bipolar configuration. Thus, as is the case with Botox, the parallel needle electrode systems would typically require periodic repeat procedures.

There are many ways of properly locating an active electrode near the target tissue and determining if it is in close proximity to the nerve such that the treatment is limited to the area of interest. In many applications, there is a need to ensure that the nerve is located and treated to establish a desired effect while minimizing collateral damage to surrounding tissues. Such is especially the case in cosmetic application.

Various stimulation devices have been made and patented. One process of stimulation and ablation using a two-needle system is disclosed in U.S. Pat. No. 6,139,545. The stimulation may also be implemented negatively, where tissue not responsive to stimulation is ablated as is described in U.S. Pat. No. 5,782,826 (issued Jul. 21, 1998).

SUMMARY OF THE INVENTION

The present invention relates to devices and methods for positioning a treatment device adjacent to a nerve, stimulating the nerve and then applying a therapeutic treatment to impair the nerve's ability to transmit a neural signal. In particular, the devices and methods can be used in a cosmetic application in the areas of the head and face. However, the devices and methods can be used in any part of the body.

The present disclosure includes methods of treating a nerve in a tissue region. One example of such a method comprises positioning a working end of a device into the tissue region; where the device includes a stimulation mode and a treatment mode, the stimulation mode comprises at least a first parameter setting that stimulates the nerve at a first distance from the working end, and a second parameter setting that stimulates the nerve at a second distance from the working end, where the first distance is greater than the second distance, and where the device is configured to prevent activation of the treatment mode when the stimulation mode is in the first parameter setting; activating the device in the stimulation mode at the first parameter setting to observe a stimulation of the nerve; repositioning the working end of the device in the tissue region to move the working end closer to the nerve; re-activating the device in the stimulation mode at the second parameter to observe stimulation of the nerve and confirm repositioning of the working end of the device closer to the nerve; and activating the device in the treatment mode to create a first treatment zone on the nerve at a pre-determined treatment setting, where activating the device in the treatment mode causes the device to reset to the first parameter setting.

The method can further include moving the working end in a direction relative to the nerve to create multiple treatment zones along the nerve. In certain variations, moving the working end of the device in the direction relative to the nerve comprises moving the working end of the device in a forward direction distally to a first treatment area along the nerve such that a muscle associated with the nerve can be stimulated during stimulation of the nerve.

Variations of the method include positioning the working end of the device and repositioning the working end of the device occurs without removing the device from the puncture site. Moving the device can include moving the device in a plurality of directions without removing the device from the tissue region to increase an area for observing stimulation of the nerve.

The method can also further comprise injecting an anesthetic at or near the first treatment zone prior to activating the device in the treatment mode.

The methods and devices can also include reducing a temperature of the surface of the skin above the treatment site prior to applying energy and keeping the ice in place during application of energy.

In an additional variation, the methods can further comprise the use of an external nerve stimulator to map the nerve anatomy on the skin, prior to inserting the device, and using the map as a guide to identify target treatment locations.

In certain variations the first parameter setting comprises a first current setting and the second parameter setting comprises a second current setting, where the second current setting is less than the first current setting. The first parameter setting can be fixed and/or the second parameter setting can be adjustable.

The method can also include activating the device in the stimulation mode at the first parameter setting to observe the stimulation of the nerve comprises observing movement of a surface of the tissue region. The method can also include activating the device in the stimulation mode at the first parameter setting to observe the stimulation of the nerve comprises performing electromyography on at least one muscle associated with the nerve. Additionally, activating the device in the stimulation mode at the first parameter setting to observe the stimulation of the nerve comprises measuring an electrical impulse in at least one muscle associated with the nerve using a measuring electrode In another example, the present disclosure includes a method of treating a nerve in a tissue region. In one variation the method includes positioning a device into the tissue region at a first location; applying energy to the tissue region through the device at the first location using a first setting configured to stimulate the nerve within a first distance from the working end of the device; observing for stimulation of the nerve; re-applying energy to the tissue region through the device at a second location using a second setting configured to stimulate the nerve within a second distance from the working end of the device, where the second distance is less than the first distance; re-assessing whether the nerve is stimulated at the second setting to determine if the second location is closer to the nerve than the first location; applying energy to the nerve to affect the ability of the nerve to transmit a neural signal using the device upon observing stimulation of the nerve using the second setting if the second location is closer to the nerve.

The method can include the device resetting to the first setting after applying energy to the nerve, the method further comprising re-adjusting the device to the second setting and subsequently re-applying energy to the tissue region through the device at a subsequent location using a second setting configured to stimulate the nerve within the second distance from the working end of the device.

The method can also moving the device in a direction relative to the nerve to create multiple treatment zones along the nerve. The moving of the device in the direction relative to the nerve can comprise moving the device in a forward direction distally to the first location along the nerve such that a muscle associated with the nerve can be stimulated during stimulation of the nerve. In additional variations positioning the device at the first location and the second location occurs without removing the device from the puncture site.

The method can further comprise moving the device in a plurality of directions without removing the device from the tissue region prior to re-applying energy at the second location. The method can also include injecting an anesthetic at or near the tissue region at the first location site prior to applying energy to the tissue region.

In another variation, a method can include positioning a working end of a device into the tissue region at a first location where the device is configured to apply stimulation energy and to apply therapeutic energy; wherein when supplying stimulation energy the device is settable in one of a plurality of settings, the plurality of settings comprising at least a first setting and a second setting, where a stimulation area of the device is larger when the device is operated at the first setting, and where the device is configured to prevent application of the therapeutic energy when the device is in the first setting; operating the device at the second setting; observing a response in the tissue region for stimulation of the nerve; applying therapeutic energy to at least a portion of the nerve to prevent the nerve from transmitting a neural signal by applying the therapeutic energy to the tissue region upon observing the response, wherein after applying therapeutic energy the device resets to the first setting; repositioning the working end of the device at a subsequent location; adjusting the device to the second setting from the first setting; observing a subsequent response in the tissue region for stimulation of the nerve; and applying therapeutic energy at least a second portion of the nerve at the subsequent location by applying therapeutic energy upon observing the subsequent response.

The method can include moving the device in a direction relative to the nerve to create multiple treatment zones along the nerve.

In another variation, the method of treating a nerve can include inserting a single longitudinal probe into a tissue region, where the probe includes a threshold stimulation current setting where the probe is prevented from applying therapeutic energy at or above the threshold stimulation current setting; directing the probe tip towards the nerve; delivering a stimulating current through the probe to trigger movement of a muscle associated with the nerve; reducing a stimulating current setting below the threshold stimulation current setting such that a stimulation area of the probe decreases; moving the probe in the tissue region towards the nerve; stimulating the nerve to trigger movement of the muscle and confirm that the location of the nerve is within the decreased stimulation area of the probe; applying an electrical current to heat the nerve upon observing the movement of the muscle, wherein after applying electrical current the stimulation current setting is reset above the threshold stimulation current.

The present disclosure also includes a system for treating a nerve in a region of tissue, the system comprising: a probe having a working end for positioning within tissue;

a controller configured to provide power to the probe in a therapeutic mode and a stimulation mode; where the controller is further configured to be adjustable between a plurality of stimulation settings, the plurality of stimulation settings comprising at least a first stimulation setting and a second stimulation setting and where the controller is further configured to prevent application of power in the therapeutic mode when unless set to the second stimulation setting; where an effective stimulation area of the probe is reduced in the second stimulation setting as compared to the effective stimulation area of the probe in the first stimulation setting such that the working end of the probe must be closer to the nerve in the second stimulation setting than in the first stimulation setting to stimulate the nerve; and where the controller is further configured to reset to the first stimulation setting after application of power in the therapeutic mode.

The system can include an anesthetic supply fluidly coupled to an opening on the working end of the probe. In some variations, the first stimulation setting is fixed. Alternatively, or in combination the second stimulating setting can be adjustable.

The system can include an energy transfer section on the working end, where the energy transfer section comprises at least a first conductive portion and a second conductive portion longitudinally spaced on the probe, the first and the second conductive portions separated by an electrically insulative material.

Variations of the system can include a fluid port located on the working end and between the first conductive portion and the second conductive portion.

In some variations, a temperature sensing element is located between the first conductive portion and the second conductive portion.

The system can also include an illumination source on the working end. The illumination source can comprises a modulation flash rate proportional to the amount of stimulation energy.

The device can also include a lumen operatively disposed along the length of the single axis probe.

The present disclosure also includes electrosurgical devices for use with a source of stimulation energy and a source of therapeutic energy to simulate and treat tissue under skin and for use with a reservoir having a flowable substance. For example, the device can include a device body; a probe extending from a portion of the device body, the probe being rigid such that manipulation of the device body permits movement of the probe within tissue; a distal electrode located at a working end of the probe; a proximal electrode positioned on the probe and spaced proximally from the distal electrode, where the distal and proximal electrodes are coupleable to the source of stimulation energy and the source of therapeutic energy, where application of the therapeutic energy to the distal electrode and proximal electrode forms a lesion in a tissue region spanning between the proximal and distal electrodes; a fluid dispensing sleeve having one or more fluid ports, the fluid dispensing sleeve positioned between the distal electrode and proximal electrode where at least one of the fluid ports is oriented to deliver the flowable substance in an orthogonal direction to an axis of the probe such that the flowable substance is directed to the tissue region.

The device can also include a fluid dispensing lumen that delivers the flowable substance in an axial direction out the tip of the probe into the tissue.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

The foregoing and other objects, features and advantages of the methods, devices, and systems described herein will become apparent from the following description in conjunction with the accompanying drawings, in which reference characters refer to the same parts throughout the different views. The drawings are not necessarily to scale; emphasis has instead been placed upon illustrating the principles of the invention.

FIGS. 6A and 6B illustrate various additional examples of creating treatment sites to effect a therapeutic benefit.

DETAILED DESCRIPTION OF THE INVENTION

The following illustrations are examples of the methods and devices included in the invention described herein. It is contemplated that combinations of aspects of specific embodiments or combinations of the specific embodiments themselves are within the scope of this disclosure. While the methods, devices, and systems described herein are discussed as being used in to treat nerves, especially for cosmetic purposes, the devices, methods, and systems of the present disclosure can be can be used in other parts of the body where accurate ablation or application of energy is desired.

The present disclosure is related to commonly assigned application Ser. No. 10/870,202, filed Jun. 17, 2004, publication No. US-2005-0283148-A1; Ser. No. 11/460,870, filed Jul. 28, 2006, publication No. US-2007-0060921-A1; Ser. No. 14/594,935, filed Jan. 12, 2015; Ser. No. 11/559,232, filed Nov. 13, 2006, publication No. US-2007-0167943-A1; Ser. No. 12/612,360, filed Nov. 4, 2009, publication No. US-2010-0114095-A1; Ser. No. 13/570,138, filed Aug. 8, 2012, publication No. US-2013-0046292-A1; Ser. No. 12/605,295, filed Oct. 23, 2009, publication No. US-2010-0114191-A1, now U.S. Pat. No. 8,666,498; Ser. No. 14/156,033, filed Jan. 15, 2014, publication No. US-2014-0180360-A1, now U.S. Pat. No. 8,938,302; and Ser. No. 14/599,161, filed Jan. 16, 2015, the entirety of each of which is incorporated by reference.

Figure 1:
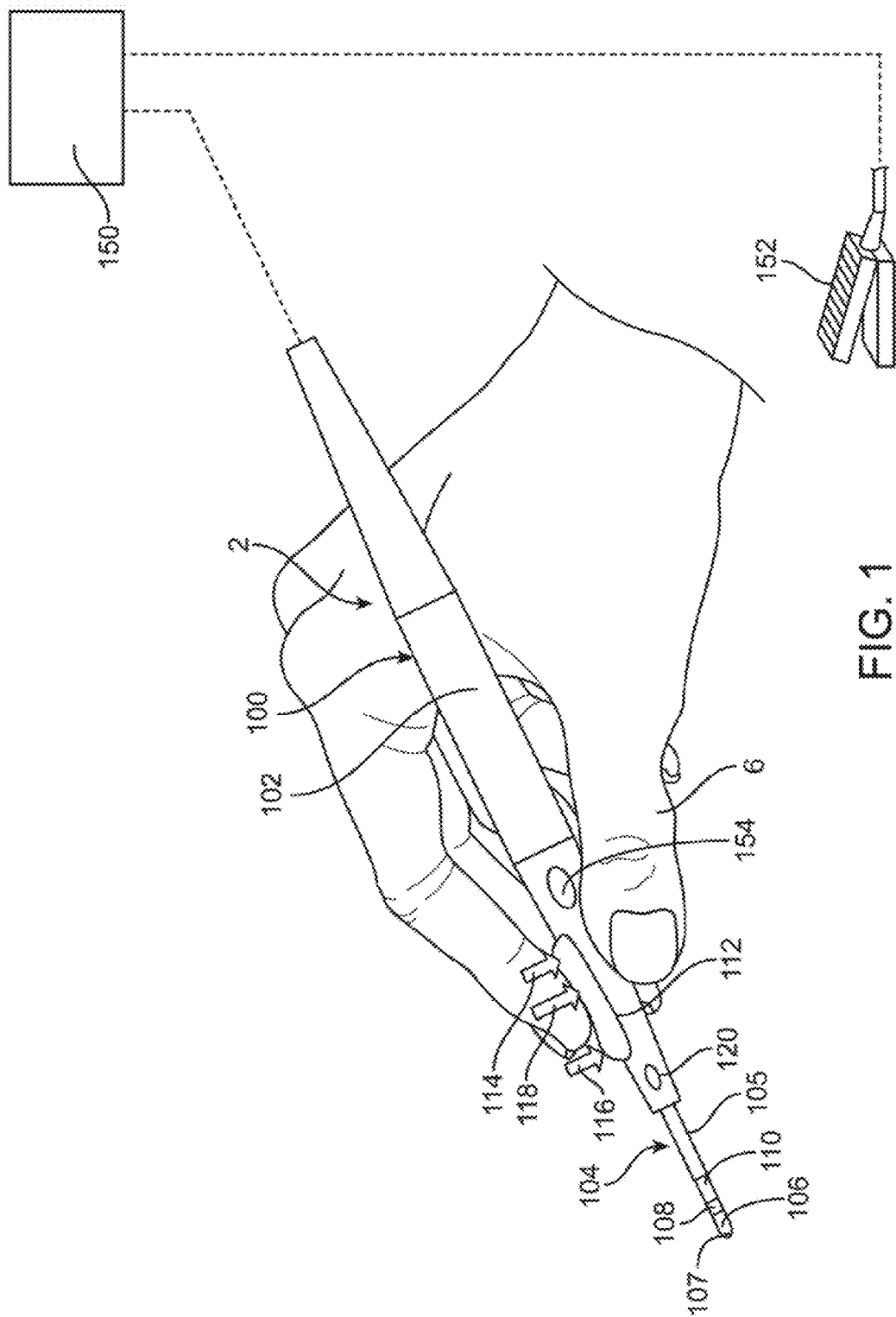
FIG. 1 illustrates an example of a device configured for stimulation and treatment of nerves.

FIG. 1 illustrates one example of a device 100 configured to locate and treat a nerve. As described below, the device 100 is part of a system that can identify a nerve and also deliver energy to interfere with the nerve's ability to transmit signals. In many cases the energy will have a thermal effect on the nerve. However, any treatment modality can be used to disrupt the ability of the nerve to transmit a neural signal. As illustrated, a variation of the device 100 includes a device body 102 that can optionally be ergonomically designed so that a physician can grip the device 100 and position the device 100 and/or working end 104 accordingly using fine motor skills. Typically, such placement can be achieved by balancing the device body 102 in a hand 2 or a web of the hand 2 between a forefinger 4 and thumb 6. However, the devices and methods described herein can include any number of configurations that allow for positioning. In addition, variations of the device allow for positioning using automated machinery such as robotic manipulators and/or positioners. Variations of the device 100 can include features to permit left or right handed operation. Alternatively, the device body 102 can be symmetrical allowing for left or right handed operation.

FIG. 1 also illustrates a switch 112 that is located on the device body 102 and permits the physician to easily and safely initiate the delivery of energy in either a stimulation mode or a therapeutic mode. Again, variations of the device can include a switch that is external from the device body 102 e.g., a foot pedal, audible command, or other triggering means. However, the illustrated variation depicts a rocker switch 112 where rear and forward 114, 116 rocking or triggering movement of the switch 112 either increases or decreases the strength of the stimulation signal. Accordingly, the system shown in FIG. 1 as well as the systems described herein include a dual purpose system that can operate in a nerve stimulation mode and an ablation/treatment mode.

As described below, the physician can adjust a degree of stimulation (i.e., the range from the device at which nerves are stimulated) as well as trigger stimulation, without moving the device 100 or hand 2 from the device. The device body 102 can generally include three operational switches (or a single switch with three positions. In the illustrated figure lateral operations/positions 114 116 of switch 112 either increases or decreases a stimulation current (or range) of the device. The center operation/position 118 initiates the stimulation mode. Once a physician locates an acceptable treatment site, the physician can initiate a therapeutic energy delivery mode by depressing a switch (e.g., 152 or 154) of the switch. In many cases the physician can initiate the therapeutic mode by depressing a foot pedal 152. Such a feature minimizes unintentional triggering of the therapeutic mode. However, variations of the device include the use of an optional switch 154 located on the device 100. In additional variations, the therapeutic mode can be triggered from the controller 150 and/or from continued operation of switch 112.

Additional variations of the device can include triggering of the energy delivery mode with either end of the switch and activation of the stimulation mode via the center of the switch or separate pedal as shown. Alternatively, or in combination, a separate switch (e.g., 154) can be positioned anywhere on the device body 102. FIG. 1 illustrates a sealed rocker switch 112 located at the forward ⅓ of the device body 102. Such a configuration allows ease of operational handling with the physician's index finger or thumb. Again, although the illustration shows a rocker switch, other single switch, multiple switches, and/or multi-function switch styles are suitable for the implementation of this aspect of the invention.

FIG. 1 also shows the working end 104 of the device 100 comprising a single axis probe. While the examples illustrated below comprise an electrosurgical energy modality, other energy modalities can be used in combination or in place of the electrosurgical modality. For example, such modalities can include: cooling, cryogenic, thermal RF, thermal (resistive heating), microwave, focused or unfocused ultrasound, thermal or non-thermal DC, UV, radiation, as well as any combination thereof, can be employed to reduce or otherwise control the ability of the nerve to transmit signals. FIG. 1 schematically illustrates the device 100 being coupled to a power supply 150, which can provide the energy modality required to perform the treatment as well as the stimulation energy used to locate a nerve. Additional variations contemplate a separate power supply (not illustrated) to power/control the stimulation energy. In additional variations, the handle 100 can contain the power supply. The term power supply is intended to include units where a controller regulates delivery of energy from the power supply. Accordingly, the power supply 150 described herein can include a controller. Alternatively, the controller can comprise a separate physical unit.

The devices described herein can also employ various features to provide feedback to the medical practitioner. For example, FIG. 1 illustrates a feedback indicator that can provide feedback to the medical practitioner. The feedback can be visual, tactile, vibratory, audio, or a combination thereof. Although the illustrated variation shows the feedback indicator 120 towards a distal end of the device body 102 variations of the device allow for an indicator that can be located on any portion of the device 100 and/or on multiple locations of the device. The feedback can comprise an indication of generator status, number of treatments, whether the device is within an acceptable range of a target nerve or ablation site FIG. 1 also illustrates an exemplary working end 104 of the device 100. As discussed herein, the working end typically includes a single axis probe 105 that has a distal end 106. In certain variations the distal end 106 includes a tip for a allowing penetration of the working end 104 into tissue. Alternatively, the distal end 106 can comprise a blunt shape that permits penetration of the working end 104 into tissue but minimizes undesirable collateral damage to tissue. The working end 104 will also include one or more energy delivery regions 106, 108, 110. For example, when the energy modality comprises an electrosurgical device, the working end 104 can include one or more electrodes 106, 108, 110 that are electrically isolated to pass current in a bi-polar or mono polar manner.

Any of the probes disclosed herein may include an illumination source 107 such as a fiber optic illumination, a light emitting diode, a laser source for assisting the physician in identifying the location of the percutaneously placed working end through tissue. The illumination source can be powered through the controller/power supply 150 or can be powered by a source in the device body 102 itself.

Figure 2:
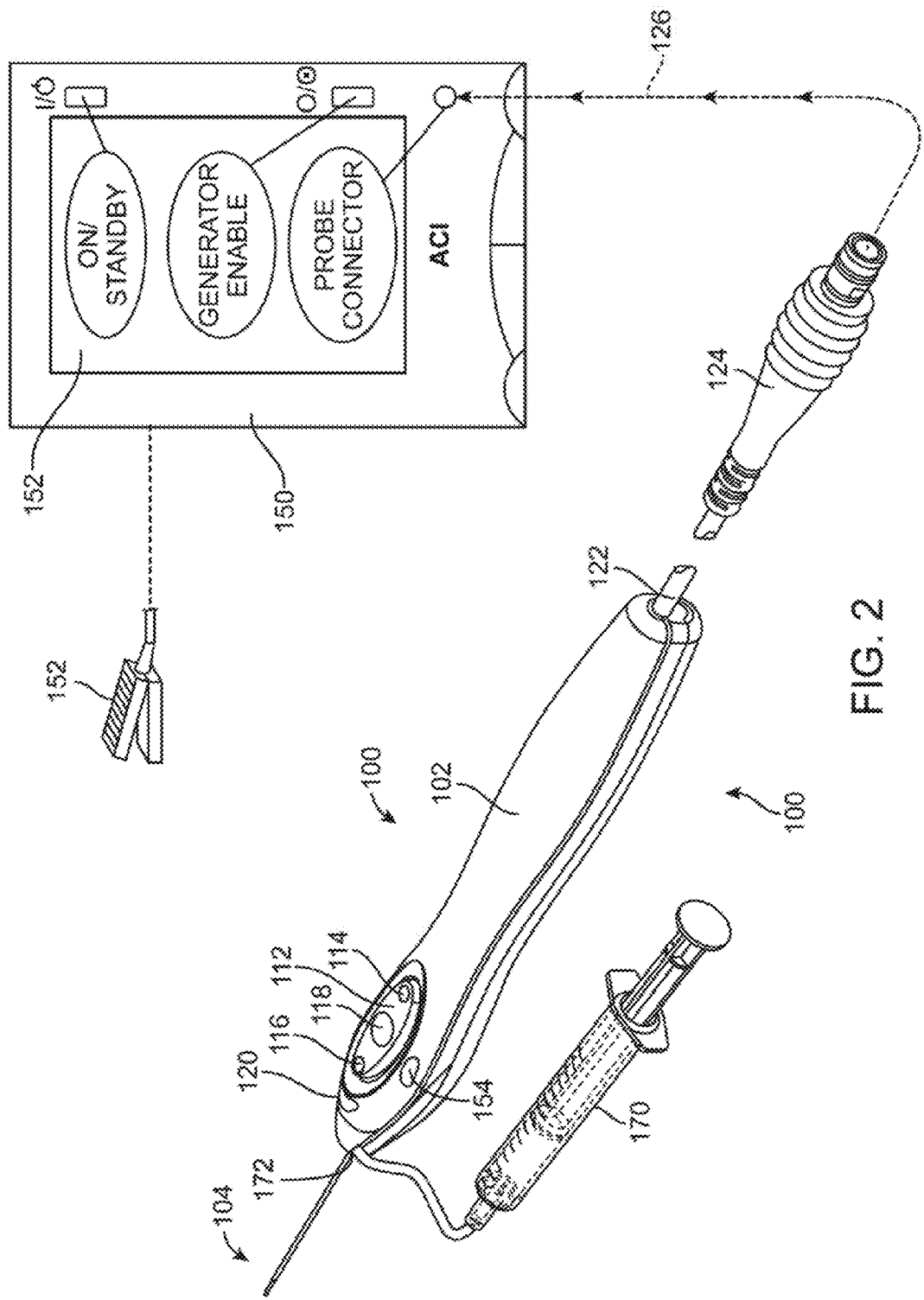
FIG. 2 illustrates another variation of a treatment device coupled to a reservoir delivery member as well as a controller/power supply.

FIG. 2 illustrates another variation of a treatment device 100 coupled to a reservoir delivery member 170. The device can also include a cable 122 or other connector that couples the device 100 to a controller/power supply 150. In the illustrated variation, the connector comprises a hub 124. However, alternate variations allow for a device 100 that is directly wired to the controller 150. The variation shown in FIG. 2 also depicts the reservoir 170 as being a separate syringe. However, alternate variations of the device include a reservoir that is fluidly coupled to the working end 104 through the hub 124 or cable 122 of the device 100. In such cases, there will be a means to pressurize or initiate flow of the substance within the reservoir. The reservoir 170 is typically a fluid source but variations include injectable particulates, gels, or other non-fluid injectable materials. The reservoir 170 can deliver any type of fluid to the working end 104 of the device 100. In the illustrated example, the reservoir 170 comprises a syringe with a plunger. Alternate variations include reservoirs coupled to electronic or automated dispensers.

Typically, the substance in the reservoir 170 comprises an aesthetic solution, cooling solution, conductive fluid, drug, cosmetic agent, and/or any other bio-active agent. Variations of the device and method include delivery of multiple substances through the device or to the target location. For example, a saline solution can be delivered to the target location to adjust the impedance of the tissue while an aesthetic agent can be delivered before, during, or after delivery of the saline fluid. As described below, the reservoir 170 is in fluid communication with ports at the working end to permit delivery of the fluid at or near the treatment site. The substance can be dispensed at anytime, including during penetration of the tissue, during movement within tissue, and before/during/after stimulation and/or application of energy. The substance can be a controlled volume that dispenses each time or can be an adjustable volume that dispenses based on the physician's preference. Moreover, dispensing can occur automatically prior to, during, or after treatment.

FIG. 2 also illustrates the controller/power supply 150 as having a visual display 150. The visual display can provide treatment information to the physician as well as device information. For example, the system can provide information regarding the number of applied treatments; the system can provide information regarding whether the treatment was successful (e.g., whether the target site held a pre-determined temperature and for how long). The system can also provide information on temperature and time profiles for each treatment. For example, in one variation the controller contains multiple pre-determined selectable treatment settings (e.g., 80 degrees, 70 degrees, and 85 degrees F.) and attempts to hold the treatment site at these temperatures for a pre-determined time (e.g., 30 second). In some variations a physician can determine which setting to use based on the location of the target site or if the skin is very shallow or thin at the target site. The controller can also establish a cutoff temperature above which treatment ceases. In one example the cutoff temperature is 93 degrees F. but can be as high as 130 degrees F.). The controller can also check for temperature during treatment, and if no rise in temperature is observed, the controller can either cease treatment or can apply a low amount of power. Additional safety measures can be employed such as establishing a step-up to the target temperature through a number of intermediate temperatures (e.g., x degrees above body temperature per unit time until the target temperature is reached). Furthermore, the system can monitor impedance and establish a maximum impedance at which the treatment stops. In one example, the system can monitor for impedance between 100 and 500 ohms with a shutoff of about 2000 ohms.

The variations shown in FIG. 2 also includes a contoured or ergonomic device body 102, which as described above, is suitable for single handed operation of the device 100 with the device body 102 being balanced in the web of a user's hand between the thumb and the index finger. This positioning allows the user to position a single finger on switch 112 to activate the switch 112 in a forward 116 or rearward 114 direction to adjust the stimulation settings of the system. As noted above, in certain variations, the forward 116 and rearward 114 movement allow for adjusting of the stimulation strength of the device 100 and, upon properly identifying the target location, the user's finger can select trigger 118 to apply the stimulation energy to identify the nerve. Once the physician identifies the target site, the physician can operate any number of switches 152, 154 as well as the combinations discussed above to commence treatment of the desired region of tissue.

Figure 3A:
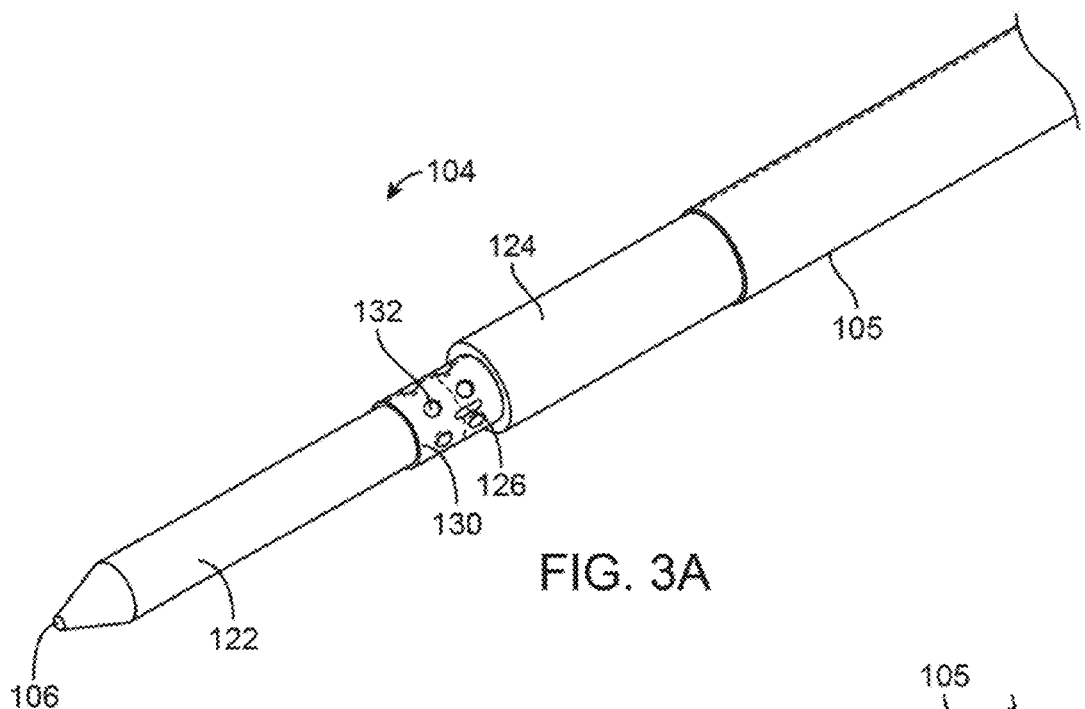
FIG. 3A illustrates a variation of a working end of a single axis probe having at least one energy transmitting region with sensors and/or fluid delivery ports positioned in the working end.

FIG. 3A illustrates one variation of a working end 104 of a single axis probe 105 having at least one energy transmitting region with sensors and/or fluid delivery ports positioned in the working end 104. The variation shown in FIG. 3A includes a first or distal energy transmitting region 122 and a proximal transmitting region 124. For example, the two energy transmitting regions 122, 124 can comprise electrodes of opposing polarity when using an RF energy supply. As shown, the two electrodes 122 and 124 can be positioned such that they are on either side of delivery ports 132 that extend through a sleeve 130 or similar structure that defines a fluid delivery lumen in fluid communication with a reservoir (as shown in FIG. 2). Optionally, a sensor 126 (such as a temperature detecting element) can be positioned adjacent to the energy transmitting regions 122 and 124.

The configuration shown in FIG. 3A permits delivery of fluids and/or substances in a central region to the intended target area. The device can include any number of fluid ports 132 includes from a single fluid port to a plurality circumferentially positioned around the device or simply limited to a single side of the device. The variation depicted in FIG. 3A shows a plurality of fluid ports 132 that are oriented to direct flow in a radial outward direction relative to a central axis of the single axis probe 105. One benefit of positioning the ports 132 in close proximity to the energy transfer units is that the substance can be delivered directly to the area of tissue targeted during the procedure.

Figure 3B:
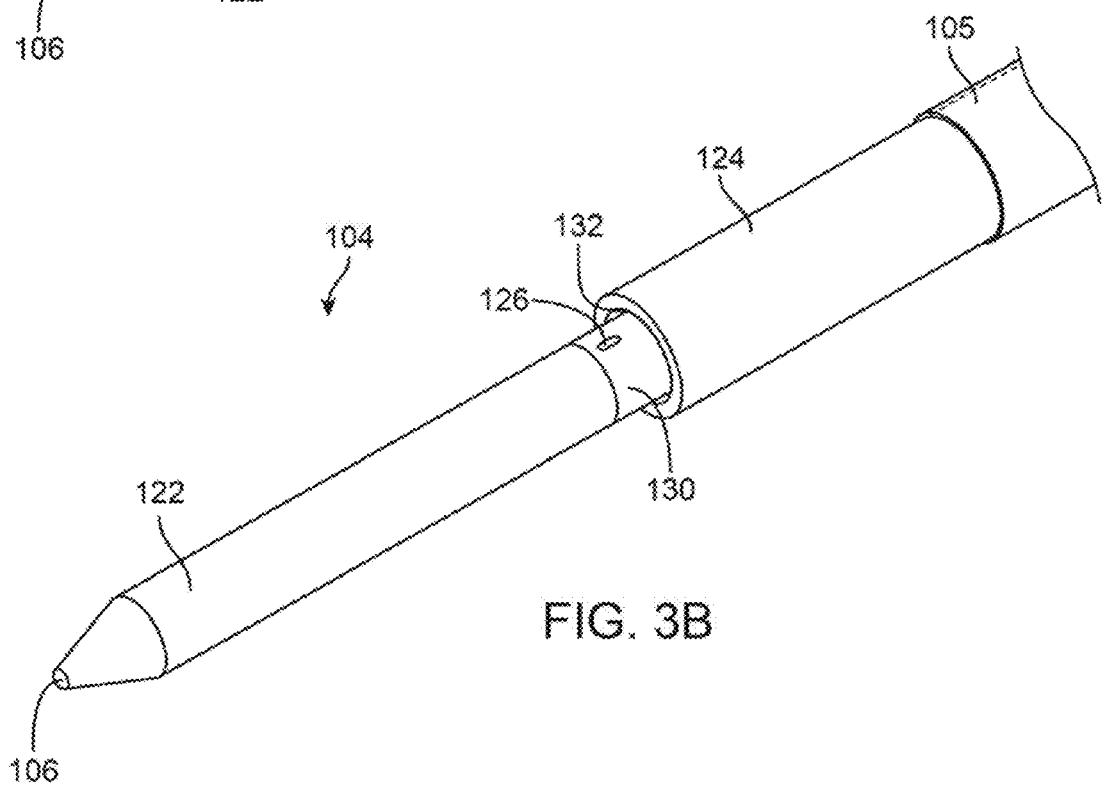
FIG. 3B illustrates another variation of a working end of devices described herein.

FIG. 3B illustrates another variation of a working end 104 of devices described herein. In this variation, energy transmitting regions 122, 124 are separated by a non-energy transmitting region 130 and a fluid delivery port 132 that is an opening to an annular passageway within the probe 105. FIG. 3I also illustrates that one or more sensor elements 126 can be placed between the energy transmitting regions 122, 124. In certain variations, the sensor elements 126 will be placed out of a flow-path of the ports 132 so that substances exiting the port 132 do not affect the readings of the sensor 126.

Figure 3C:
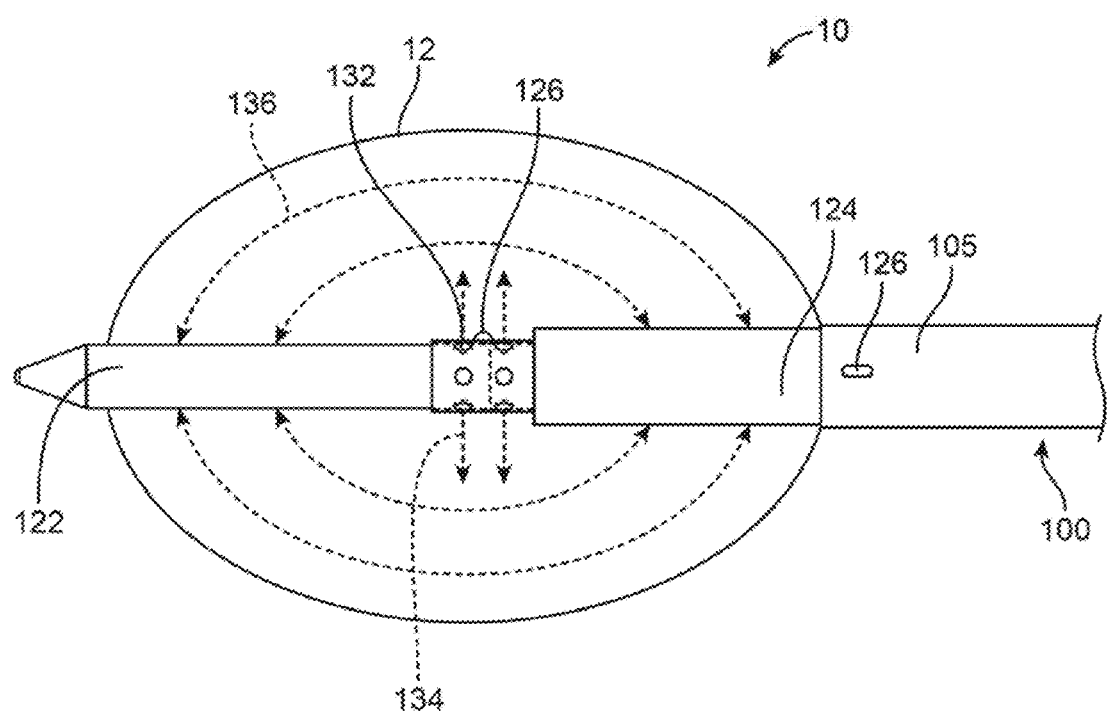
FIG. 3C shows an example of a device positioned in tissue where the energy transmitting regions and create a lesion within the tissue.

FIG. 3C shows an example of a device 100 positioned in tissue 10 where the energy transmitting regions 122 and 124 create a lesion 12 within the tissue 10. The illustration depicts application of an RF current 136 between the two regions 122, 124 however, as noted above, any energy modality can be applied which results in a lesion or treatment area 12 being formed about the energy transmitting regions 122 and 124. The depicted example illustrates the state of the device 100 after the physician identifies the proper location for treatment (e.g., after the stimulation mode identifies a suitable location for treatment). FIG. 3C also shows delivery of a substance 134 through the ports 132. In the illustrated variation, the ports 132 permit delivery of the substance in a direction that is radially away or normal to an axis of the probe 105. As discussed above, additional configurations are within the scope of this disclosure including combinations of ports oriented to deliver the substance in different directions on the same device. Regardless, the substance can be delivered prior to, during or subsequent to application of the treatment modality. In addition, positioning of the ports 132 adjacent to or between transmitting regions 122 and 124 allows for targeted delivery of the substance to the treatment area.

For example, in cosmetic applications it may be desirable to deliver a numbing agent to the region. In such a case, once a physician determines the proper placement of the working end of the device, the physician can deliver the numbing agent from the reservoir through the ports to the region of tissue to be treated. The close proximity of the ports to the target area allows for minimizing the amount of substance that must be delivered. Minimizing the amount and/or spread of the numbing agent is desirable since the numbing agent might impair a muscle's ability to respond to nerve stimulation.

As noted herein, the devices can include any number of energy modalities to provide the therapeutic treatment. Accordingly, the energy transmitting regions 122, 124 shown in FIGS. 3A to 3B are not limited to RF energy electrodes. In additional variations, the regions can comprise cooling regions, cryogenic fluids, thermal RF, resistive thermally heated regions, microwave antennas, focused or unfocused ultrasound transducers, thermal surfaces powered by a DC current, UV, radiation, as well as any combination thereof. In those variations relying on a Radio Frequency energy supply, the two energy transmitting regions 122, 124 can comprise electrodes of opposing polarity. Regardless of the energy type used, it can be desirable to position a sensor 126 (or other sensor) between the transmitting regions 122, 124. However, alternatively, or in addition, one or more sensors can be positioned along the probe 105 or on any other portion of the device.

FIGS. 4A to 4G illustrate use of devices and systems described herein when used to perform a treatment in a patient. The example shown illustrates use of the device 100 to ablate one or more regions and/or branches of a temporal nerve which controls movement of facial muscles. However, it is understood that the methods, features, and aspects described herein can be applied to any nerve structure controlling any observable/measurable body function.

Figure 4A:
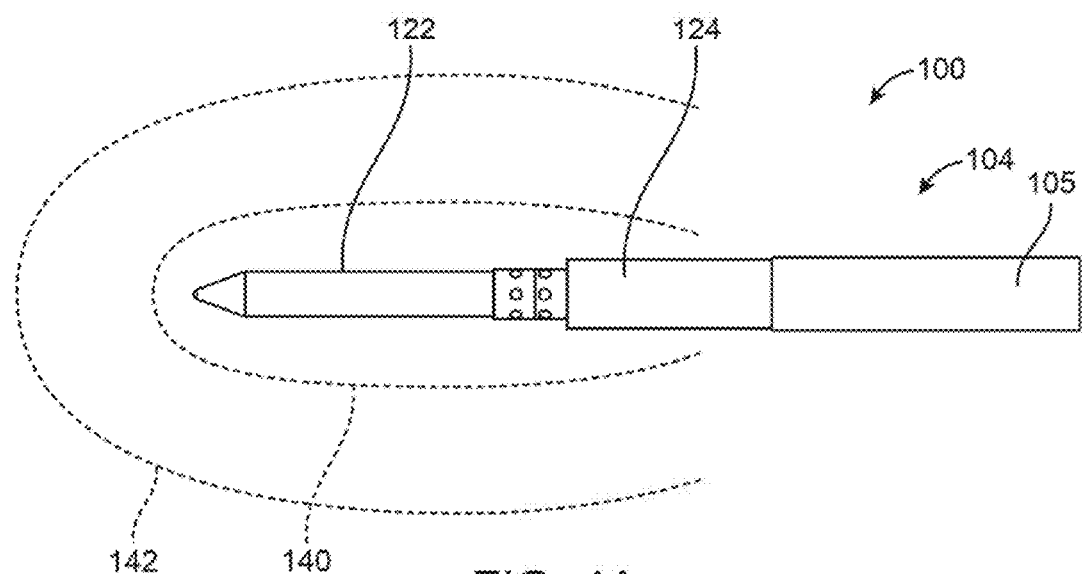
FIGS. 4A to 4G illustrate use of devices and systems described herein when used to perform a treatment in a patient.

FIG. 4A is intended to illustrate a feature of a system similar to those discussed herein where the treatment device 100 can be operated in a dual purpose mode to provide nerve stimulation and therapeutic treatment. In one variation, the stimulation function passes pulsed direct current between the energy transfer surfaces 122 124 in the working end 104 of the probe 105 to operate in the nerve stimulation mode. In additional variations, the nerve stimulation mode can provide alternating current (or RF generated current) to identify nerves via muscle as known by those skilled in the art. Regardless, when used in a stimulation mode, the working end 104 of the device 105 applies current to the tissue to stimulate the nerve which produces movement in the muscle that the nerve is controlling. This movement can be physically observed (e.g., by feeling for the movement of muscle), or visually observed (e.g., when the physician stimulates and observes which muscle or which part of the face has movement). Moreover, any number of pacing devices or camera devices can be used to detect movement The device 100 can operate in a plurality of settings that stimulate the nerve. As long as the working end of the device is sufficiently close to the nerve, where the distance is dependent upon parameters of the applied current (e.g., amount of current or the amplitude of the current). Cycling of the current causes contraction and relaxation of the muscle which can be observed by the physician or by other sensing/identifying means. The amplitude of the current can be adjusted from the probe body or from the controller. The intensity of the stimulation is directly related to the amplitude of the current and the proximity to the motor nerve. As the physician gets closer to the nerve he/she can reduce the amount of stimulation current and still observe muscle contraction. When the stimulation current is low (<<0.7 mA) and muscle contraction is observed, the probe electrodes are in close proximity to the target motor nerve. In one working example, it was found that the low stimulation current (e.g., 0.7 milliamps) produced stimulation of nerves within 2 mm of the device's working end. Knowing that the device is within a certain range of a nerve permits the system to apply energy that will have an effect within that range.

For example, in the current example, if the nerve/muscle becomes stimulated using the threshold stimulation energy (e.g., the low stimulation current), then the physician and/or sensing identifying means will confirm that the working end of the device is placed within an effective distance/range of the target tissue (e.g., the nerve) to apply the therapeutic energy in a controlled manner without producing undesirable collateral damage or encompassing tissue that is well beyond the target tissue. In one variation, stimulation using the threshold stimulation energy/current allows the system to apply stimulation energy while delivering therapeutic energy and maintaining a pre-determined target therapeutic temperature for a pre-determined amount of time. The physician and/or sensing identifying means will confirm that a effective therapeutic endpoint on the target tissue (i.e. nerve) has been reached. It is understood that the design of the electrodes or treatment areas can affect the range (including lesion size, shape, volume, and isotherms) of the device as well. After locating the motor nerve, radiofrequency energy is applied through the same electrodes to heat the tissue and inhibit nerve function. Once an RF lesion is placed on the nerve communication between the brain and the muscle is disrupted and the patient can no longer actuate the muscle.

FIG. 4A represents the effect of two parameter settings in the stimulation mode. In the first parameter setting, the device 100 can stimulate nerves in tissue at a first distance 142. At the second parameter setting, the device 100 stimulates nerves at a second distance. As shown in FIG. 4A, the first distance is greater than a second distance. Such functionality allows the physician to operate the system at the first parameter setting to generally locate the target nerve. To position the working end 104 of the device 100 closer to the target, the physician changes to the second parameter setting and checks for contraction and relaxation of the muscle governed by the target nerve. Because the stimulation range 140 of the device 100 is limited, stimulation of the target muscle confirms that the working end 104 is close to the target site on the nerve. If the physician operates the device 100 at the second parameter setting and does not observe any muscle movement, the physician will know that the working end is not optimally positioned relative to the nerve. Clearly, the system can include any number of parameter settings. Moreover, the ranges 140 and 142 are for illustrative purposes only. In one working example, the second parameter range is approximately 0.7 milliamps and corresponds to a range 140 of less than 2 mm. Again, the parameter levels and ranges can be adjusted depending upon the application, area of tissue, degree of stimulation required, etc. In another variation of the device and system, the controller/power supply (and/or features on the device 100 itself) prevent the device from operating in the therapeutic mode unless the device is toggled to the second parameter setting corresponding to a smaller stimulation range 140.

In another variation, instead of being prevented from applying treatment, the system can provide a warning to the physician that the stimulation mode is not in a preferred mode to apply therapeutic treatment. Accordingly, the system can require a physician override so that the physician purposefully performs the therapeutic treatment.

Figure 4B:
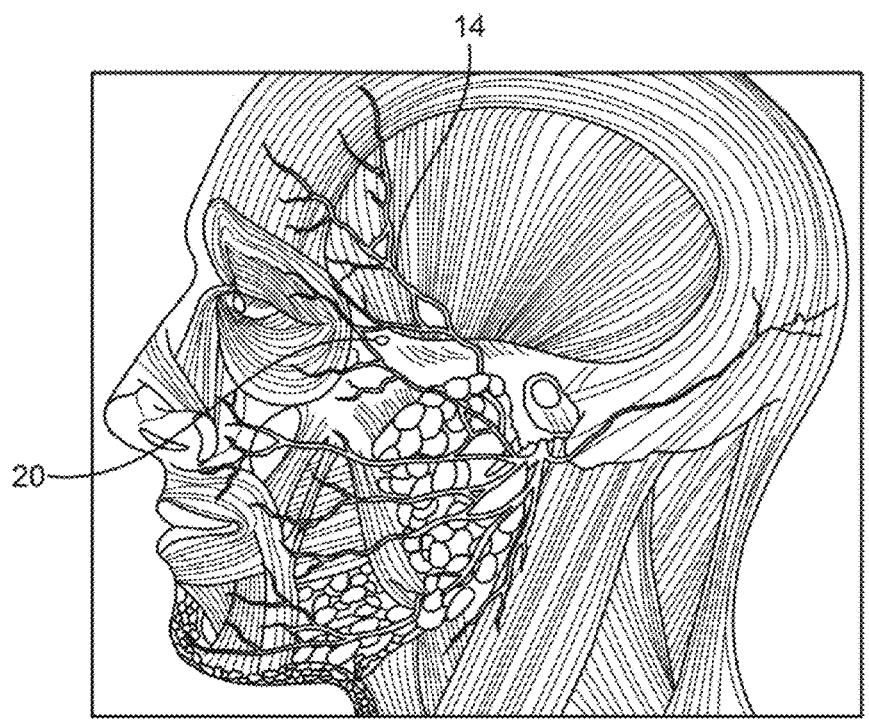

FIG. 4B illustrates a temporal nerve branch 14 and an access point 20 where a physician advances the probe 105 of the device 100 to position the probe underneath skin and adjacent to the target nerve. As discussed herein, variations of the invention can use a single axis probe to minimize the entry wound 20 and to accurately trace along the nerve 14. In alternate variations, a multiple axis probe can be used with the varying parameter functionality discussed herein.

Figure 4C:
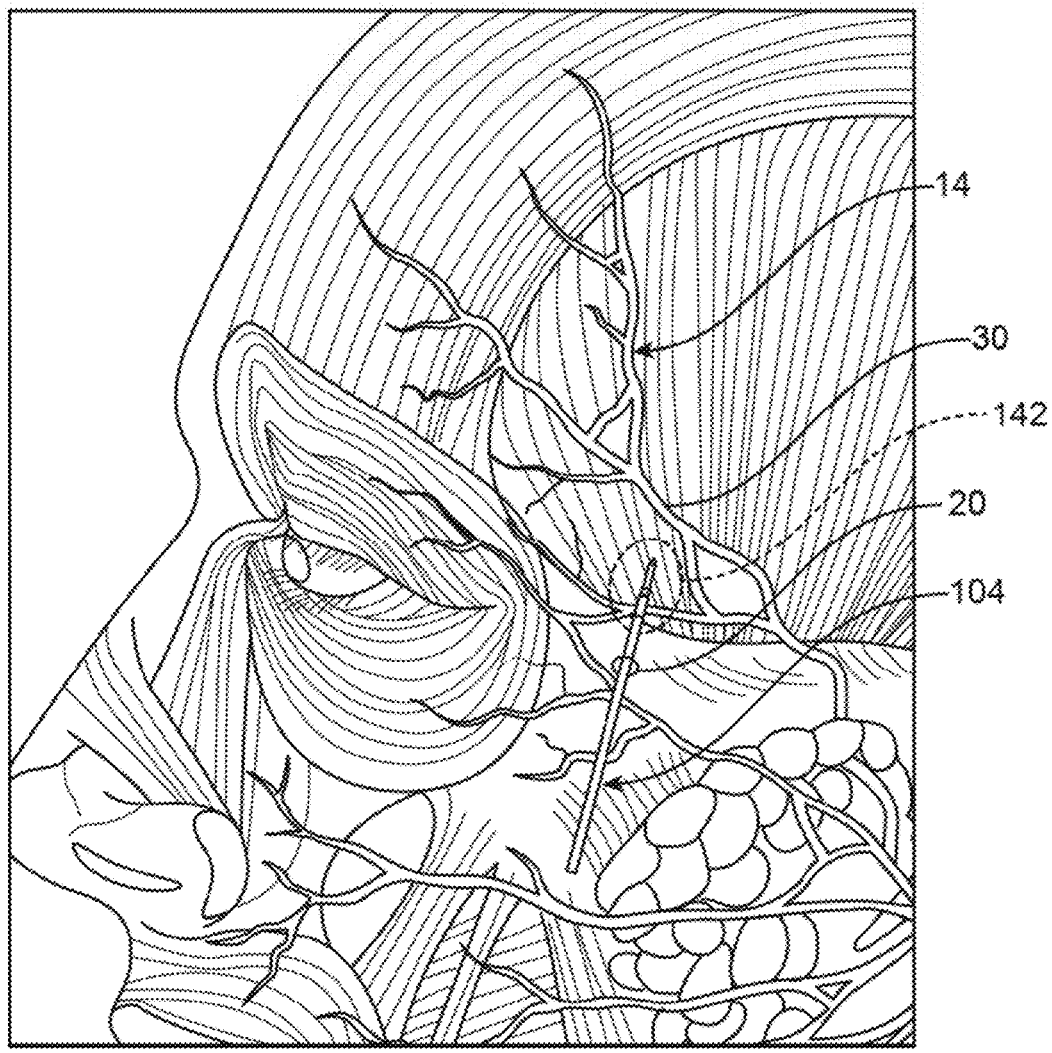

FIG. 4C illustrates a working end 104 of the device being advanced through the access opening 20 towards the nerve 14. As shown, the device can operate in a first parameter setting such that the stimulation distance 142 is sufficient to allow the physician to generally locate the nerve responsible for a particular muscle. Opening 20 is not limited to the location as illustrated. The probe can access any part of the body as needed.

During the process of probe placement, the stimulation current level may be increased or decreased as described by sequentially depressing one or more switches on the device (see FIGS. 1 and 2 above). A speaker associated with the system may emit a tone having a volume or frequency or other sound and/or visual attribute substantially proportional to the amplitude setting of the stimulation current with each switch closure. This feature permits the practitioner to adjust the stimulation level without the necessity of adjusting any level dials or switches associated with the generator, allowing the practitioner to focus on critical probe placement.

In one variation, as the physician locates the nerve 14, the physician can adjust the system to the second parameter setting thereby lowering the stimulation range 140. As illustrated, stimulation of the nerve 14 when in the second parameter setting shall inform the physician that the energy transfer portions of the working end are sufficiently close, immediately adjacent and/or contacting the desired target area 30.

Figure 4D:
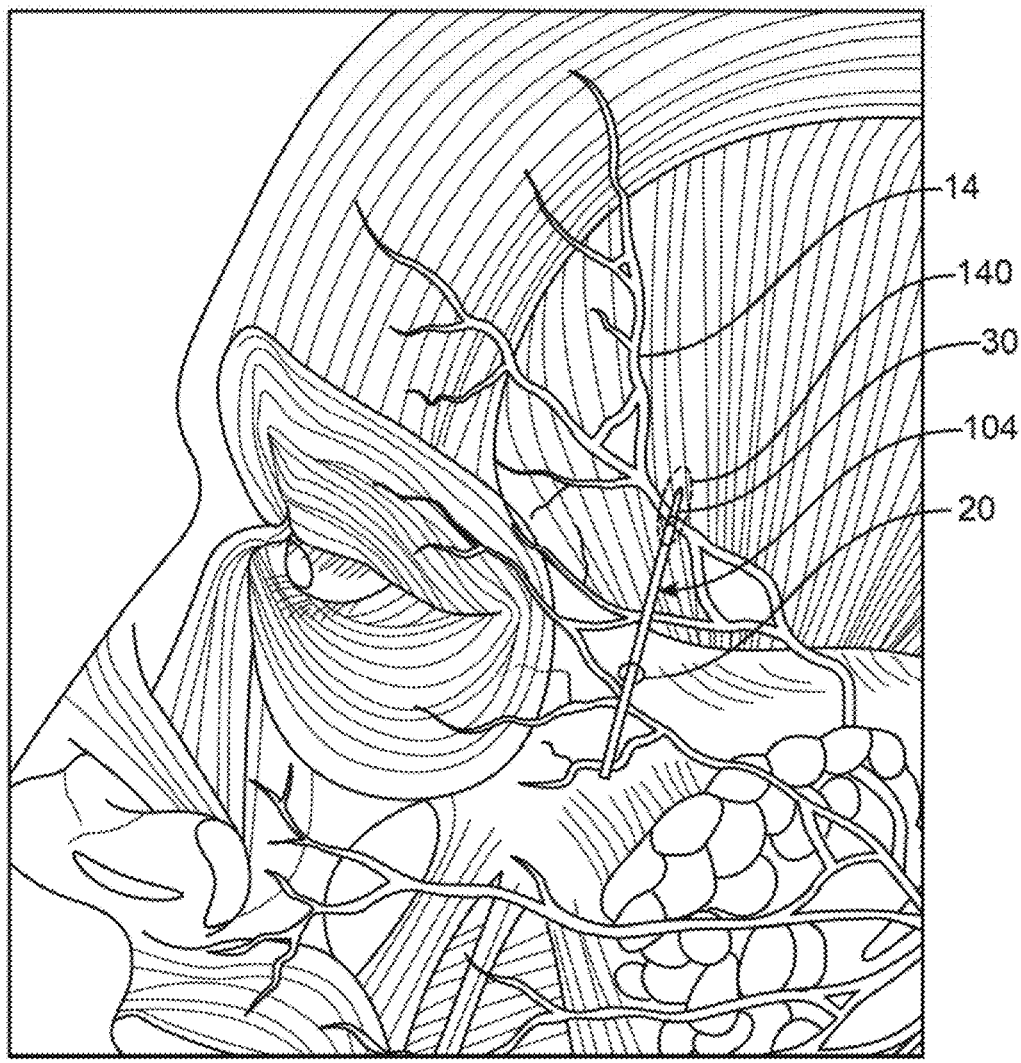

FIG. 4D represents the reduced stimulation range 140 as the device is operated in the second parameter setting. Upon observing muscle movement, the physician can enter the therapeutic mode of the system by operating the switch that applies the therapeutic energy/treatment (described above) without moving the device. Once in the therapeutic mode, the physician can ablate or otherwise treat the target area 30. As noted above, because stimulation of the target nerve occurs when using the threshold current the system can effect treatment of the nerve by applying a pre-determined amount of therapeutic energy that has a known effect on the tissue (either controlling for a specific temperature and/or time as described above). In certain variations, the pre-determined amount of energy is set to ensure that the therapeutic effect does not extend beyond the threshold stimulation range of the device (i.e., the range of the device when using the threshold energy, e.g., range 140 of FIG. 4A).

In an additional variation, the system can treat the target area 30 using a setting that produces muscle contraction or stimulation during the therapeutic application of energy. Accordingly, the physician can observe stimulation of the associated muscle during treatment. In such a variation, the physician can confirm the treatment when the associated muscle ceases movement. It is believed that twitching of muscle occurs when nerves enervating a muscle are depolarized. If the frequency is sufficiently low (e.g., 60 Hz) then nerves can be depolarized directly.

Figure 4E:
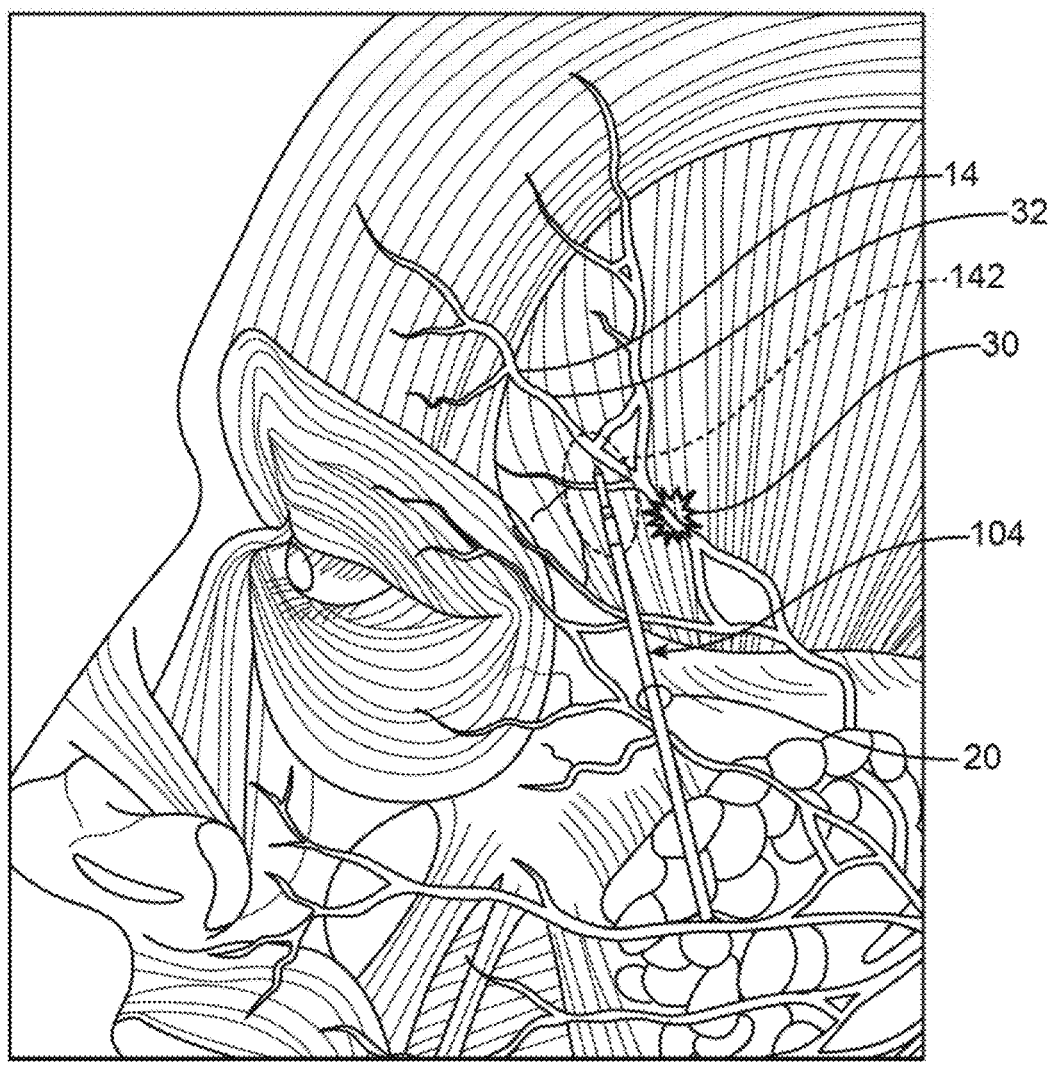
Figure 4F:
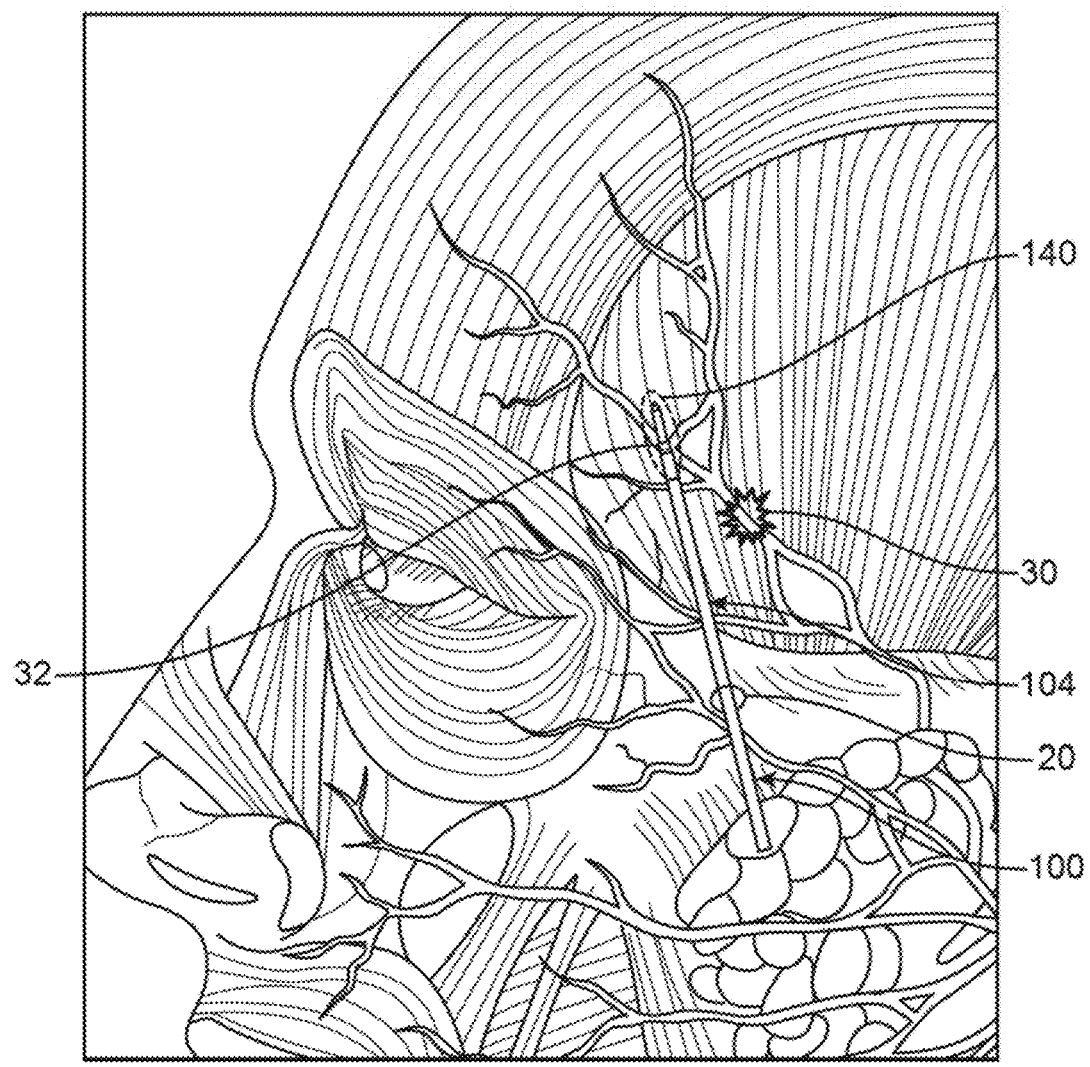

FIG. 4E depicts the physician advancing the working end 104 along the nerve 14 through the same opening 20 and also depicts another feature of the system where the device and/or controller/power supply automatically readjusts or switches to the first parameter setting corresponding to a greater stimulation range 142 as opposed to the reduced stimulation range 140 of the second parameter setting. As noted above, in certain variations, when the system is in the first parameter setting the system prevents a use from applying therapeutic treatment. In certain variations, the system can only apply therapeutic treatment when in the second parameter setting. One benefit of this feature is that the physician, having moved the device from first treatment site 30 towards second treatment site 32, must affirmatively readjust the parameter settings to the first parameter setting to ensure that the energy transfer surfaces of the working end are sufficiently close to the intended nerve and/or target site 32. FIG. 4F shows the device 100 where the physician reselects the second parameter setting corresponding to the reduced stimulation range 140. Once the physician positions the device through identification of associated muscle movement, the physician can apply the therapeutic treatment without moving the device. As shown, the second location 32 is along an imaginary longitudinal axis of the nerve distally to the more proximal location 30. Such "proximal to distal" directional ablation along the longitudinal axis of the nerve is believed to increase the effect of the duration of treatment.

Figure 4G:
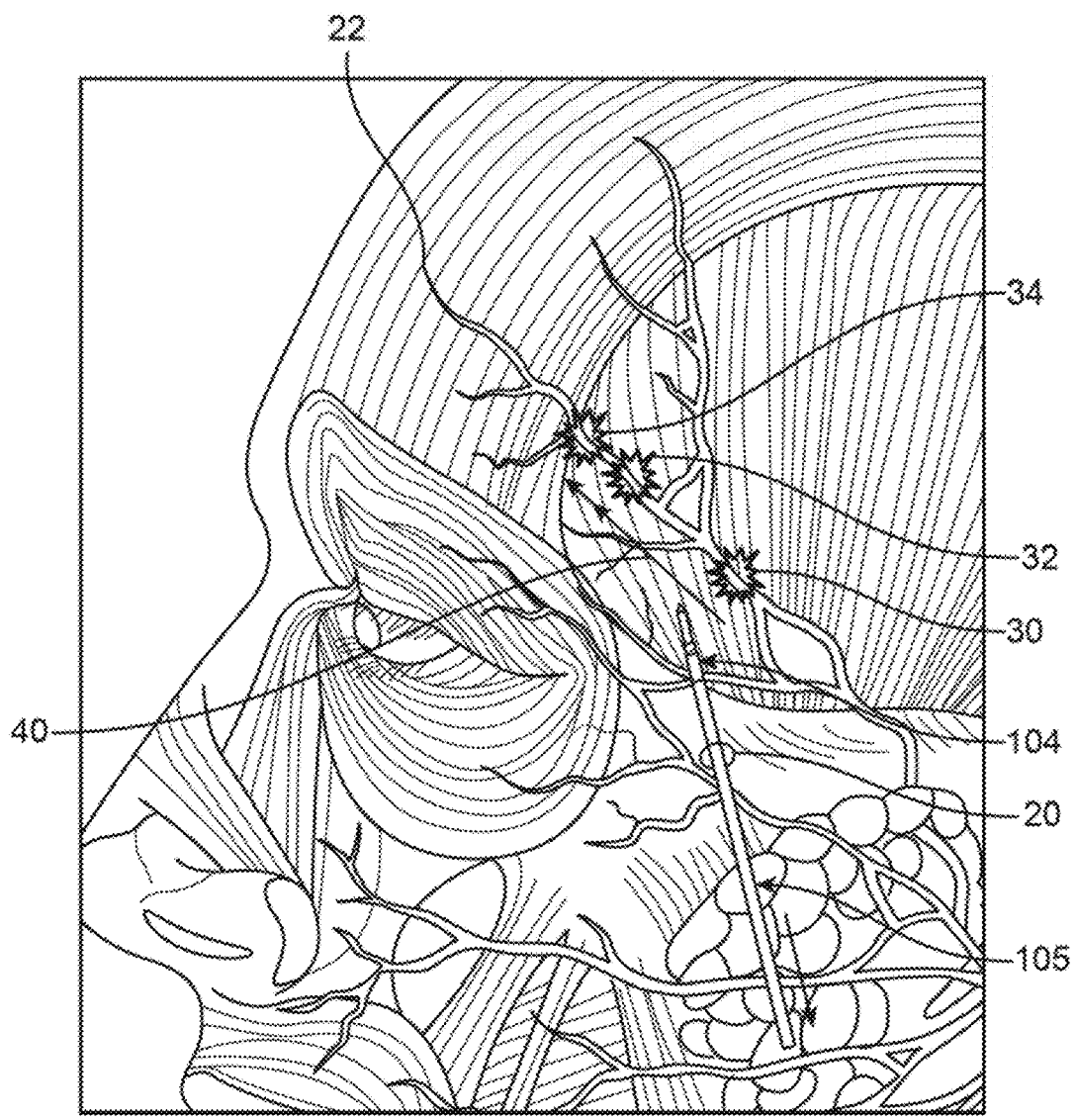

FIG. 4G illustrates a variation of a treatment procedure where a physician identifies and creates treatments at three locations 30, 32, 34. For clarity, the illustration shows the working end 105 being withdrawn through the access point 20. The illustration also shows a distinctive feature of the dual-purpose probe that provides an ability to create multiple lesions 30, 32, 34 on the same nerve or within a region of nerves that control one or more muscles that require treatment. In the illustrated example, the physician creates an initial lesion 30. This initial lesion disrupts communication to the nerve but the section of the nerve from lesion 30 to the muscle (denoted by region 22) remains intact. This intact region of the nerve allows the physician to continue using the stimulation function of the probe to further stimulate movement of muscle region 22 by moving the probe in a distal direction (i.e., in a direction closer to the muscle region 22 along the nerve). Movement of the device in this manner permits the physician to precisely relocate the device on the same nerve (or on a different nerve branch that controls muscles requiring treatment). As long as the probe tip advances distally along the nerve from the initial lesion (toward the muscle) the physician can locate the nerve through stimulation and observation as discussed above. In the illustrated example, the lesions are created in three sequential processes with the initial lesion 30, the next lesion 32 and final lesion 34 being formed in succession. The stimulation mode causes muscle contraction as long as the probe is distal to the last lesion.

The process of relocating the nerve and applying multiple lesions on a single nerve can be applied to ensure long term effect of the treatment. Multiple lesions along the same nerve (or same nerve region) increase the longevity of effect given that the nerve must heal in three locations prior to being able to relay signals. It is believed that multiple lesions assist in the longevity of the duration of the treatment since, it is believed that, nerves heal proximal to distal. Meaning that the most proximal nerve injury (e.g., 30) will most likely heal allowing communication to be re-established along the nerve prior to the more distal nerve injuries (i.e., 32 and 34).

In another variation, as shown in FIGS. 4A to 4G, a method for creating multiple lesions on the same nerve include using external stimulation device and map nerve location to get rough indication of nerve location. Then the physician inserts the probe or device probe into tissue. The physician then uses the stimulation function, to locate the target nerve. In variations, the stimulation function is automatically set to a parameter setting that increases a stimulation range of the device but also prevents the device from firing the therapeutic/ablation treatment. The physician will then adjust stimulation current to precisely located nerve and confirm muscle contraction. Assuming the stimulation parameters are set to reduce the stimulation range of the device and the physician confirms positioning of the probe via observation, the physician can then initiate the therapeutic mode of the device (e.g., by applying energy to affect the ability of the nerve/tissue to transmit neural signals, or ablating the nerve/tissue). In certain variations, the system will automatically reset to the first parameter stimulation settings, which increases a stimulation range of the device and prevents the device from activating in the therapeutic mode. Next, the physician can optionally advance the probe to a new location distal to the initial lesion and will repeat the stimulation and treatment. The physician can repeat the subsequent treatments along the nerve as desired to create any number of lesions.

Variations of the device include at least three parameter settings where two parameter settings correspond to a much reduced range of stimulation than the third parameter setting. In such a case, the two reduced parameter settings can correspond to a first acceptable range and a second finer range. Such a setting would allow a physician to locate the device relative to a nerve with varying degrees of accuracy.

Figure 5:
FIG. 5 illustrates another feature of the dual function device where the fluid ports located on the device deliver a substance between treatment portions of the device.

FIG. 5 illustrates another feature of the dual function device 100. In this variation, the fluid ports located on the device deliver a substance 134 between treatment portions 122 124 of the device. In the example, the substance comprises an anesthetic or numbing agent to create a limited zone 44 of effect (as illustrated by the shaded portion of FIG. 5). One benefit of this configuration is that application of a numbing agent over a larger area can potentially interfere with the ability of a nerve to stimulate the muscle. Accordingly, if the numbing agent affects the nerve so that it can no longer trigger muscle movement, or if the areas of the nerve distal to the first treatment site cannot be stimulated, the effectiveness of the procedure might suffer. Variations of the procedure include delivering the numbing agent before, during and/or after the step of applying therapy. In certain cases it is desirable for the patient to maintain motor control over the muscles being treated since the physician can ask the patient to contract the muscle. Contraction of the muscle allows the physician to determine the progress of the treatment. In such cases it can be undesirable to blanket the face or muscles with an anesthetic since the patient will be unable to contract his/her muscles. <Examples of numbing agents include dilute lidocaine 1 or 2 percent, lidocaine with epinephrine, and septocaine. However, any numbing agent can be used.

FIGS. 6A and 6B illustrate various additional examples of creating treatment sites to effect a therapeutic benefit. FIG. 6 illustrates a first lesion 30 on a proximal or main branch of a nerve with a second 32, third 34, and fourth 36 lesions on separate branches of the nerve 14. As discussed above, the sequence of the ablation sites is based on a proximal to distal direction (e.g., away from the insertion point, or towards muscle). FIG. 6B shows an example of a treatment of multiple lateral nerve branches. As shown in FIG. 6B, a variation of the procedure includes applying lesions to "lateral" branches of the primary nerve proximal to the muscle. The desired effect, of inhibiting nerve function, therefore eliminating hyperdynamic facial lines (wrinkles) caused by the muscle activity, can be achieve by applying a single lesion to multiple nerve branches of the temporal nerve. Although not required the first lesion 30 is positioned closes to the access point 16 and farthest from the target muscle, the second lesion 32 is formed distal to the first lesion 30 and the third lesion 32 is formed distal to the second 32 where each lesion is on a different branch of the temporal nerve 17.

Figure 6C:
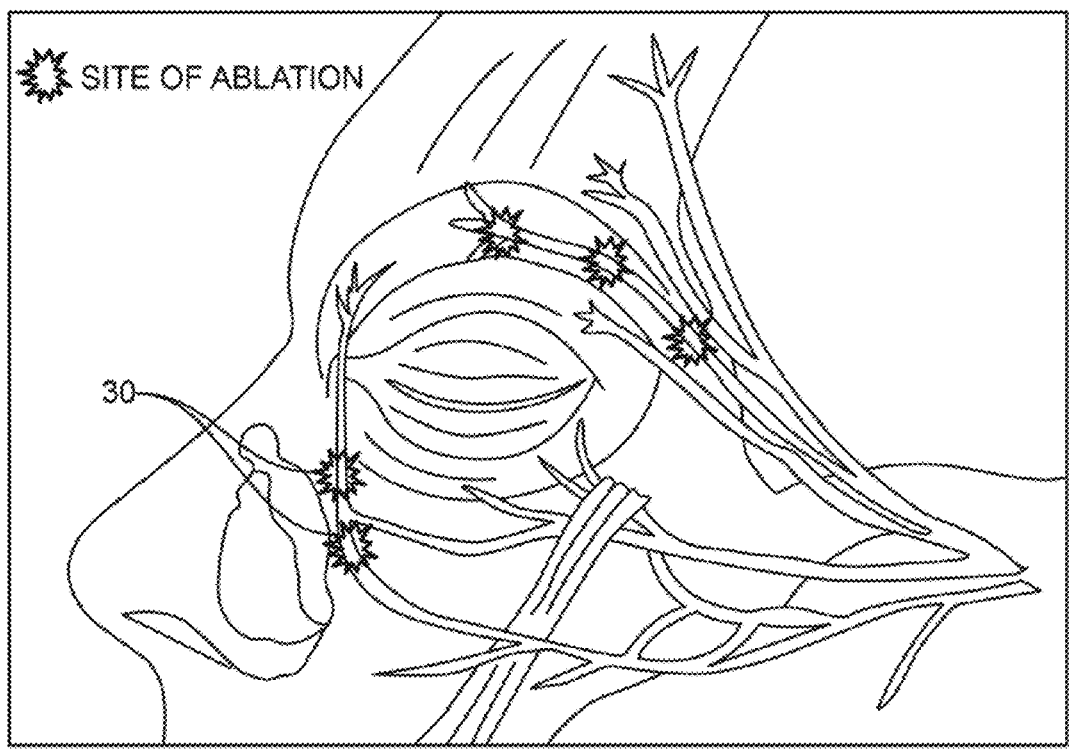
FIG. 6C illustrates another example of lesions being created on the angular nerve in a manner as described herein.

FIG. 6C illustrates another example of lesions 30 being created on the angular nerve in a manner as described herein. As noted above, the methods and devices of the present disclosure can be created in any number of areas of the body and along any number of nerves.

Figure 7:
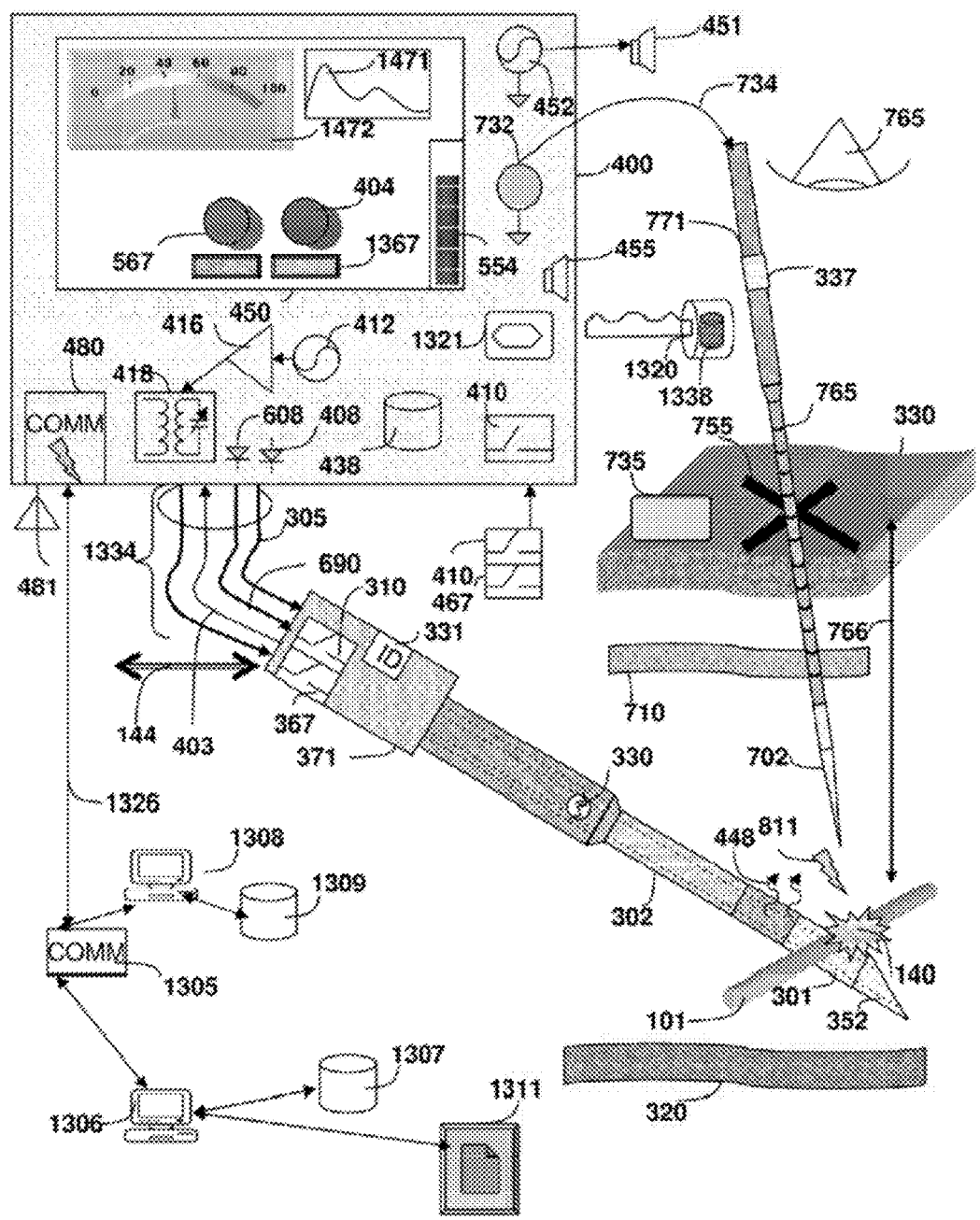
FIG. 7 Bi-Polar Driver System.

FIG. 7 Alternate Variations of Bi-Polar Driver System

FIG. 7 identifies the two required components of the system, various modules and optional items. The two components always utilized during a procedure will be the energy generator/controller/data storage device 400 and probe 371. 400 contains advanced electronic systems capable of recognizing a properly authorized probe, preventing re use of a previously used probe, generating appropriate energy as described, performing safety checks, storing data, and other functions as described. Main functions of 400 may include, but not be limited to, generation of light, generation of location-stimulation currents, generation of ablation energies, data logging, storage, communication and retrieval, and other functions critical to a MIS procedure. Probe 371 and its various forms are single puncture bipolar surgical tools that may be used in identifying proper location of its tip 301, in relation to target tissue 101 which is desired to be ablated, modified or destroyed. Probe 771 and its various derivatives may optionally be used to assist in locating and properly positioning tip 301 of probe 371.

Figure 8A:
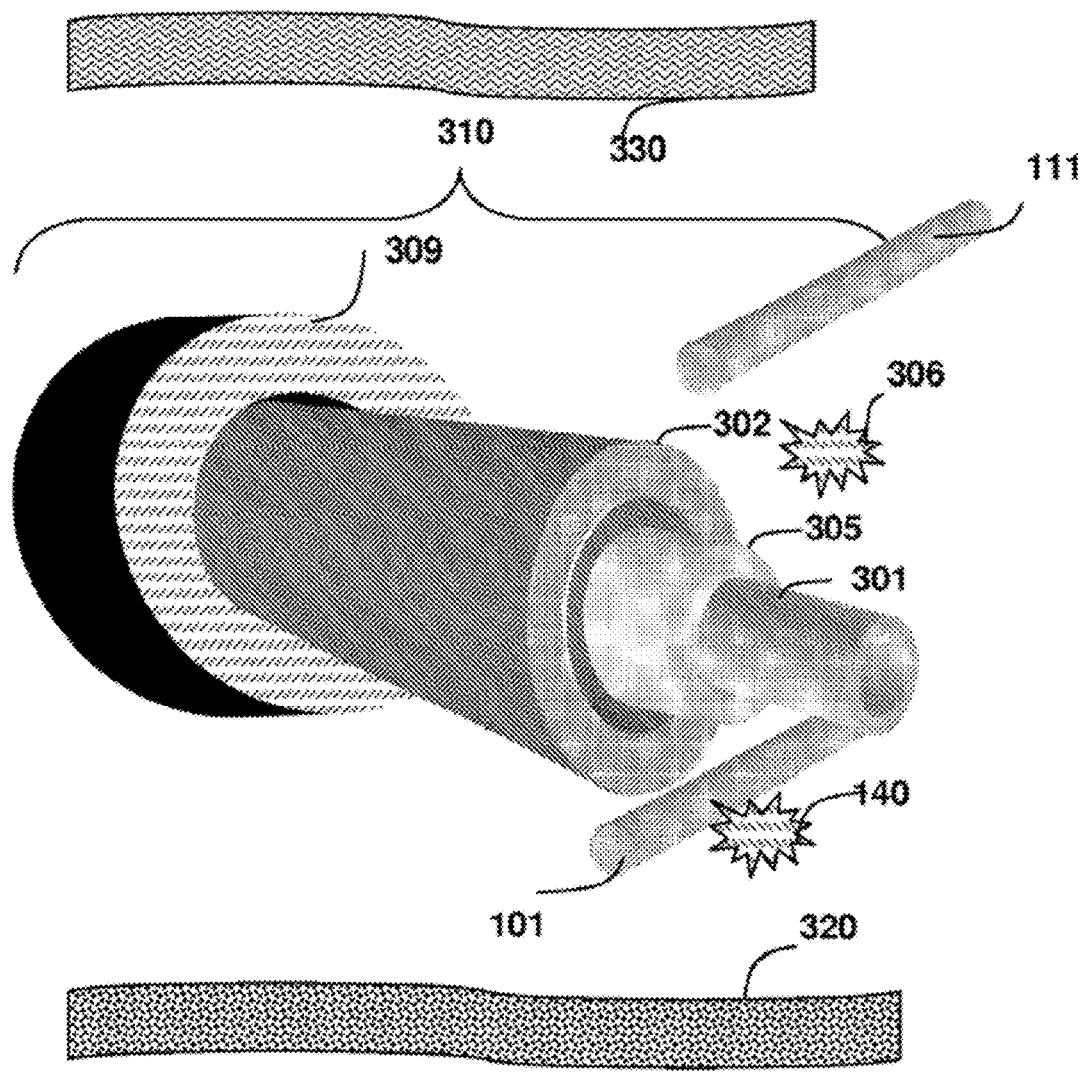
FIG. 8A Schematic diagram of the bi-polar needle.
Figure 8B:
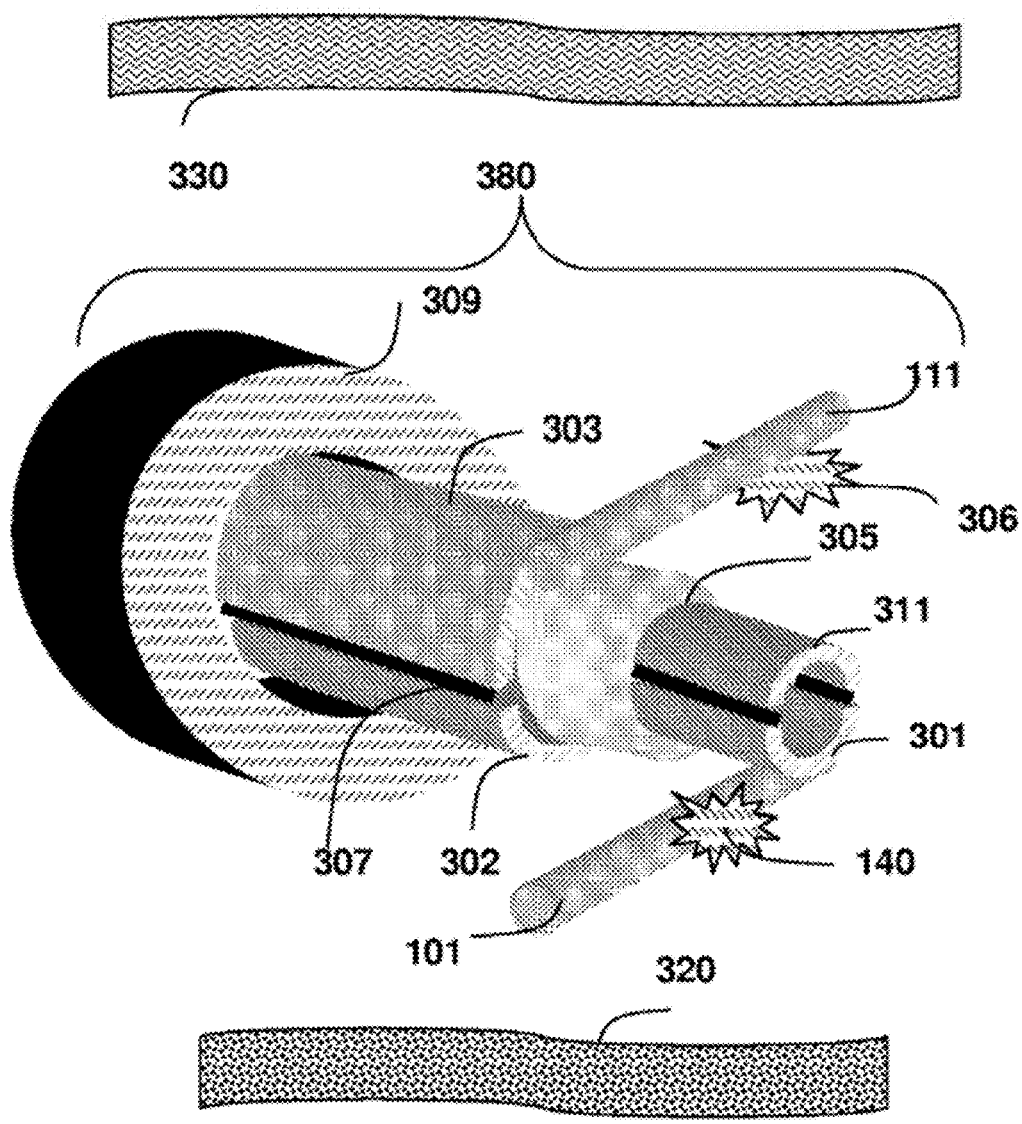
FIG. 8B Schematic diagram of the split bi-polar needle.

FIGS. 8A and 8B Isometric View of the Bi-Polar Probe

Figure 9A:
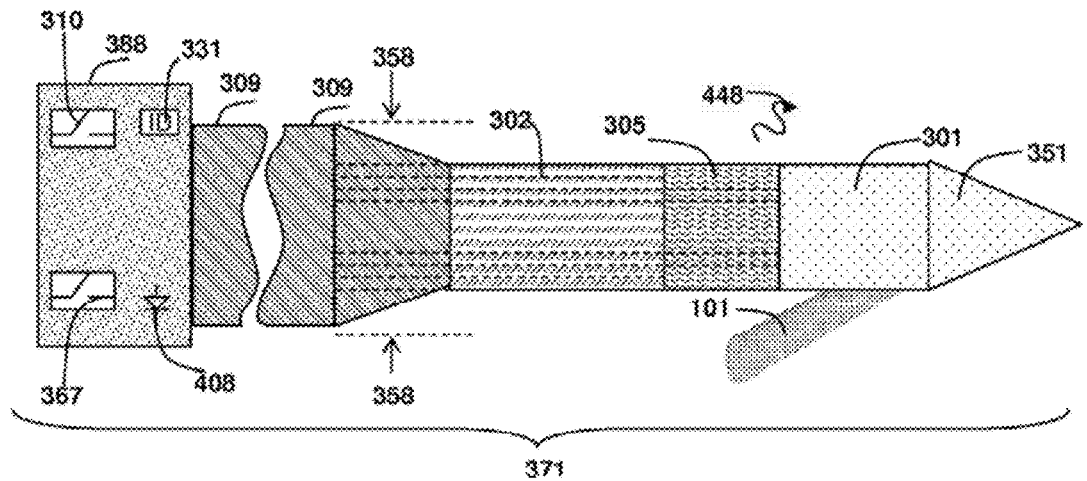
FIG. 9A Magnified side view of conical bi-polar probe.
Figure 9B:
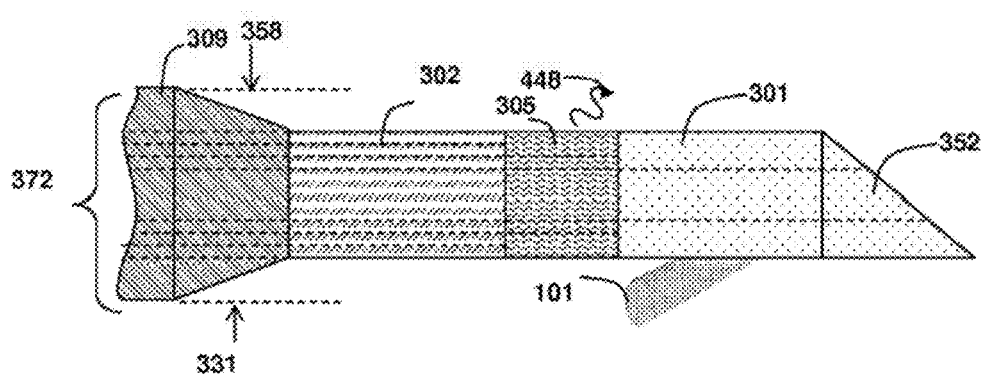
FIG. 9B Magnified side view of hollow chisel bi-polar probe.
Figure 9C:
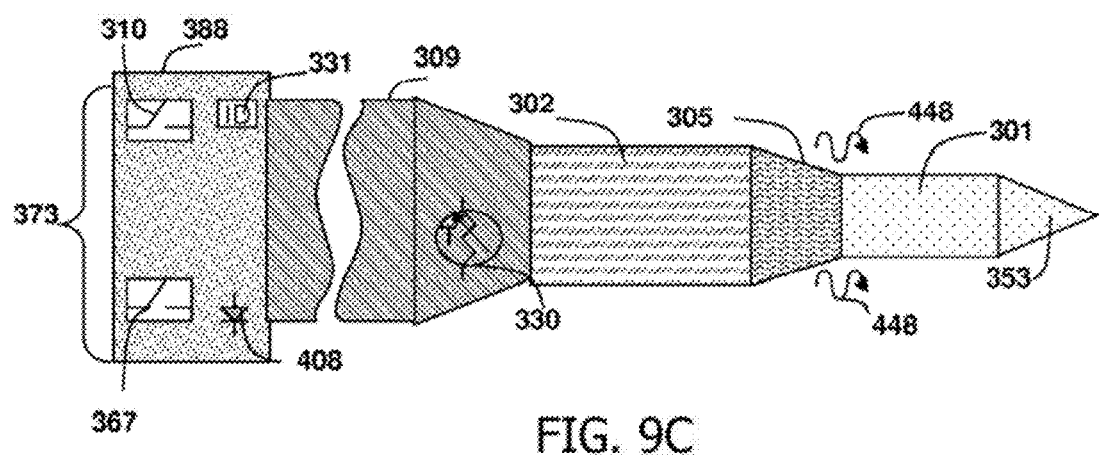
FIG. 9C Magnified side view of tapered conical bi-polar probe.
Figure 9D:
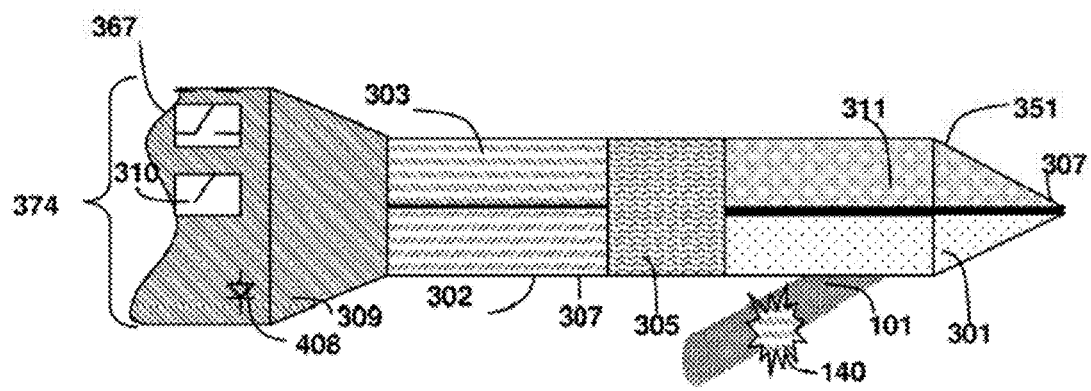
FIG. 9D Magnified side view of split conical bi-polar probe.

Bi-polar probe 310 represents probes 371, 372, 373 shown in FIGS. 9A-9C with exception to type of needlepoint on the probe. FIG. 9D varies from the other because it has a split return probe. Bi-polar probe 310 (not drawn to scale) consists of insulating dielectric body 309 made from a suitable biology inert material, such as Teflon, PTFE or other insulative material, covering electrode 302 except for where 302 is exposed as a return electrode. Conductive return electrode 302 tube is fabricated from medical grade stainless steel, titanium or other conductive material. Hollow or solid conductive tip electrode 301 protrudes from surrounding dielectric insulator 305. Sizes of 309, 302, 305, and 301 and its inner lumen (diameter, length, thickness, etc.) may be adjusted so as to allow for different surface areas resulting in specific current densities as required for specific therapeutic applications.

Figure 10:
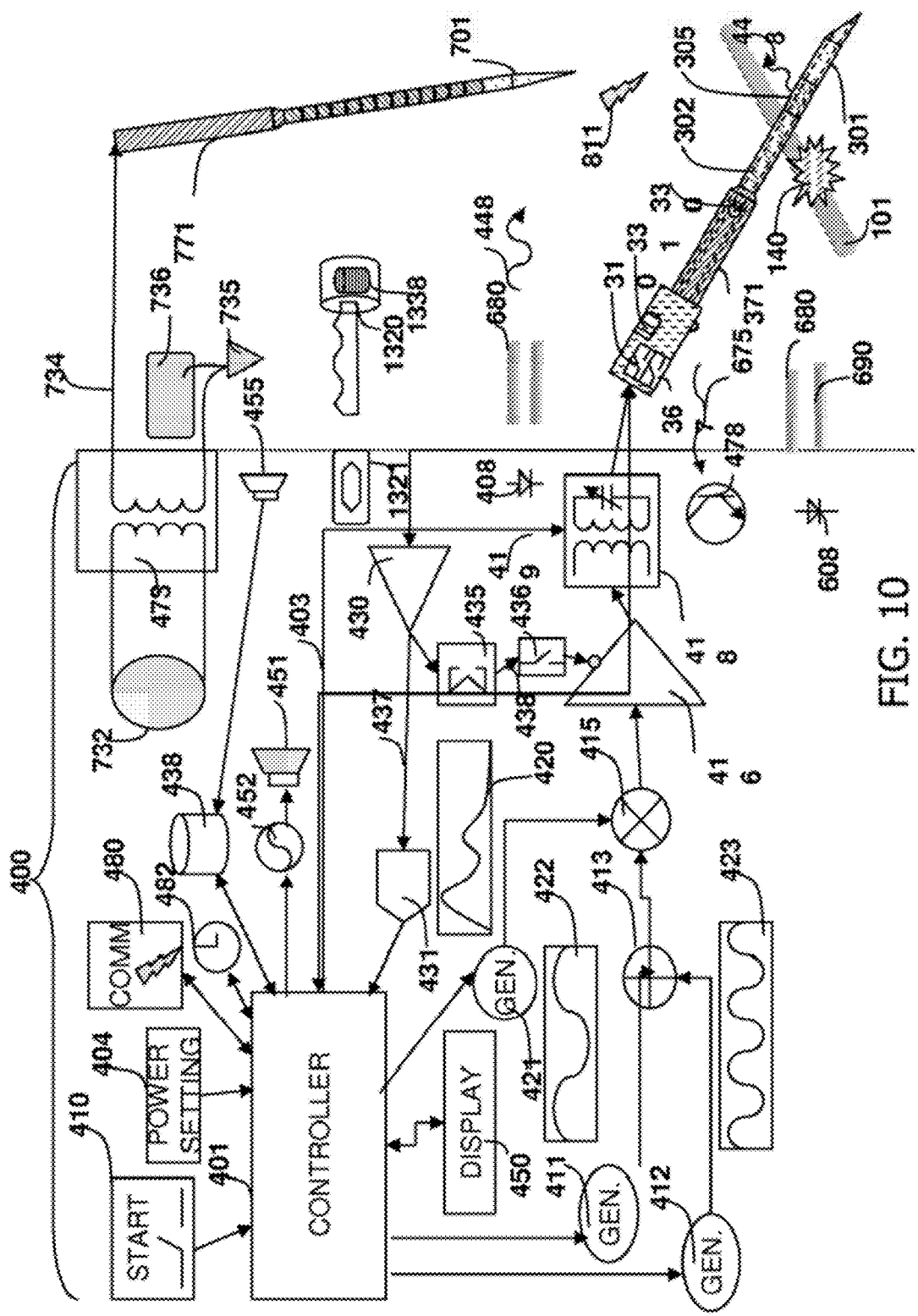
FIG. 10 Schematic diagram of the bi-polar driver system.

Hollow Electrode 301 often used as a syringe to deliver medication such as local anesthetic. Tip electrode 301 is connected to power amplifier 416 via impedance matching network 418 (FIG. 10). Return electrode(s) 302 delivers return current to power amplifier 416 via impedance matching network 418. Dielectric insulator in the disclosed embodiment is a transparent medical grade polycarbonate acting as a light pipe or fiber optic cable. Light source LED or laser 408 (FIG. 10) provides illumination at the far end of the probe via fiber optic cable/transparent dielectric 305 for guiding the probe under the skin i.e. shallow procedures. In an alternate embodiment dielectric insulator is replaced with a plurality of optical fibers for viewing and illumination as taught in FIG. 12A.

Figure 12A:
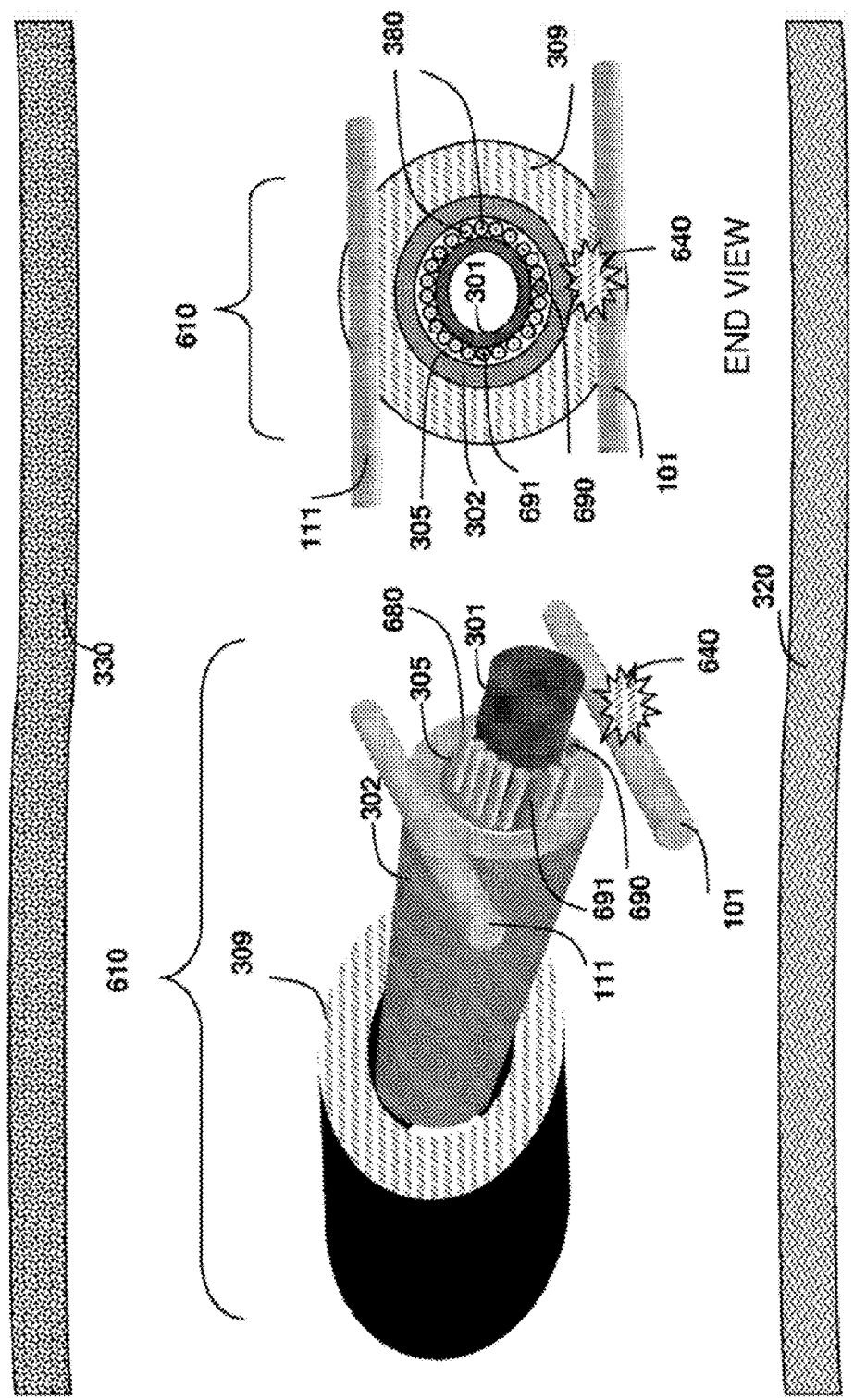
FIG. 12A. Side view Hybrid bi-polar needle for nerve ablation.
Figure 12B:
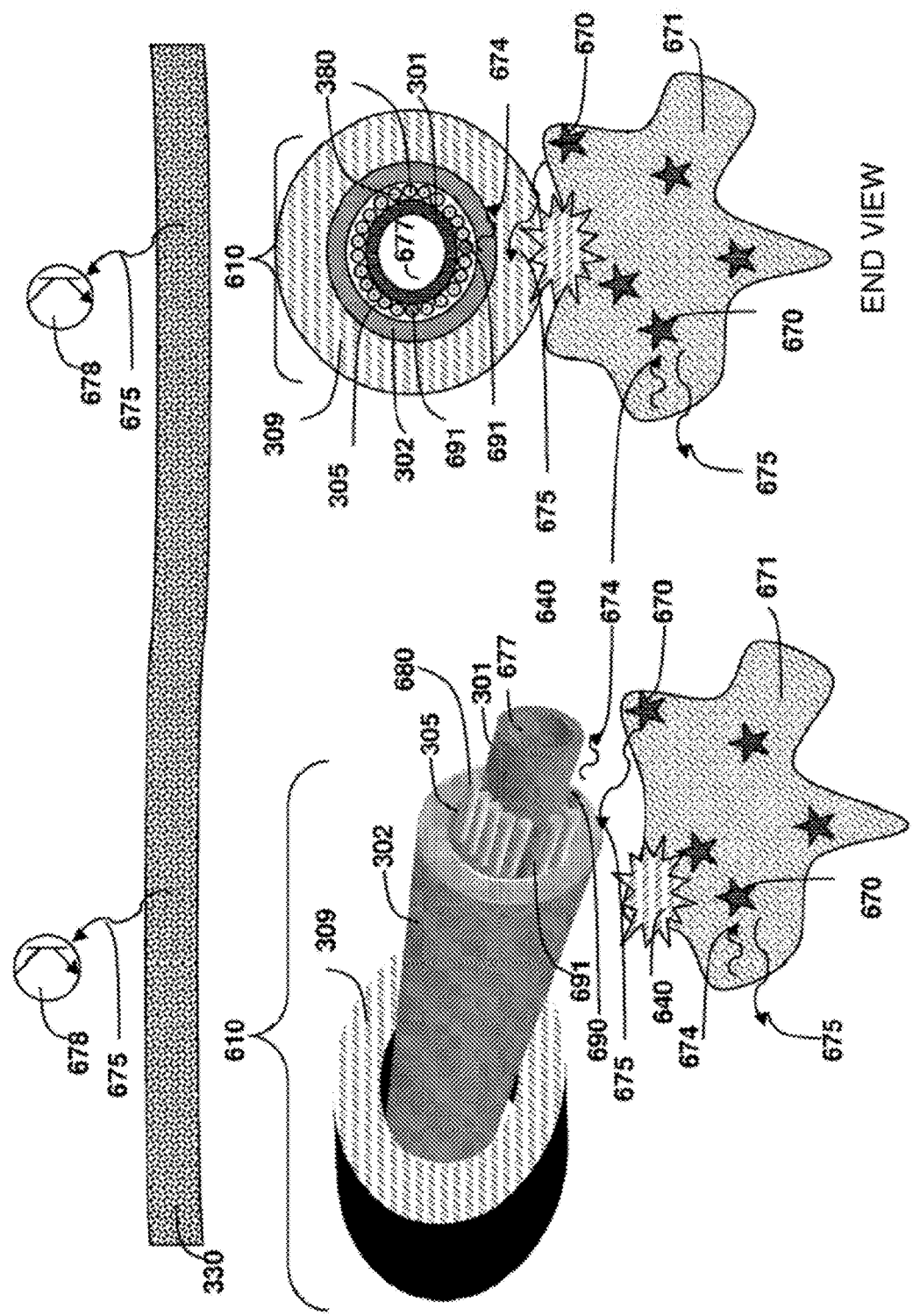
FIG. 12B Side view Hybrid bi-polar needle for tumor ablation.

Ablation regions 306 and 140 extend radially about electrode 301 generally following electric field lines. For procedures very close to skin 330 a chance of burning exists in region 306. To minimize the chance of burning, a split return electrode probe 374 in FIG. 9D is offered. Thereby concentrating the current away from region 306 to 140 or vice versa. In FIG. 8A, insulator 307 splits the return electrode into two sections 302 and 303, dividing return current ratio from 0-50%, which may also be selectively activated. Active electrodes are also split into two sections 301 and 311 so energy may be directed in a desired direction. This electrode configuration is identified on the proximal portion of the probe so the operator may position the needle and electrodes accordingly. FIG. 12A teaches a laser directed ablation for more precise energy delivery.

FIG. 8A Isometric View of Split Bi-Polar Probe.

The bi-polar probe 380 (not drawn to scale) consists of an insulating dielectric body 309 made from a suitable biologically inert material, such as Teflon PTFE or other electrical insulation, that covers split return electrodes 302 and 303. The disclosed conductive return electrodes 302 and 303 are fabricated from medical grade stainless steel, titanium or other electrically conductive material. Hollow or solid split conductive tip electrodes 301 and 311 protrude from the surrounding dielectric insulator 305. The operation of the hollow/split conductive tip is very similar to probe tip 310 as taught in FIG. 9D. Ablation regions 1203 (FIG. 10) and 140-144 extend radially about electrode 301 generally following electric field lines. For procedures very close to skin 330 a chance of burning exists in region 306. To minimize chance of burning a split return electrode probe 311 is used, thereby concentrating the current away from region 306 to 140. For procedures where there is a risk to nearby structures 111, the ablation region 1203 must be a non-radial ablation zone. The disclosed split electrode 380 permits dividing or splitting energy delivered to electrode pairs 301/302 and 311/303. The disclosed division or ratio between pairs is 0-100%. Dual amplifiers or time multiplexing/switching main amplifier, 416 located between electrode pairs, directs energy to target 101 avoiding 111. This simple switch network reliably ratios electrical energy while minimizing damage to nearby structures.

FIG. 9A Conical Bi-Polar Needle

Bi-polar probe 371 discloses conical shaped electrode 301 and tip 351 for minimally invasive single point entry. Probe diameter 358 is similar to a 20-gage or other small gauge syringe needle, but may be larger or smaller depending on the application, surface area required and depth of penetration necessary. In disclosed embodiment, electrode shaft 302 is 30 mm long with approximately 5 mm not insulated. Lengths and surface areas of both may be modified to meet various applications such as in cosmetic surgery or in elimination of back pain. The conductive return electrode 302 is fabricated from medical grade stainless steel, titanium or other conductive material. The dielectric insulator 305 in the disclosed embodiment is a transparent medical grade material such as polycarbonate, which may double as a light pipe or fiber optic cable. The high intensity light source 408 LED/laser (FIG. 10) provides guidance Illumination 448 at working end of probe. The illumination source modulation/flash rate is proportional to the received stimulation current 810 as taught in FIG. 8. A small diameter electrode permits a minimally invasive procedure that is typically performed with local anesthetic. This configuration may contain lumens for delivery of agents as described elsewhere.

FIG. 9B Hollow Chisel

The hollow chisel electrode 352 is often used as a syringe to deliver medication such as local anesthetic, medications, tracer dye. The hollow electrode may also extract a sample. Dielectric insulator 305 in the disclosed embodiment is a transparent medical grade polycarbonate and performs as a light pipe or fiber optic cable. The novel dual-purpose dielectric reduces probe diameter and manufacturing costs. Light source 408, typically a LED or laser (FIG. 10 not shown), provides Illumination 448 at the working end of probe. It provides an illumination source for guiding the probe under the skin. A second embodiment, as taught in FIG. 12A, dielectric insulator is replaced/combined with plurality of optical fibers for viewing/illumination.

FIG. 9C Tapered Conical

The bi-polar probe 373 discloses a tapered conical shaped probe for minimally invasive single point entry. It is constructed similarly to probe 371 as taught in FIG. 3A. Probe tip is not drawn to scale to teach the tip geometry. In disclosed embodiment, electrode 301 is approximately 5 mm long and fabricated from medical grade stainless steel but may be of various lengths to accommodate specific application and surface area requirements. The solid tapered conductive tip electrode 353 protrudes from tapered dielectric insulator 305. Transparent dielectric insulator 305 also performs as light pipe or fiber optic cable terminated to high intensity light source 408 (FIG. 7) providing illumination 448. The electrode assembly is mounted in an ergonomic handle 388 (which has not been drawn to scale). Handle 388 holds ablation on/off switch 310, ablation/stimulation mode switch 367, identification module 331 and terminations for cable 1334 (FIG. 73). Temperature sensor 330 (located close to tip) monitors tissue temperature.

FIG. 9D Split Conical Bi-Polar Probe

Description of this probe is described in both drawings 8B and 9D. Bi-polar probe 374 (not drawn to scale) consists of insulating dielectric body 309 made from a suitable biologically inert material, such as Teflon, that covers split return electrodes 302 and 303. Conductive return electrodes 302 are fabricated from medical grade stainless steel, titanium or other suitable conductive material. Hollow or solid split conductive tip electrodes 301 and 311 protrude from surrounding dielectric insulator 305. Their operation is very similar to probe tip 380 as taught in FIG. 8A. Solid tapered conductive tip electrodes 311 and 301 protrude from transparent dielectric insulator 305. Dielectric insulator 305 also performs as a light pipe or fiber optic cable terminated to high intensity light source 408 providing illumination 448.

Probe handle (not drawn to scale) encloses memory module 331, on/off switch 310 and mode switch 367. Temperature sensor 330 (located close to tip) monitors tissue temperature. Split electrode 380 (FIG. 8A) permits dividing or splitting energy delivered to electrode pairs 301/302 and 311/303. Dual amplifiers or time multiplexing/switching main amplifier 416 are located between electrode pairs directing energy to target 101 avoiding 111 creating asymmetric ablation volume. A small diameter electrode needle is injected from a single point of entry minimizing scaring and simplifying precise electrode placement.

Connections consist of a tapered dielectric sleeve 309 covering the ridged stainless electrode tube 302. Insulating sleeve 309 is made from a suitable biologically inert material, which covers electrode 302. Dielectric 305 insulates conical tipped electrodes 351 and 301.

Figure 11A:
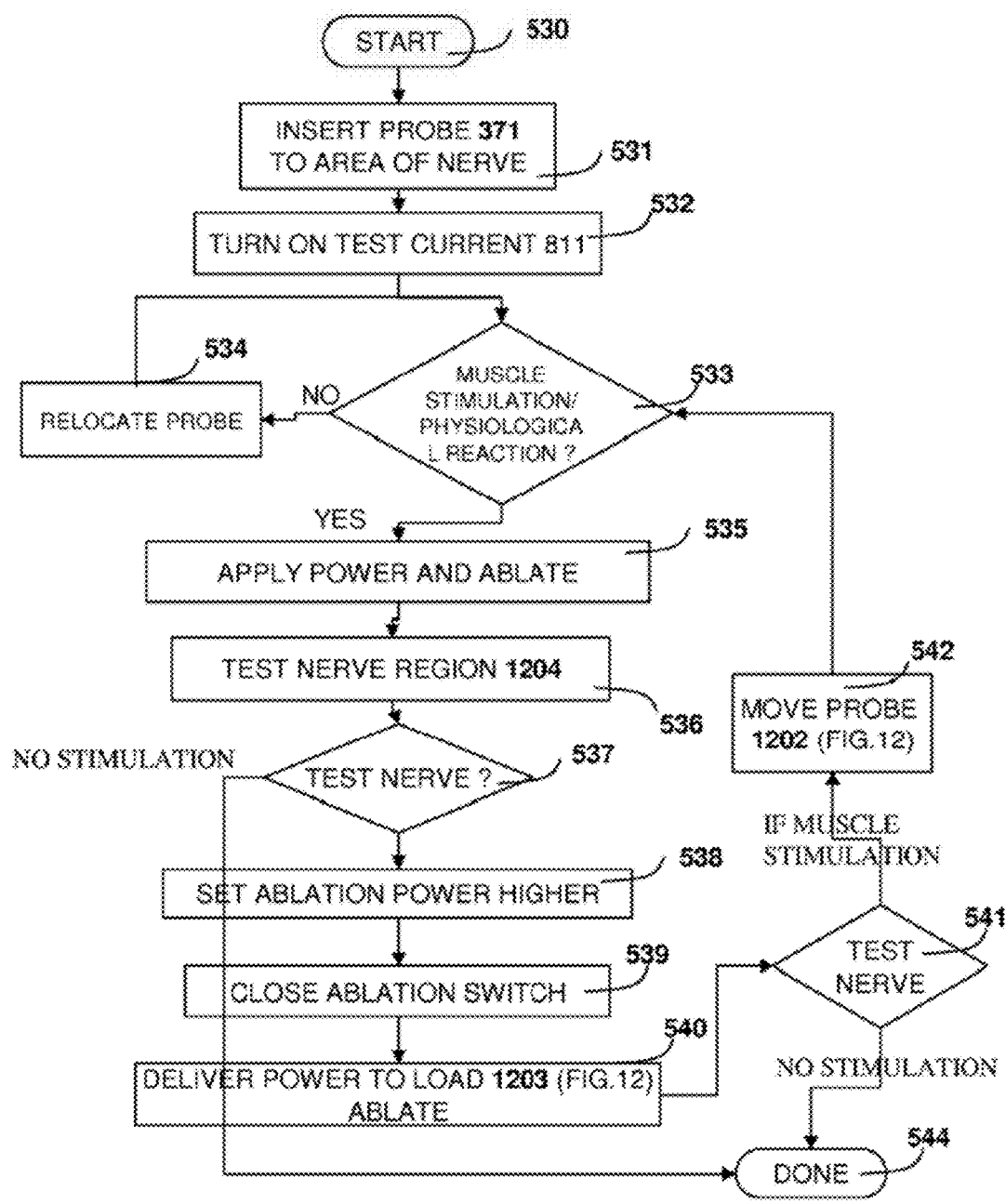
FIG. 11A Ablation Procedure without Auxiliary probe.

FIG. 11A Ablation Procedure (without Auxiliary Probes)

Ablation probe 371 is inserted and directed anatomically into the area where the target nerve to be ablated (Box 531) is located. Test current 811 is applied (Box 532). If probe is located in the immediate proximity of the target nerve a physiological reaction will be detected/observed (Example: During elimination of glabellar furrowing, muscle stimulation of the forehead will be observed). If reaction is observed, then a mark may optionally be applied on the surface of the skin to locate the area of the nerve. Power is applied (Box 535) in an attempt to ablate the nerve. If physiological reaction is not observed, (Box 534) the probe will be relocated closer to the target nerve and the stimulation test will be repeated (Box 536 & 537). If no physiological reaction is observed, the procedure may be terminated (Box 544). Also, the probe may be moved in any direction, up, down, near, far, circular, in a pattern, etc. to create a larger area of ablation for a more permanent result.

In Box 537, if stimulation is observed again, then the ablation power may be set higher (Box 538), alternatively, as mentioned, the needle may be moved in various directions, or a larger dosage of energy may be reapplied, to form a larger area of ablation for more effective or permanent termination of signal conduction through the nerve. After delivery of power (Box 540), stimulation energy may be applied again (Box 541). If there is no stimulation, the procedure is completed (Box 544). If there is still signal flow through the nerve (stimulation or physiological reaction) then the probe may be relocated (Box 542) and the procedure is started over again (Box 533).

Figure 11B:
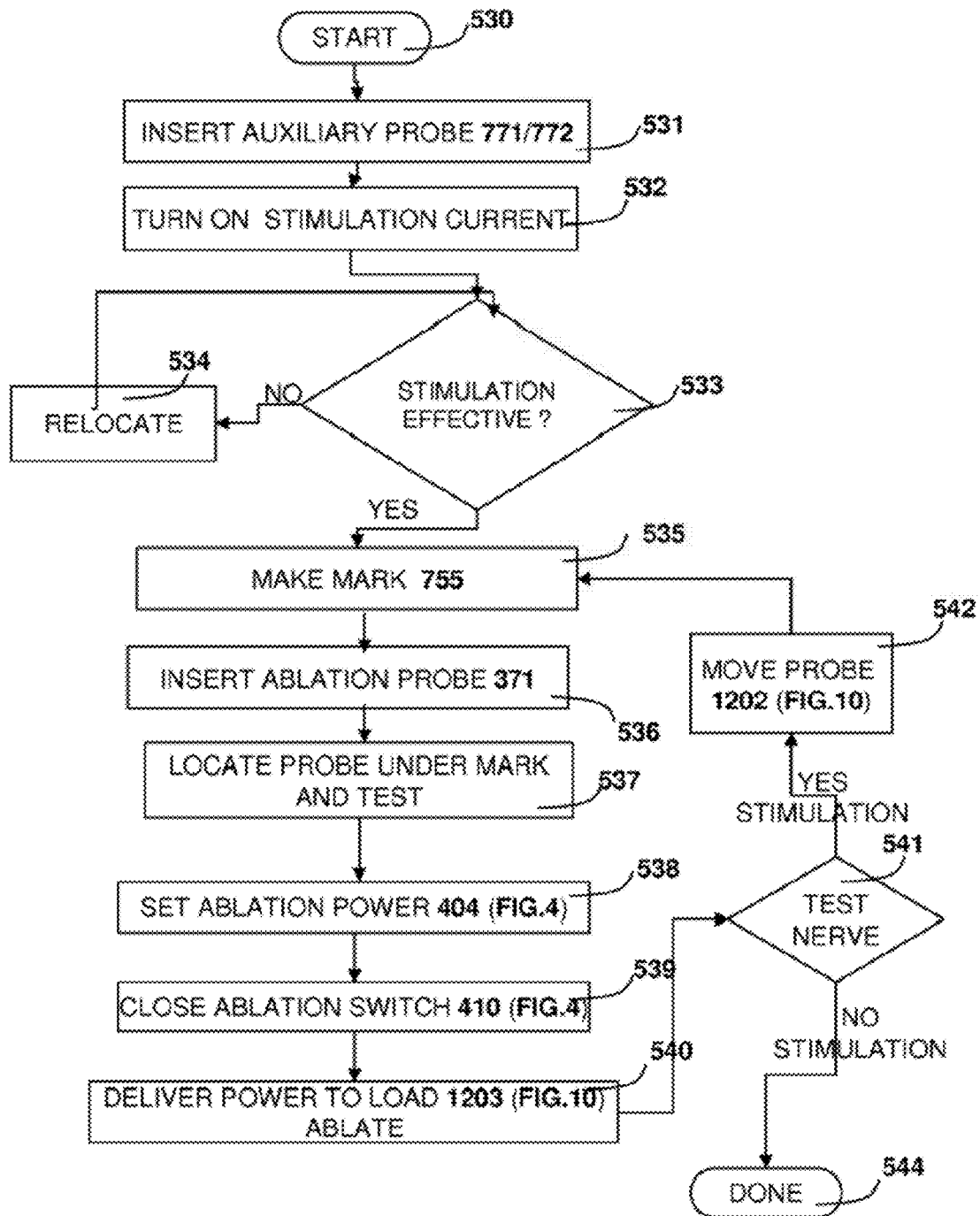
FIG. 11B Ablation Procedure with Auxiliary probe.

FIG. 11B Flow Chart of Visually Guided Ablation Procedure Using Auxiliary Probes Such as 771 and 772

Figure 13A:
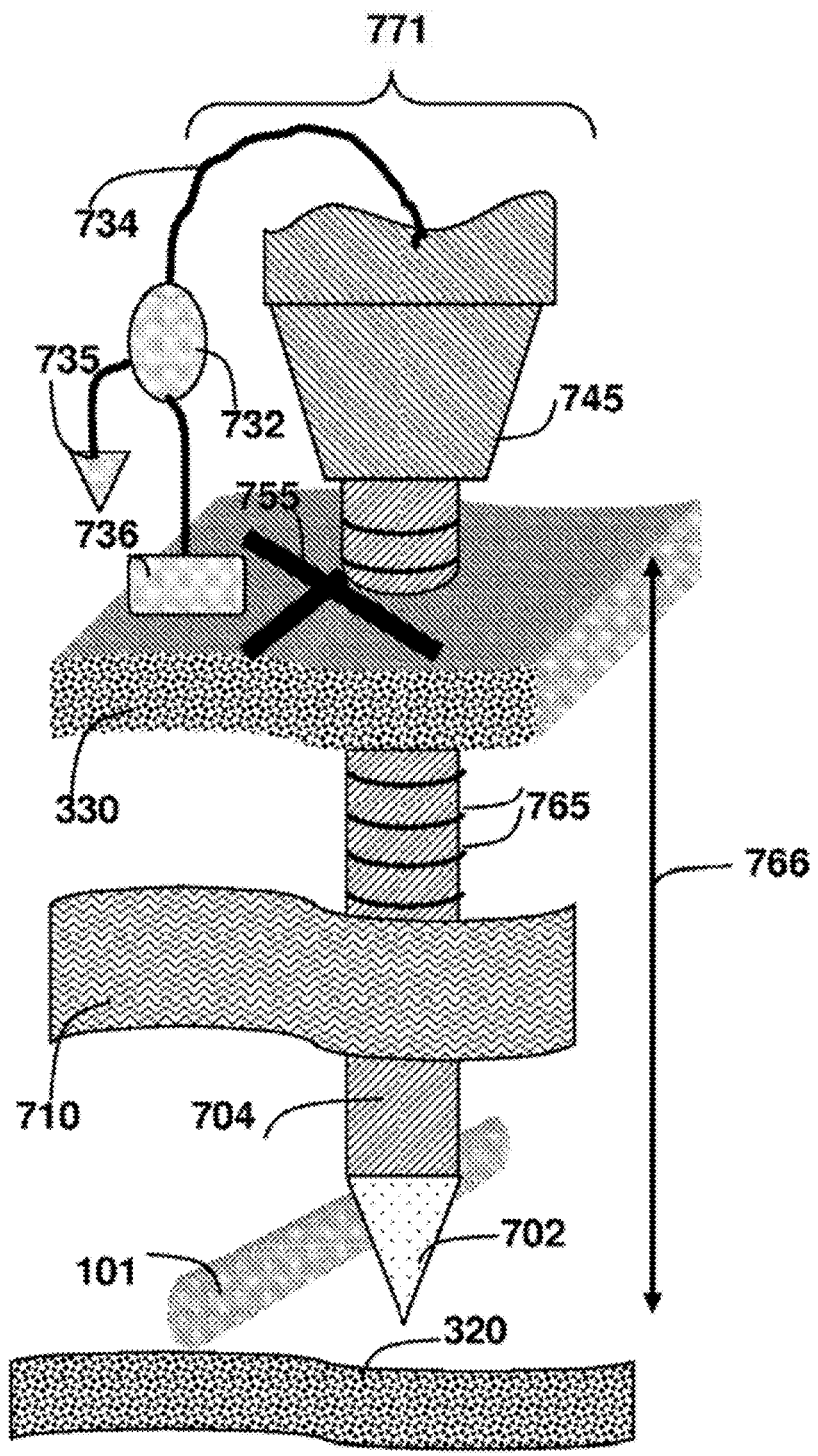
FIG. 13A Side view of auxiliary nerve probe.
Figure 13B:
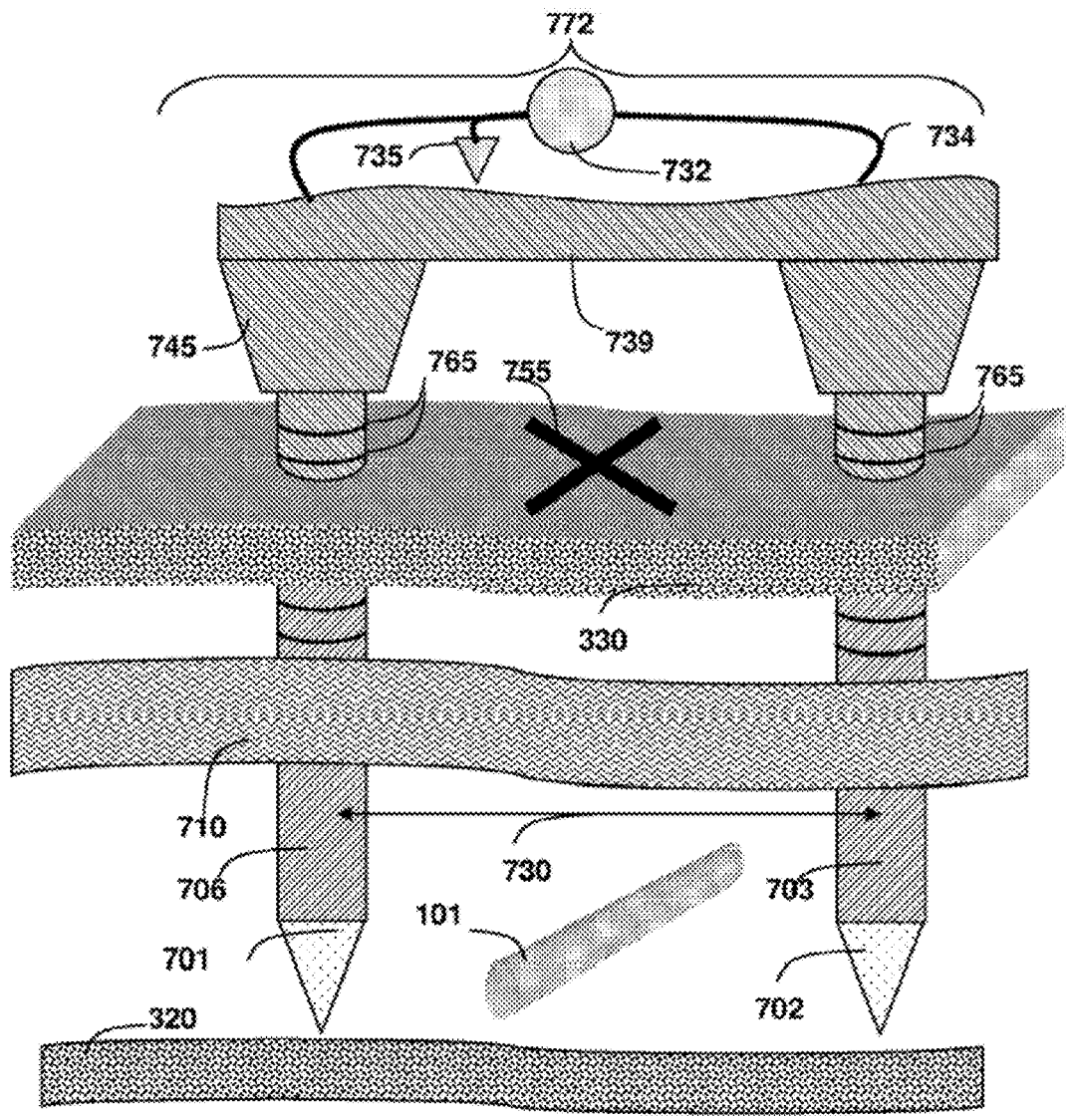
FIG. 13B Side view of auxiliary dual-tipped nerve probe.

Auxiliary probes 771 and 772 (FIGS. 13A and 13B) provide a method to quickly and accurately locate target structure 101 and subsequently mark target location 755. Auxiliary probes may be much smaller (like acupuncture needles) than ablation probes. Structures are marked typically with an ink or similar pen allowing the illuminated ablation probe 371 or other ablation probe to be quickly guided to mark 755. Optionally, non-illuminated probes may be used allowing the practitioner to simply feel for the probe tip. For deep structures, probe 771 (FIG. 8) us employed as an electronic beacon. Small current 811, which is similar to the stimulation current but smaller, from probe tip 702 is used to guide ablation probe 372 (FIG. 8).

Operation 530 (FIG. 11B) inserts auxiliary probe 771 or 772 (FIGS. 13A and 13B) thru skin 330 and muscle layer(s) 710 near nerve 101. Target 101 depth 766 is measured (FIGS. 13A and 13B) using auxiliary probe markings 765. Decision 533 checks if the probe is in position if not adjustments are performed in 534. Operation 532 enables nerve simulation current 811. When muscle stimulation is obtained or physiological reaction is obtained, Auxiliary probe tip is in place. Depth may be noted by reading marks 765 and location marks 755 may be made in operation 535. With the probe in position under mark in operations 536 and 537, operation 538 sets power level 404 and closes ablation switch 410. Alternatively, stimulation may be applied directly from the ablation probe as taught elsewhere. Operation 540 and controller 401 set generator 411 (FIG. 7) frequencies, modulation 420 envelope and enables power amplifier 416 to deliver preset ablation energy. Region 1203 (FIG. 10) shows the general shape of the ablation region for conical tip 301 for example.

Between each ablation, procedure 540 (FIG. 11A) (nerve conduction) is tested in 541. Probe amplifier 416 delivers small nerve stimulation current 811 from electrode 301 or Auxiliary probe 771 or both. Based on the nerve conduction test 541 if the desired level of conduction is achieved the procedure is compete. Operation 542 moves the probe to the next position and repeats conduction test 541. If compete, the probe(s) is removed in operation 544. Number and ablation intensity/energy are set by the particular procedure and the desired permanence. The practitioner selects the procedure/ power level 404 (FIG. 7) and controller 401 compares the installed probe via identification 331 (FIG. 7) for compatibility with selected procedure. The practitioner is alerted if the installed probe is incompatible with selected power range 404.

As an example and not a limitation, five ablation regions (140, 141, 142, 143, and 144) are shown in FIG. 10. Ablation starts with area 144, then the probe is moved to 143 and so on to 140. Alternatively, movement may be during insertion, moved laterally, in a circular manner or other manner to enlarge the area of targeted nerve destruction. Nerve responses may be tested after each ablation allowing the practitioner to immediately check the level of nerve conduction. Probe position and power adjustments are made before applying additional ablations if required. Accurate probe location tools and methods taught herein permit use of minimal ablation energy thereby minimizing damage to non-target structures. This translates to reduced healing time and minimal patient discomfort. The instant invention gives the practitioner a new tool to perform a minimally invasive nerve conduction limiting procedure with the ability to select, temporary or permanent nerve conduction interruption with a new level of confidence. This new tool offers a low cost procedure performed typically in office or outpatient setting often taking less than one hour with local anesthetic. In contrast to prior art where surgical procedures require stitches and longer healing intervals with limited control of permanence (nerve re-growth).

Figure 14:
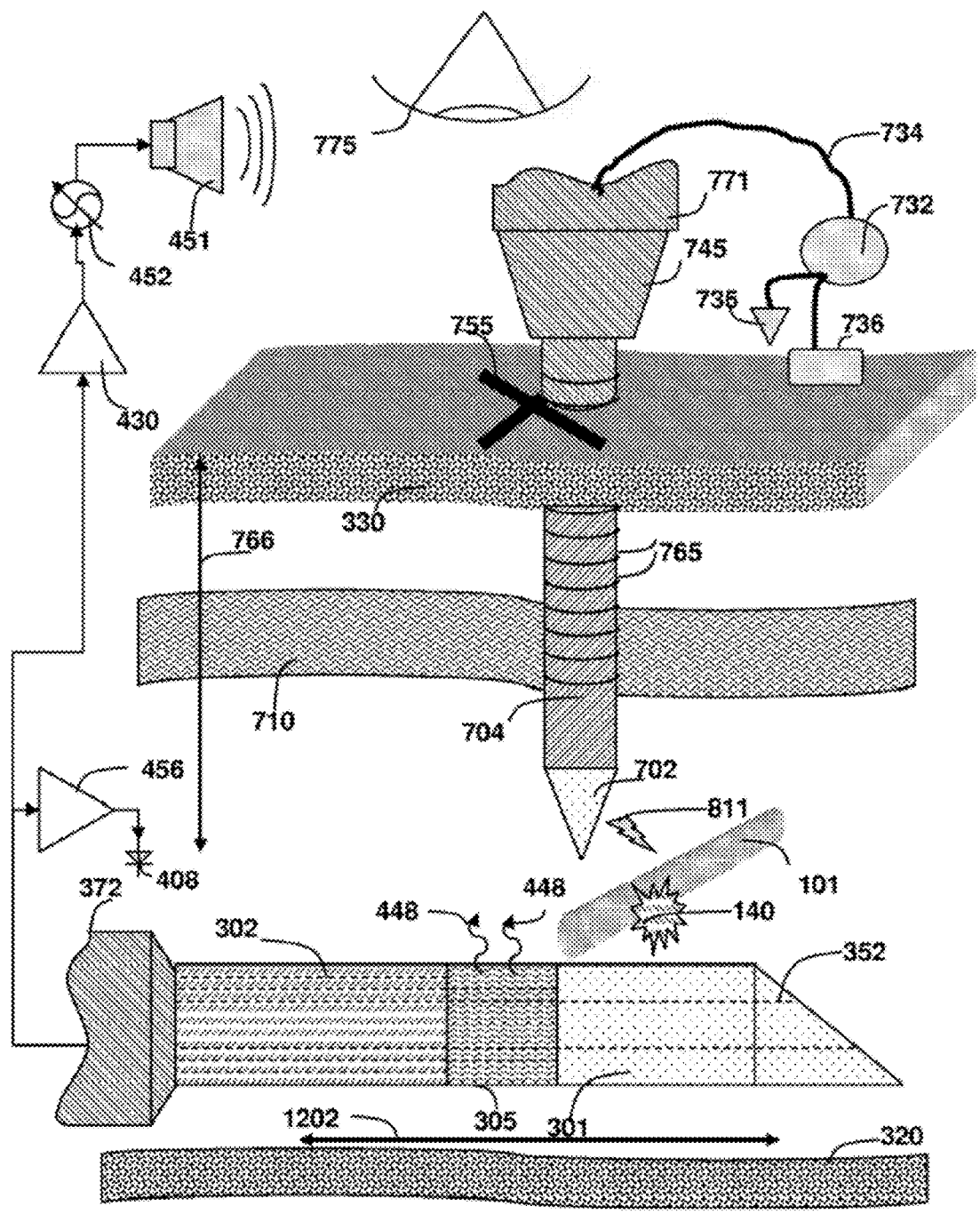
FIG. 14 Side view of guided ablation procedure with auxiliary nerve probe(s).

Auxiliary probes 771 and 772 (FIGS. 13A and 13BA) have accurately located target structure 101 and subsequently marked target locations 140 to 144. Shallow structures are marked typically with ink pen (755) allowing illuminated ablation probe 371, 372 or equivalent to be quickly guided to that point. For deep structures, probe 771 is employed as electronic beacon, small current 811 from probe tip 702 is used to guide ablation probe 372 as taught in FIG. 14.

Ablation probe 372 is inserted thru skin 330 and muscle layer(s) 710 near nerve 101. Illumination source 408 permits practitioner to quickly and accuracy guide illuminated 448 ablation probe 372 into position. Illumination 448 from ablation probe as seen by practitioner 775 is used as an additional aide in depth estimation. Selectable nerve simulation current 811 aids nerve 101 location within region 1204. This novel probe placement system gives practitioner confidence system is working correctly so s/he can concentrate on the delicate procedure. Accurate probe location permits use of minimal energy during ablation, minimizing damage to non-target structures and reducing healing time and patient discomfort.

Region 1203 shows the general shape of the ablation region for conical tip 301. Tip 301 is positioned in close proximity to target nerve 101. Ablation generally requires one or a series of localized ablations. Number and ablation intensity/energy are set by the particular procedure and the desired permanence.

Five ablation regions are illustrated 140, 141, 142, 143, and 144; however, there could be more or less regions. Ablation starts with area 144, then the probe is moved to 143 and so on to 140, conversely, ablations could start at 140 and progress to 144. Also, the practitioner could perform rotating motions, thus further increasing the areas of ablation and permanence of the procedure. Between each ablation procedure 540 (FIG. 5C), a small nerve stimulation test current 811 is emitted from electrode 301. The approximate effective range of the nerve stimulation current 811 is shown by 1204. Testing nerve response after each ablation allows the practitioner to immediately check level of nerve conduction. Without probe 372 removal, the practitioner receives immediate feedback as to the quality of the ablation. Then minor probe position adjustments are made before conducting additional ablations (if required).

FIG. 10 illustrates another example of a system for use with the methods and procedures described herein. First the probe electrode 301 is positioned in the desired location relative to the target nerve 101 (FIG. 10), then the user initiates the treatment via switch(es) 410 and 310 using the selected power setting 404 (FIG. 10). The controller configures the generators 411 (FIG. 10) and 412 to the amplitude frequency and modulation envelope, delivering 50 KHz-2.5 MHz of 5 to 500 watts of available energy. The summing junction 413 combines the RF outputs as the application requires and passes them to the pulse-width modulator 415 for output power control. The output of modulation generator 420 is applied to the multiplier 415 with radio frequency RF signals 422 and 423. This permits complex energy profiles to be delivered to a time variant non-linear biologic load. All of these settings are based on the information provide to the generator by the installed probe 371 the selected power 404 settings, and the modulation envelope 420 (FIG. 10) settings, which are then loaded by the generator 421.

Figure 15:
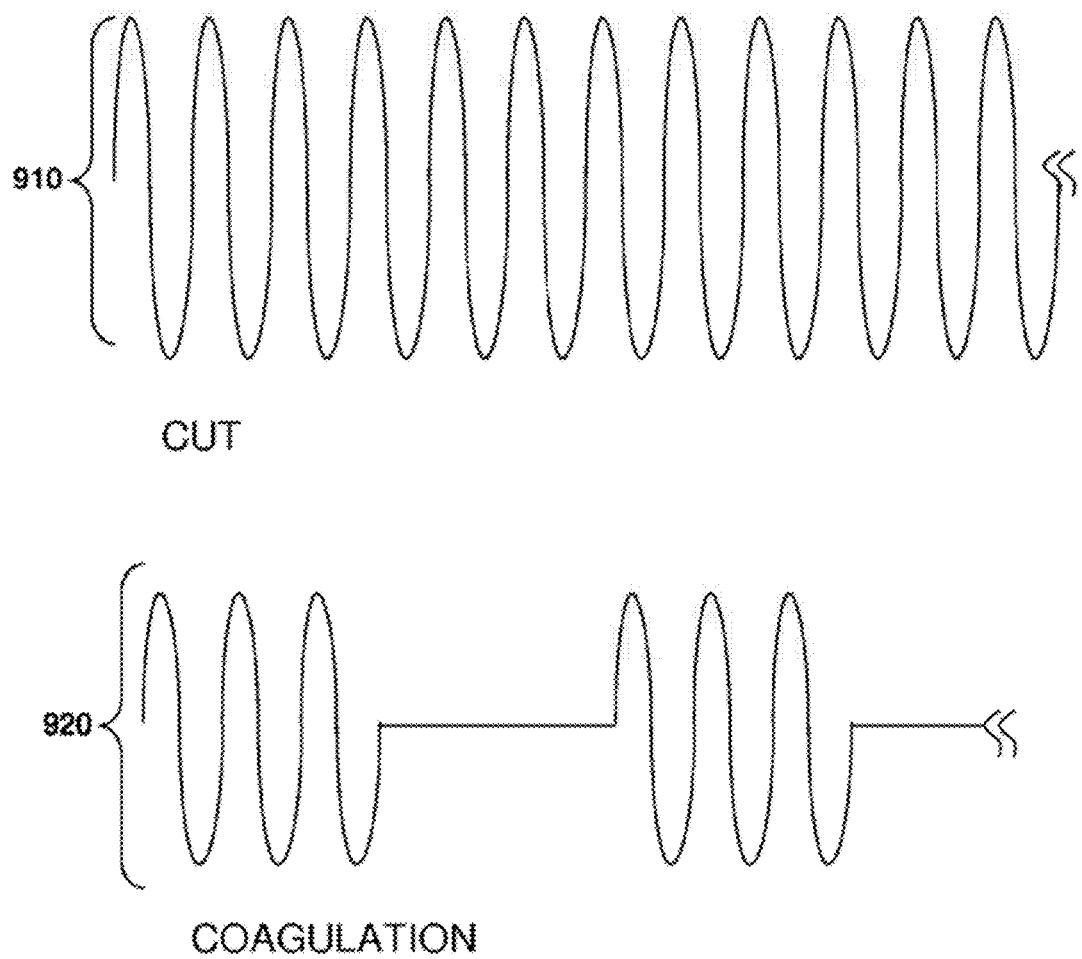
FIG. 15 Sample electro-surgery waveforms.

For example, both a high amplitude sine wave 910 (FIG. 15), used for cutting, and a pulse-width modulated (or PWM) sine wave 920, used for coagulation, are well known to electro-surgery art. Precise power rates and limits of average total power are controlled via integrator 435 minimizing damage to nearby structures or burning close to the skin for shallow procedures. Where nearby structures 11*l* (FIG. 8B) are too close to be avoided by electrodes such as 371 (FIG. 9A) and 372 (FIG. 9B), additional probe geometries as taught in herein offer additional methods to direct energy and limit ablation to a smaller region, thereby avoiding other structures. For safety a hardwired switch 436 disables the power amplifier in the event of a system fault, the probe is unplugged or over power condition, thus protecting both the patient and practitioner.

The output of the modulator 415 is applied to the input of the power amplifier 416 section. The power amplifier's 416 outputs are then feed into the impedance matching network 418, which provides dynamic controlled output to the biologic loads that are highly variable and non-linear, and require dynamic control of both power levels and impedance matching. The tuning of the matching network 418 is performed for optimal power transfer for the probe, power level, and treatment frequencies settled. The system's peak power is 500 watts for this disclosed embodiment. Precise control is established by the proximity of the tip and the control loops included in the generator itself. The final energy envelope 420 is delivered to probe tip 301 and return electrodes 302.

Directed Ablation

In addition to the substantial radially-symmetric ablation patterns with probes as taught in 371 (FIG. 9A) and 372, switching or dividing ablation power to multiple electrodes (FIG. 9D) can generate an asymmetric ablation zone. This high intensity source 608 with probe 610 (FIGS. 12A and 11B) minimizes damage to nearby structures 111 or the burning of skin 330 in shallow procedures. Also, FIGS. 8B and 9D identify probe configurations for selective or asymmetric ablation.

Power Feedback

Figure 16A:
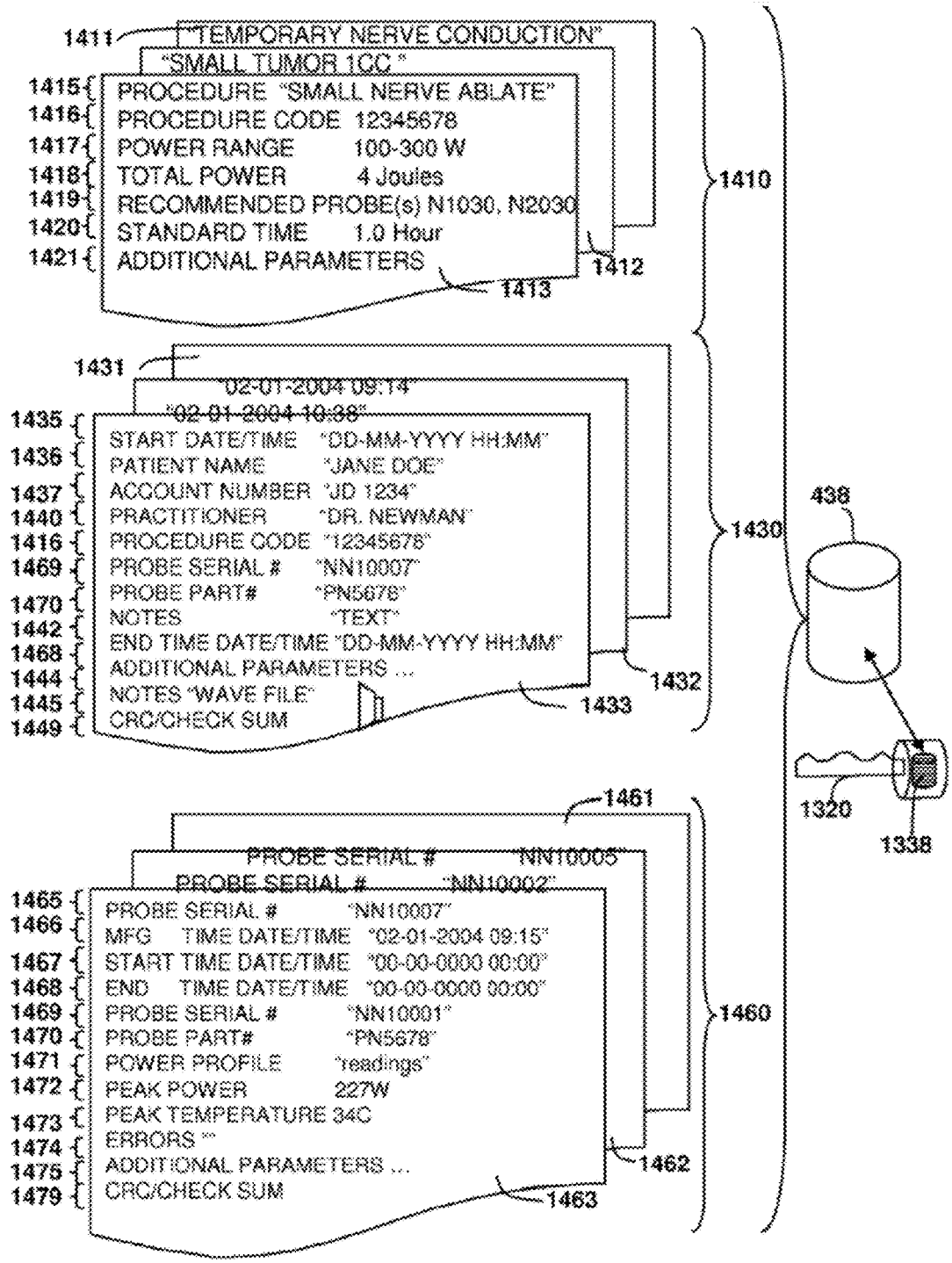
FIGS. 16A-16B Controller and probe data base structure.
Figure 16B:
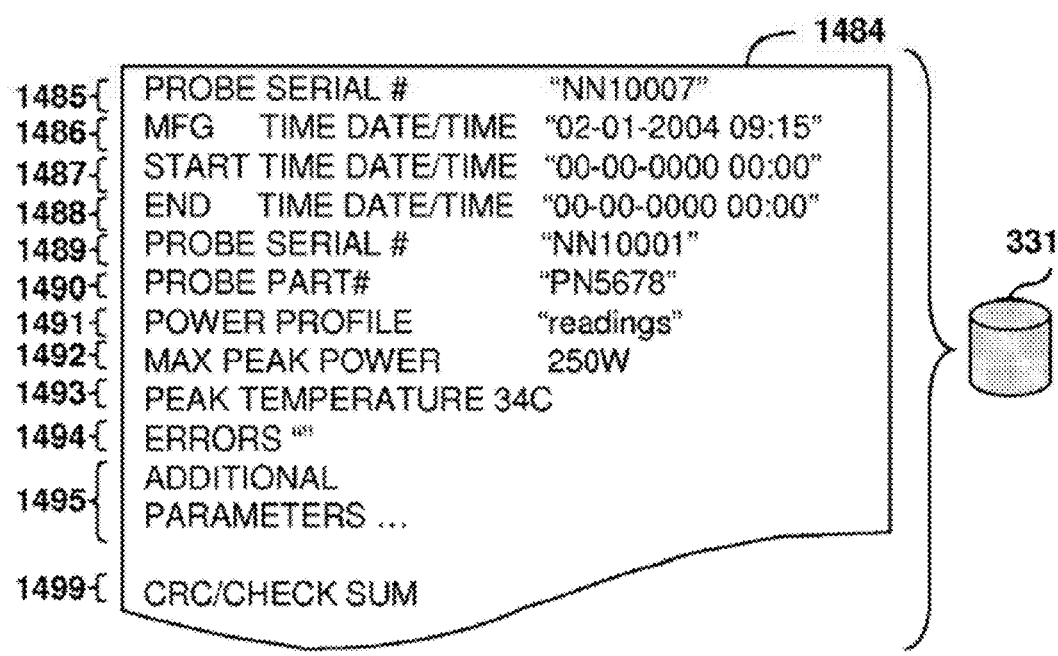

The power amplifier output 430 and buffered the feedback signals 437 can be connected to an Analog to Digital converter (or ADC) 431 for processor analysis and control. Said signals 437 control power modulation 420 settings and impact the impedance matching control signals 419. This integrated power signal 437 is recorded to the operating-condition database (FIG. 16A) for later procedure review. This power level is also compared to reading taken from the probe 1492 (FIG. 16B) as compared against procedure maximums, which if exceeded will in turn disable the amplifier output, thereby protecting the patient from error or equipment fault. Similarly, limits from the probe and generator sensors such as temperature 330 can optionally be used to terminate or substantially reduce the modulated power levels and ultimately the procedure.

The controllers described herein can also verify a selected procedure 1415 (FIG. 16A) for compatibility with installed probe. If incompatible, the user is also prompted to select a different power setting 404, procedure, or probe 371. If probe 371 matches power setting 404, the system enables power amplifier 416, guide light source 408, and low-voltage nerve simulation 732. Both of these procedures are enforced by a mandatory "hand shake" protocol and the serialized information, which must be present and properly verified by the electronic circuitry for a procedure to be instituted. During a clinical procedure, information is required to be conveyed by the embedded electronics contained within the probe, which provides another way of enforcing this protection and thus again preventing unauthorized re-use. The ultimate goal is prevent cross-contamination between patients. The probe will accomplish this by being unique, serialized, and given the above procedures. Once plugged in, the probe will enter the serial number into the data logging system via the serial bus 403 and circuit logic will thereafter prevent re-use of the probe and cross-contamination that would occur. Further, this scheme will prevent the use of unauthorized third party probes, for they will not be activated, preventing potential inferior or uncertified probes from being used and presenting potential danger to the patient.

Optical Probe Guidance

Figure 17:
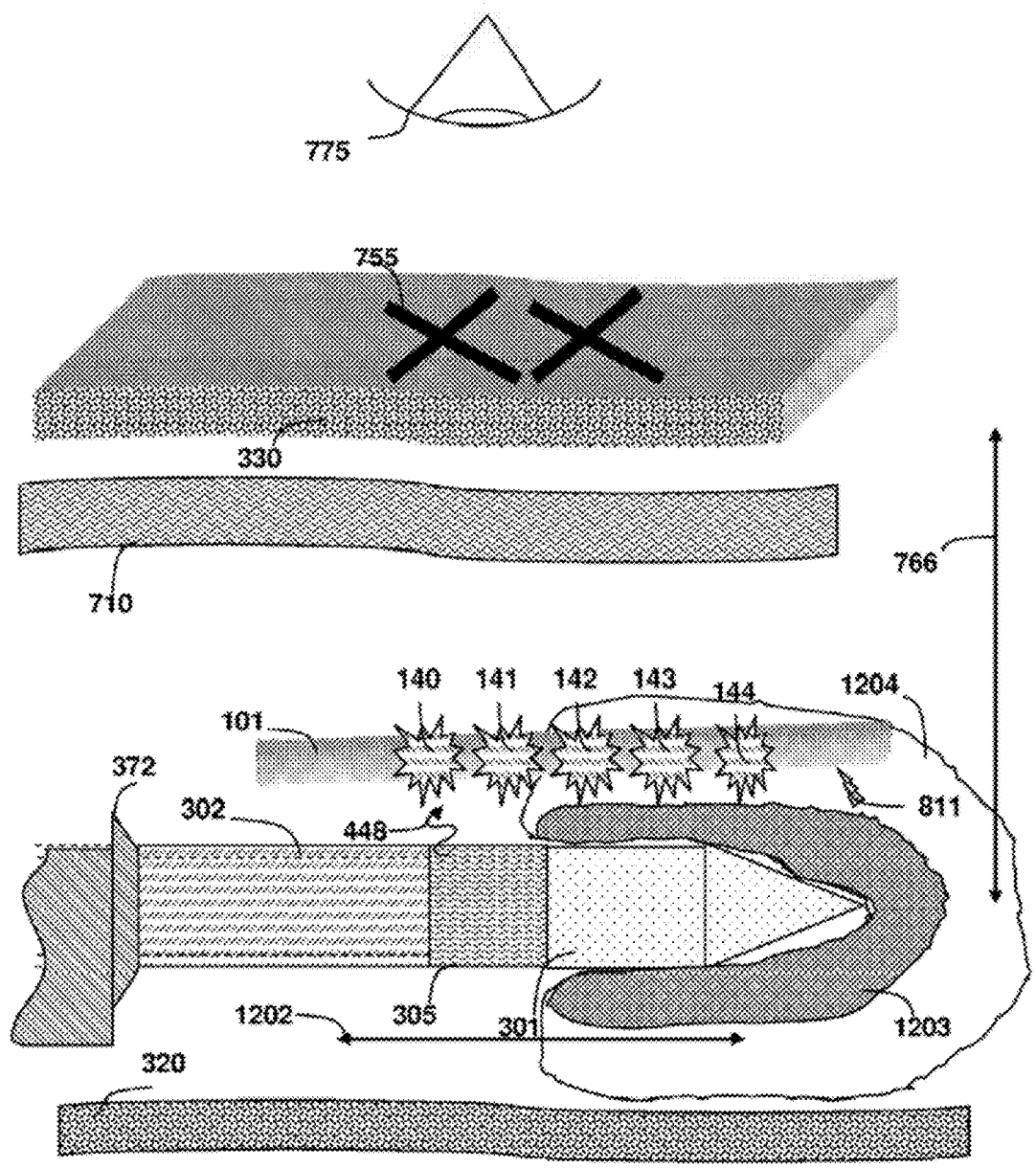
FIG. 17 Side view of visually guided ablation procedure.
Figure 19:
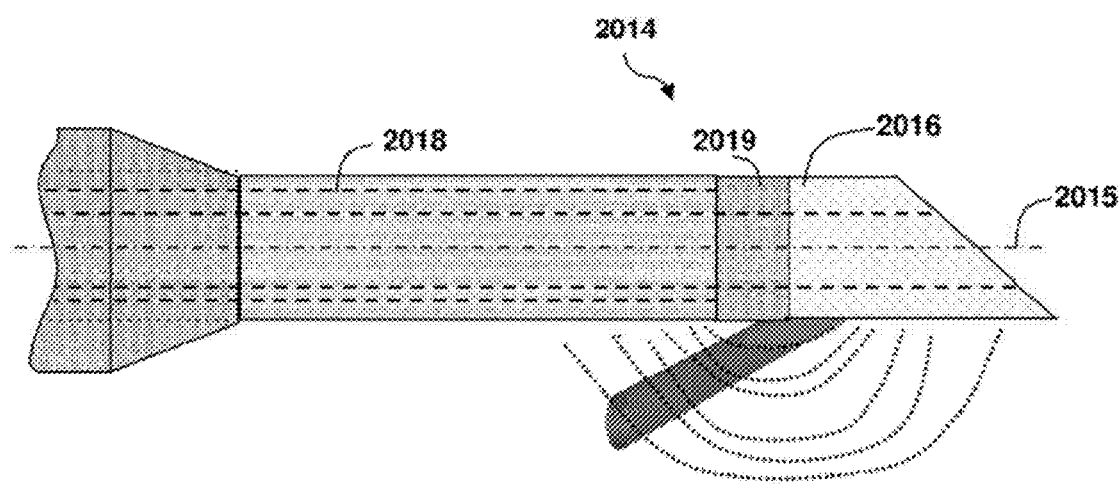
FIG. 19 is a side view of a single axis electrosurgical probe having two electrodes of differing surface areas.

Disclosed invention provides optical sources 408 that aid in probe placement (FIG. 17) by supplementing stimulation source 732 and acting as preliminary guide. Probe 771 is selectable between nerve stimulator or current 811 measurement and to or from the auxiliary probe tip 702. The ablation probe switch 367 selects low-energy stimulator/receiver or high-energy ablation to or from probe 371, 372, 373, and 374. In this mode, the physician operator will have previously placed marks 755 on the surface of the skin by various means described. The physician operator 775 will then see the tip when the 448 if the optical illumination is turned on. It 448 will provide a bright spot under the skin indicating the location of the tip in relation to the marks 755. The physician 775 will then guide the probe tip 301 into precise alignment under these marks 755 so as to enable ablation of that target tissue 101. Alternative Probe Configurations FIG. 19 is a schematic view of an alternative embodiment of a single axis electrosurgical probe 2000 having a longitudinal probe axis 2001, which is similar to the probes described above. However, probe 2000 of FIG. 19 features substantially equal surface area conductive electrodes 2002 and 2004 located along a longitudinal axis. A probe 371 also having substantially equal surface area electrodes 301 and 302 is shown in above.

In an equal electrode surface area implementation, one of the conductive electrodes 2002, 2004 may be selectively connected to a stimulation current source or an ablation current source as described above. The other electrode 2002, 2004 may be unconnected or connected as a ground or return path for the connected current source. In the embodiment shown in FIG. 19 conductive electrode 2002 is configured to be connected to the ablation source making electrode 2002 the active electrode. Thus electrode 2004 is in this embodiment a return electrode. Either electrode 2002, 2004 may be connected to a current source or return with appropriate switches.

Since electrodes 2002 and 2004 have substantially equal surface area, the local heating formed upon the application of RF ablation energy to the active electrode 2002 results in a heating zone having a substantially symmetrical ellipsoid form.

The single axis electrosurgical probe 2000 of FIG. 19 also features a dielectric insulator 2006 positioned along the probe axis between the conductive electrodes 2002 and 2004. The dielectric insulator 2006 may have any suitable length, and probes with alternative length insulators may be manufactured for specific ablation procedures. Varying the length of the dielectric insulator 2006 varies the gap dimension 2008 between the electrodes 2002 and 2004. Varying the gap dimension 2008 provides for optimization of the current density within the ablation zone, varies the length of the ablation zone and permits the use of higher voltages, if desired. Thus, the gap dimension may be selected in conjunction with other parameters such as electrode surface area and ablation current to achieve select ablation volumes and tissue temperatures for specific applications.

The probe 2000 of FIG. 19 also features a blunt tip 2010 rather than the conical tip 351, chiseled tip 352 or other tips of the probes described herein. The blunt tip 2010 of FIG. 19 has a smooth rounded profile and is advantageous in certain instances to allow the probe to be easily advanced and maneuvered under the skin minimizing the risk of puncture or the cutting of adjacent tissue or anatomical structures. Thus, a blunt tip 2010 may significantly reduce the bruising or other trauma associated with a procedure.

The probe 2000 of FIG. 19 may include a sensor 2012. The sensor may be a temperature sensor 2012. A temperature sensor provides for active temperature monitoring within the ablation zone. Alternatively, a single axis electrosurgical probe of any configuration may be implemented with a Kalman filter as taught by Conolly U.S. Pat. No. 6,384,384 which patent is incorporated herein by reference in its entirety. Kalman filters are also used to estimate tissue temperature within an ablation volume. Kalman filters are suitable for use where well-defined tissue state changes occur at specific temperatures due to protein denaturation such as the denaturation of collagen at 65 C. Kalman filter temperature monitoring is advantageous because the bulk and cost of a separate temperature sensor can be avoided.

Figure 20:
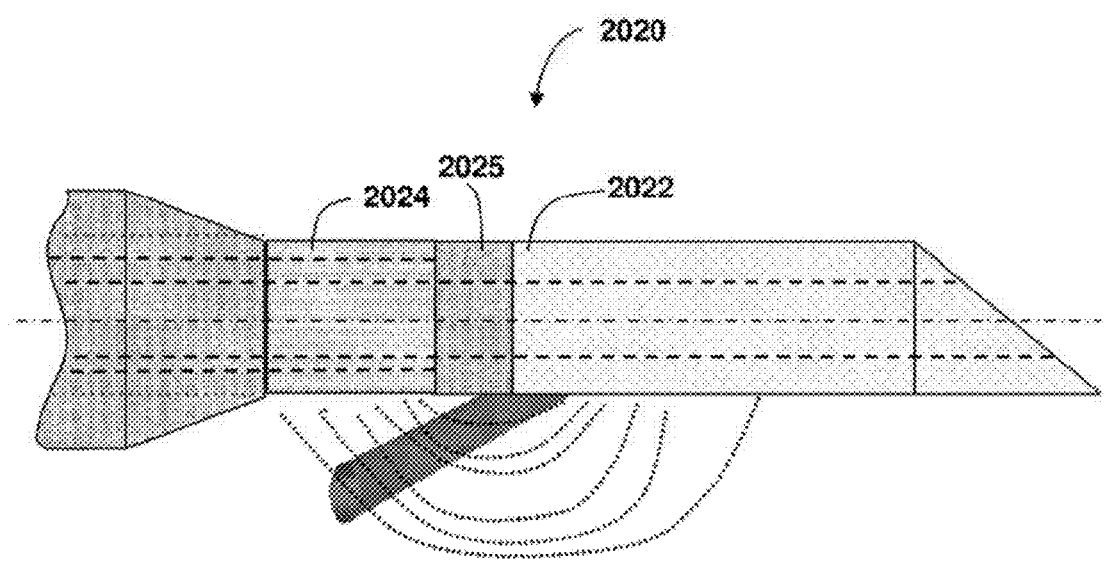
FIG. 20 is a side view of a single axis electrosurgical probe having two electrodes of differing surface areas.

FIG. 20 is a schematic view of an asymmetrical single axis probe 2014 also defining a longitudinal probe axis 2015. The probe 2014 features a first conductive electrode 2016 and a second conductive electrode 2018 having different surface areas. In the embodiment shown in FIG. 20, the first electrode 2016 is an active electrode and the second electrode 2018 having a larger surface area is a return electrode. A probe having any surface area ratio between an active and return electrode may be fabricated and used to achieve specific ablation results. In addition, the relative positions of the active electrode 2016 and the return electrode 2018 with respect to the tip of a given probe may be switched. In one embodiment the ratio of the active electrode 2016 to the surface area of the return electrode 2018 is 1:3. Other ratios including 1:8 may be implemented to achieve specific results. The surface area ratio may further be adjustable using a sleeve or other mechanism which will shield or cover a portion of on or both electrodes thus increasing or decreasing the length of the gap defining dielectric insulator 2019. Generally, asymmetrical electrode surface areas will result in asymmetrical heating and ablation because of the higher current density of the RF ablation energy at the electrode with smaller surface area. For example, upon the application of RF energy to the active electrode of the FIG. 20 embodiment, a tissue volume proximal the active electrode 2016 may be asymmetrically heated due to the greater current density resulting from the relatively small surface area of the active electrode 2016. Asymmetrical tissue heating coupled with precise RF power integration taught herein and various probe geometries permits the formation of selected repeatable and controlled ablation volumes.

Figure 21:
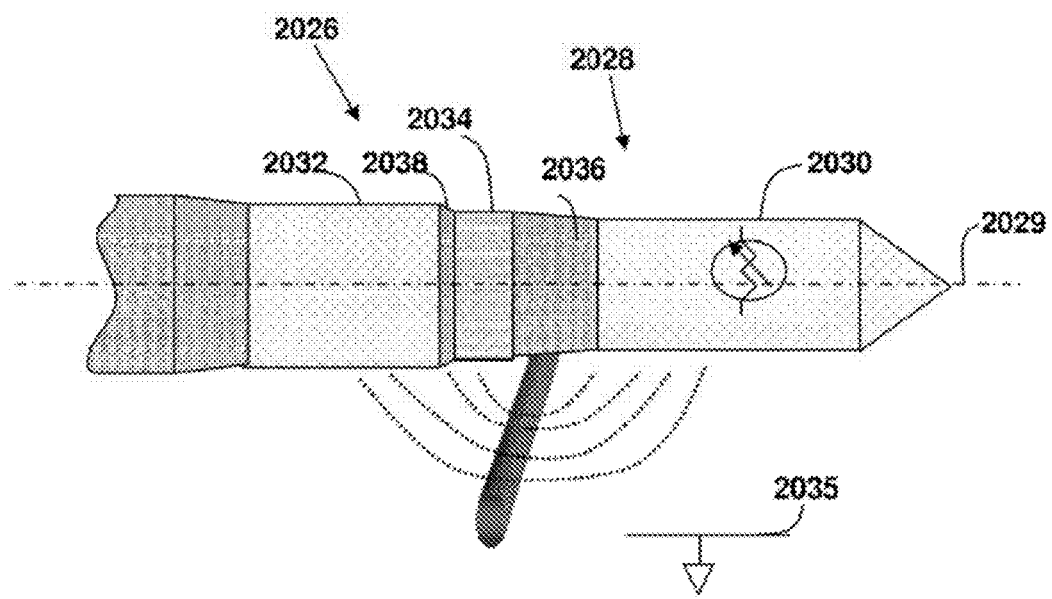
FIG. 21 is a side view of a single axis electrosurgical probe having three electrodes.

FIG. 21 schematically illustrates an alternative asymmetrical probe 2020, which is similar in many respects to the asymmetrical probe 2014 of FIG. 20. The asymmetrical probe 2020 of FIG. 21, however, features an active electrode 2022 having a surface area greater than that of the return electrode 2024. In the FIG. 21 embodiment current density is higher at the relatively smaller surface area electrode 2024, thus ablation energy is concentrated in the dielectric insulator gap 2025 between the electrodes 2022 and 2024 nearer return electrode 2024 and away from the tip of the probe.

Figure 22:
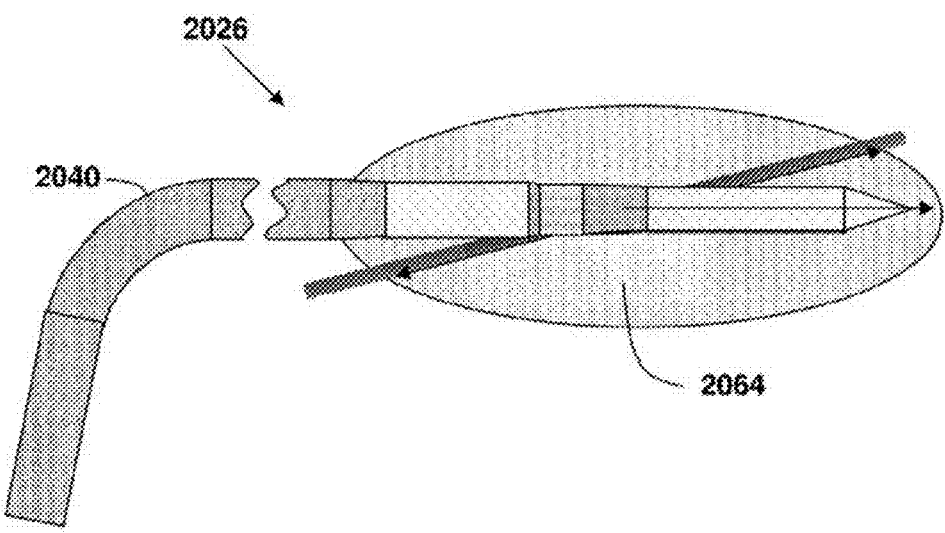
FIG. 22 is a side view of a single axis electrosurgical probe having three electrodes and a curved handle portion.
Figure 23:
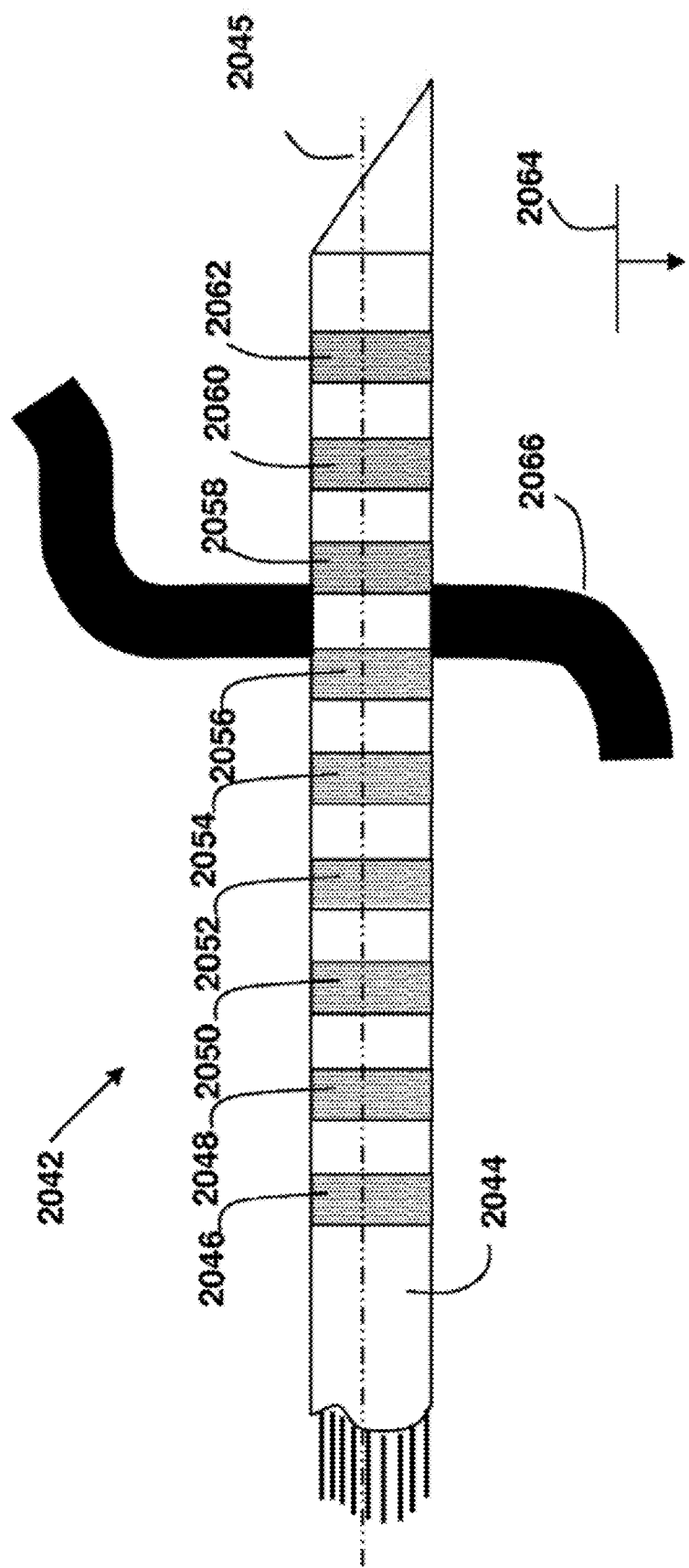
FIG. 23 is a side view of a single axis electrosurgical probe having multiple electrodes transverse a nerve.

FIG. 22 is a schematic view of one embodiment of a multiple electrode probe 2026. The multiple electrode probe 2026 includes a substantially needle-shaped probe body 2028 which defines a longitudinal probe axis 2029. More than two electrodes are associated with the probe body and positioned at various locations along the probe axis. In the FIG. 22 embodiment the electrodes include an active electrode 2030, a return electrode 2032, and a stimulation electrode 2034. In this embodiment the active electrode is positioned near the tip of the multiple electrode probe 2026, the return electrode 2032 is positioned away from the tip and the stimulation electrode 2034 is positioned between the active electrode 2030 and the return electrode 2032. It should be noted that the position of the various electrodes with respect to each other and the tip may be varied to achieve specific ablation and probe positioning advantages. In addition, the connection of any given physical electrode as an active electrode, return or stimulation electrode may be varied at the discretion of the user with a simple switching mechanism between the electrode and the ablation or stimulation energy sources. Alternatively, a separate ground or return path 2035 may be utilized with any configuration of electrodes. The various electrodes of the multiple electrode probe 2026 are separated by a first dielectric insulator 2036 and a second dielectric insulator 2038. FIG. 23 schematically illustrates the multipolar probe 2026 of FIG. 22 with the addition of a curved section 2040 opposite the portion of the probe body 2028 associated with the electrodes. The curved section 2040 may in certain instances allow the practitioner to achieve optimal probe positioning with a minimum of unnecessary tissue disruption. A multiple electrode probe 2026 may be implemented with dielectric insulators 2036, 2038 of varying dimensions, sensors or electrodes of different surface areas, all as described above, to achieve desired ablation results.

Figure 24:
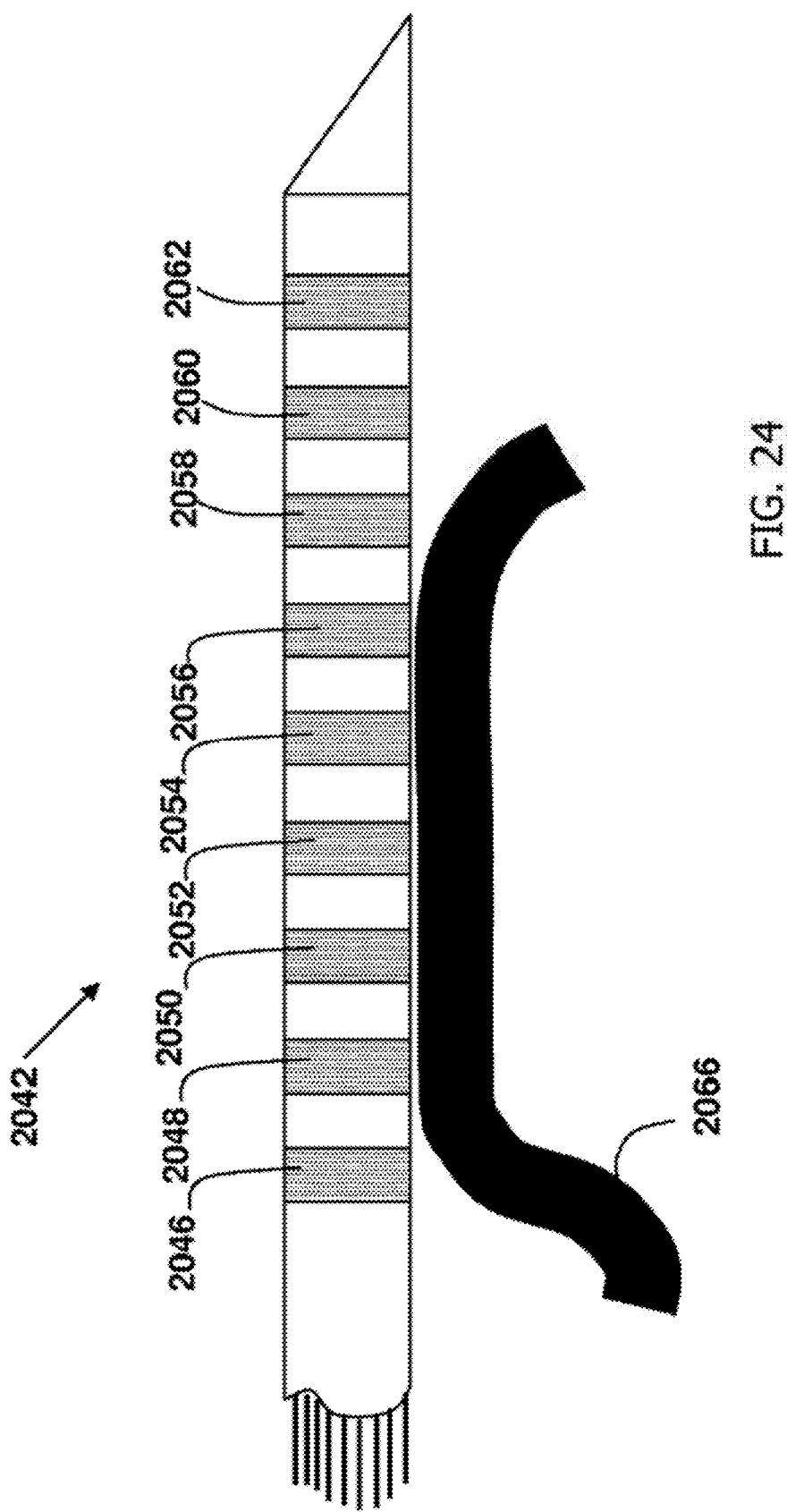
FIG. 24 is a side view of a single axis electrosurgical probe having multiple electrodes parallel to a nerve.
Figure 25:
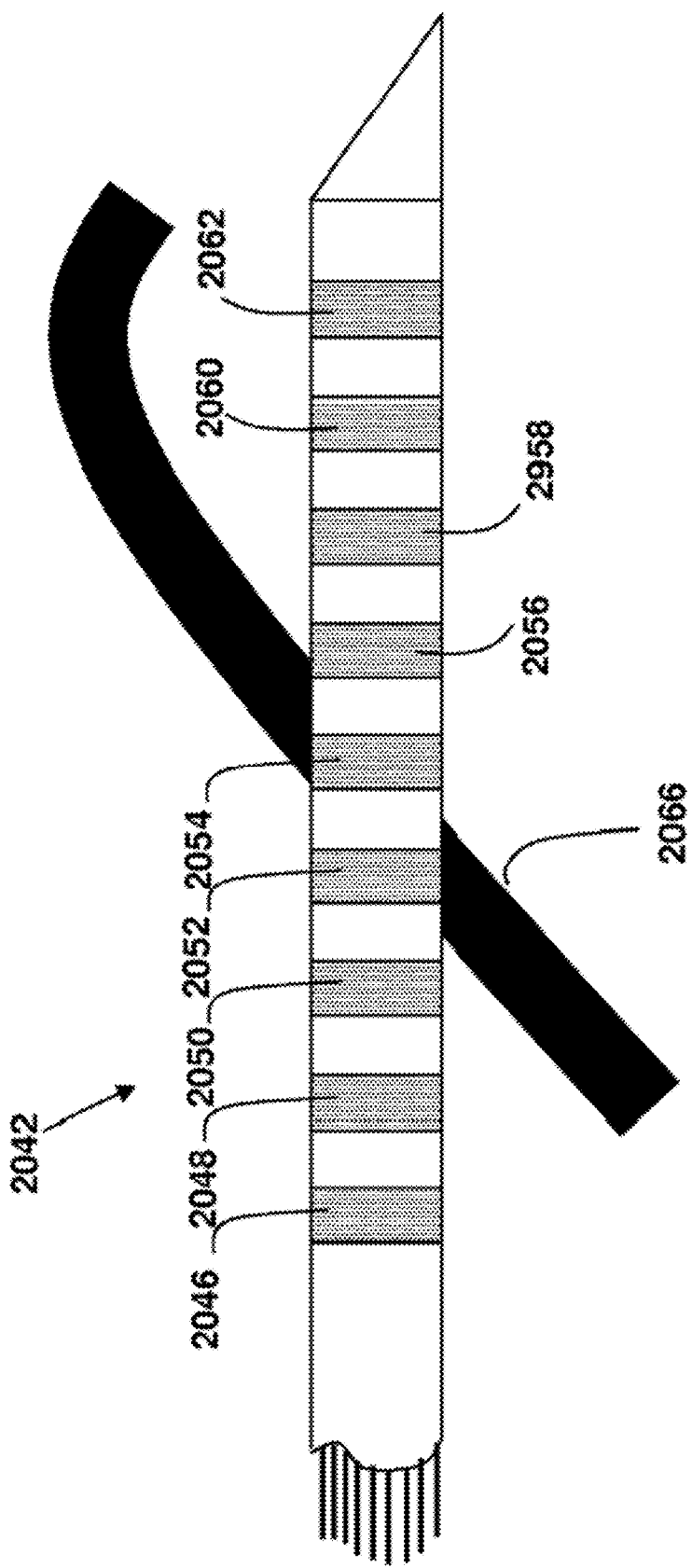
FIG. 25 is a side view of a single axis electrosurgical probe having multiple electrodes crossing a nerve at an angle.

FIG. 23-25 schematically illustrates an alternative embodiment of a multiple electrode probe 2042. The multiple electrode probe 2042 of FIG. 23-25 includes a probe body 2044 which defines a longitudinal probe axis 2045. Multiple electrodes 2046-2062 are associated with the probe body 2044 at separate locations along the probe axis. In the embodiment shown in FIG. 23-25 the electrodes are uniformly sized and spaced. It is important to note, however, that different sizes of electrodes and non-uniform spacing of the electrodes may be implemented to achieve specific ablation results. Preferably, each of the electrodes 2046-2062 may be selectively connected with one or more switches to a stimulation current source, an ablation current source, a ground for the stimulation current source a ground for an ablation energy source or left unconnected. As described in detail below, the flexibility provided by switched connection of each electrode to a current source or ground provides certain advantages in probe location and ablation. In addition, the multiple electrode probe 2042 could be deployed in conjunction with a separate return electrode 2064, typically placed in contact with tissue away from the ablation site.

Placement Methods

Several methods of properly positioning a probe adjacent to a selected nerve for ablation energy application are discussed above. For example, probe placement methods featuring florescence marker dyes, optical probe guidance and electronic probe guidance with the use of low energy nerve stimulation current are discussed in detail. Certain of the alternative probe configurations as illustrated in FIGS. 19-25 provide for refined probe placement methods using variations of the basic electrical stimulation techniques described above.

Figure 18:
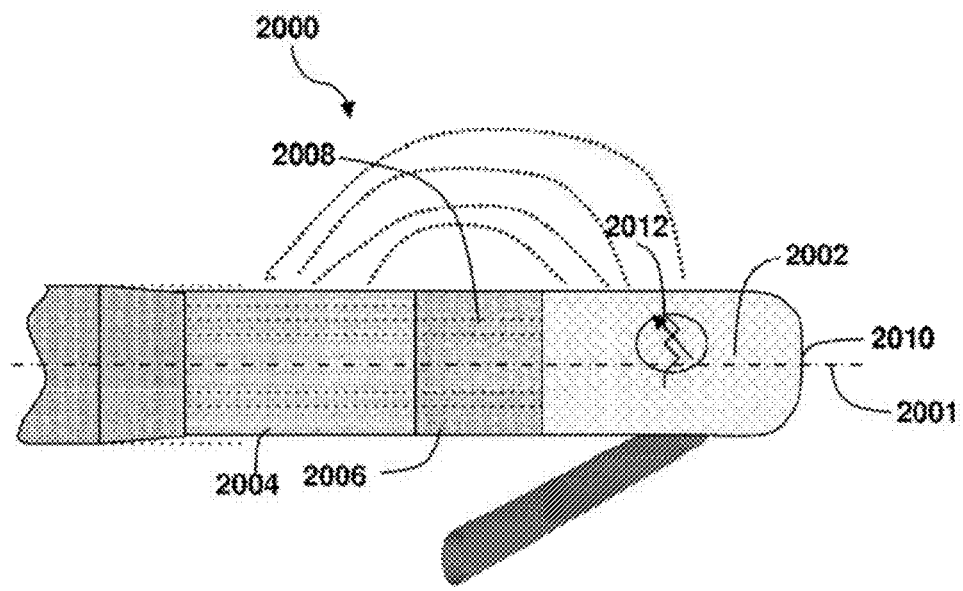
FIG. 18 is a side view of a single axis electrosurgical probe having equal surface area electrodes.

The single axis electrosurgical probe 2000 of FIG. 18 or the asymmetric probes 2014, 2020 described herein can each be properly positioned using an iterative technique, as described above with reference to FIGS. 11A-C. The iterative placement method may be refined for uses with multiple electrode probes such as are depicted in FIGS. 16-20.

In probe embodiments where the stimulation electrode is positioned in between the ablation electrodes 2030, 2032, the above described iterative method guarantees that the target nerve is positioned within an elliptical ablation zone 2064 (see FIG. 17) which will be formed between the active electrode 2030 and return electrode 2032 upon the application of RF ablation energy.

FIG. 23-25 shows an alternative embodiment of a multiple electrode probe 2042 placed in various orientations with respect to a target nerve 2066. For example in FIG. 23, the multiple electrode probe 2042 is placed transverse the nerve 2066, in FIG. 24 the multiple electrode probe 2042 is placed parallel to a portion of the nerve 2066 and FIG. 25 shows the multiple electrode probe 2042 placed across the target nerve 2066 at an angle. As is described in detail above, each of the electrodes 2046-2065 may preferably be selectively connected to a stimulation current source, an ablation energy source, a ground or left unconnected. The electrodes 2046-2062 may be connected manually or switched and activated electronically.

The multiple electrodes of the FIG. 23-25 embodiment of the multiple electrode probe 2042 provides for certain advanced placement and ablation procedures. For example, FIG. 23 illustrates a method for locating and selectively applying energy to a target nerve 2066, which runs substantially transverse the probe at a point along the axial length of the probe 2042. This placement method features the practitioner initially positioning the probe across the target nerve 2066. The electrodes 2046 through 2062 are then activated sequentially with stimulating current, in adjacent active/ground pairs (bipolar mode) or individually with reliance upon an external ground 2064 (mono-polar mode). The practitioner may then observe the response of one or more muscles associated with the target nerve as stimulation current is applied to successive electrodes 2046-2062.

For example, with reference to FIG. 23, stimulation current may be applied between electrodes 2046 and 2048. The practitioner notes that there is no corresponding muscle response. Stimulation current may next be applied between electrodes 2048 and 2050. Again, no muscle response is observed by the practitioner. Sequentially, stimulation current is then applied to successive electrode pairs. When the stimulation current is applied between electrodes 2054 and 2056 there may be a mild muscle response. When the stimulation current is applied between electrodes 2056 and 2058 however, a strong muscle response will be observed. Continuing on, the stimulation is then applied between electrodes 2058 and 2060. Here a greatly reduced muscle response is observed indicating that the nerve is crossing the probe substantially between electrodes 2056 and 2058. Subsequently, ablation energy may be applied between designated electrodes 2056 and 2058 to ablate nerve 2066.

FIG. 24 illustrates a similar nerve location and ablation procedure wherein the nerve 2066 is substantially parallel to and adjacent to the axial length of the probe 2042 adjacent electrodes 2048 through 2056. In this second example the practitioner first applies stimulation current is applied between electrodes 2046 and 2048. A mild muscle response or no muscle response may be observed. When stimulation current is applied between electrodes 2048 and 2050, a strong muscle response is noted by the practitioner.

Sequentially, the stimulation current is then applied between electrodes 2050 and 2052 with similar strong muscle response observed. This sequential stimulation and response process is observed through the activation of electrodes 2056 and 2058 where the muscle response is substantially diminished or not observable. This is an indication that electrodes 2048 through 2056 are all in contact with the nerve 2042. The electrodes 2048 through 2056 may then be switched to the ablation current source activated and sequentially or simultaneously in bi-polar pairs or individually in bi-polar or mono-polar mode to ablate the nerve 2042. The nerve could be ablated along a select length defined by the number of electrodes activated by the practitioner. This method could also be implemented in mono-polar mode whereby stimulation or ablation energy is applied between one or more electrodes 2046 through 2062 and a separate return electrode applied externally on the body.

FIG. 25 illustrates a substantially similar nerve location and ablation procedure wherein the multiple electrode probe 2042 crosses the nerve 2066 diagonally or at an oblique angle to the probe axis. Thus, FIG. 25 illustrates a method for angular positioning of the probe 2042 relative to the nerve 2066. In this example stimulation current applied as described above at electrodes 2052, 2054, and perhaps 2056 would result in a response in the associated muscle. If a larger number of electrodes elicit a muscle response, this is an indication of a broader nerve/probe contact area resulting from a more parallel contact placement of the probe 2042 relative to the nerve 2066. Such a determination of angular placement can be enhanced by fabricating a probe with relatively short distance between adjacent electrodes, relative to the diameter of a nerve of interest. The practitioner may also maneuver the probe to attain a muscle response from more or less electrodes as desired providing the opportunity to ablate a greater or lesser length of the never without axially repositioning the probe.

The above methods of angular probe positioning and sequential stimulation may be combined with the iterative techniques also described above. For example, the stimulation current generator may be set at a relatively high level initially and reduced when the general location of the nerve with respect to certain electrodes is determined.

For example, the stimulation current threshold (to elicit an observable response) between electrodes 2048 and 2050 of FIG. 25 would be higher than the threshold between electrodes 2050 and 2053. This information could be indicated graphically, numerically or audibly to allow the practitioner to reposition the probe for more parallel or more transverse positioning of probe 2042 relative to nerve 2066.

The apparatus and methods described above may be implemented with various features which enhance the safety, ease of use and effectiveness of the system. For example, the probe may be implemented with an ergonomic and functional handle which enhances both operational effectiveness and provides for the implementation of safety features. Individual probes may be carefully managed, preferably with system software to assure that a selected probe functions properly, is sterile and not reused, and that the proper probe is used for each specific treatment procedure. Similarly, safeguards may be included with the system to assure that the operator is certified and trained for the specific treatment protocol selected. Various treatment management methods and specific treatment therapies may be selected for both the best results and for enhanced patient safety. In one embodiment, the treatment, therapeutic, and safety methods may be implemented with and rigorously controlled by software running on a processor associated with the ablation apparatus and system as is described in detail below.

System Management Method

The concurrent goals of patient safety, procedure efficiency and therapeutic success can be advanced through an effective system management method. A system management method such as is described herein may be implemented through computer software and hardware including computer processors and memory operating within or in association with the control console and the probe system described herein. Various interfaces between a practitioner, the control console, and the probe system may be present. In addition the hardware associated with an ablation system, including the probe stimulation current source, ablation current source, and the probe system may be in communication with and provide feedback to the system processor. Alternatively, the steps of the system management method could be implemented manually.

In a software and processor based system embodiment, the techniques described below for managing an electrosurgical probe and system may be implemented as a method, apparatus or article of manufacture using standard programming and/or engineering techniques to produce software, firmware, hardware, or any combination thereof. The term "article of manufacture" as used herein refers to code or logic implemented with or stored upon a medium or device (e.g., magnetic storage medium such as hard disk drives, floppy disks, tape), optical storage (e.g., CD-ROMs, optical disks, etc.), volatile and non-volatile memory devices (e.g., EEPROMs, ROMs, PROMs, RAMs, DRAMs, SRAMs, firmware, programmable logic, etc.). Code in the computer readable medium is accessed and executed by a processor. The code in which implementations are made may further be accessible through a transmission media or from a file server over a network. In such cases, the article of manufacture in which the code is implemented may comprise a transmission media such as network transmission line, wireless transmission media, signals propagating through space, radio waves, infrared, optical signals, etc. Of course, those skilled in the art will recognize that many modifications may be made to this configuration without departing from the scope of the implementations and that the article of manufacture may comprise any information bearing medium known in the art.

Therapeutic Treatment Protocols

As disclosed herein tissue ablation or a nerve block or other minimally invasive electrosurgical procedure may be performed with precisely applied RF energy. A fundamental requirement of the therapeutic RF waveform is to heat and denature human tissue in a small area over a selected time frame, for example, less than 25 seconds. Laboratory experiments indicate this to be a suitable time required to adequately ablate a small motor nerve. Longer or shorter treatment times may be required for other applications. The temperature required to denature the fine structure of the selected tissue, primarily proteins and lipids is approximately 65.degree. C. and above.

To safely achieve appropriate ablation, nerve block or other treatment goals, the RF waveform may be generated and applied to meet the following criteria: 1. The probe temperature will be limited to less than 160.degree. C. in order to prevent excess damage to collateral tissue areas. 2. The probe temperatures will preferably be held to between 90.degree. and 105.degree. C. This range will prevent excessive tissue sticking as well as aid in the growth of an appropriate ablation lesion.

Initial RF power application should bring the temperature of the probe tip to a working therapeutic temperature in controlled manner, causing minimal overshoot. The time frame for the initial warming phase may be between 0.2 to 2.5 seconds.

To achieve the foregoing generalized goals, specific treatment protocols may be developed. In one embodiment of the present invention, the delivery of a specific therapeutic protocol (also described as an "energy bolus") herein is automated. Automation can increase safety and treatment effectiveness since the practitioner may concentrate on probe placement while the system assures the delivery of the selected energy bolus. For example, the system controller 401 may be configured to control the waveform of energy supplied to an electrosurgical probe connected to the system. In particular, the wave shape, waveform modulation or pulse time may be controlled. Also, the total time during which power may be applied and maximum power or voltage limits may be set. In addition, a specific treatment protocol may be actively controlled according to feedback such as the probe temperature, adjacent tissue temperature, tissue impedance or other physical parameters which may be measured during the delivery of treatment energy. Specific energy delivery prescriptions or energy boluses may be developed for specific treatment goals. These energy prescriptions may be stored in memory associated with the controller as a permitted therapeutic protocol. A representative therapeutic energy protocol 3250 is shown in tabular form on FIG. 26.

Figure 27:
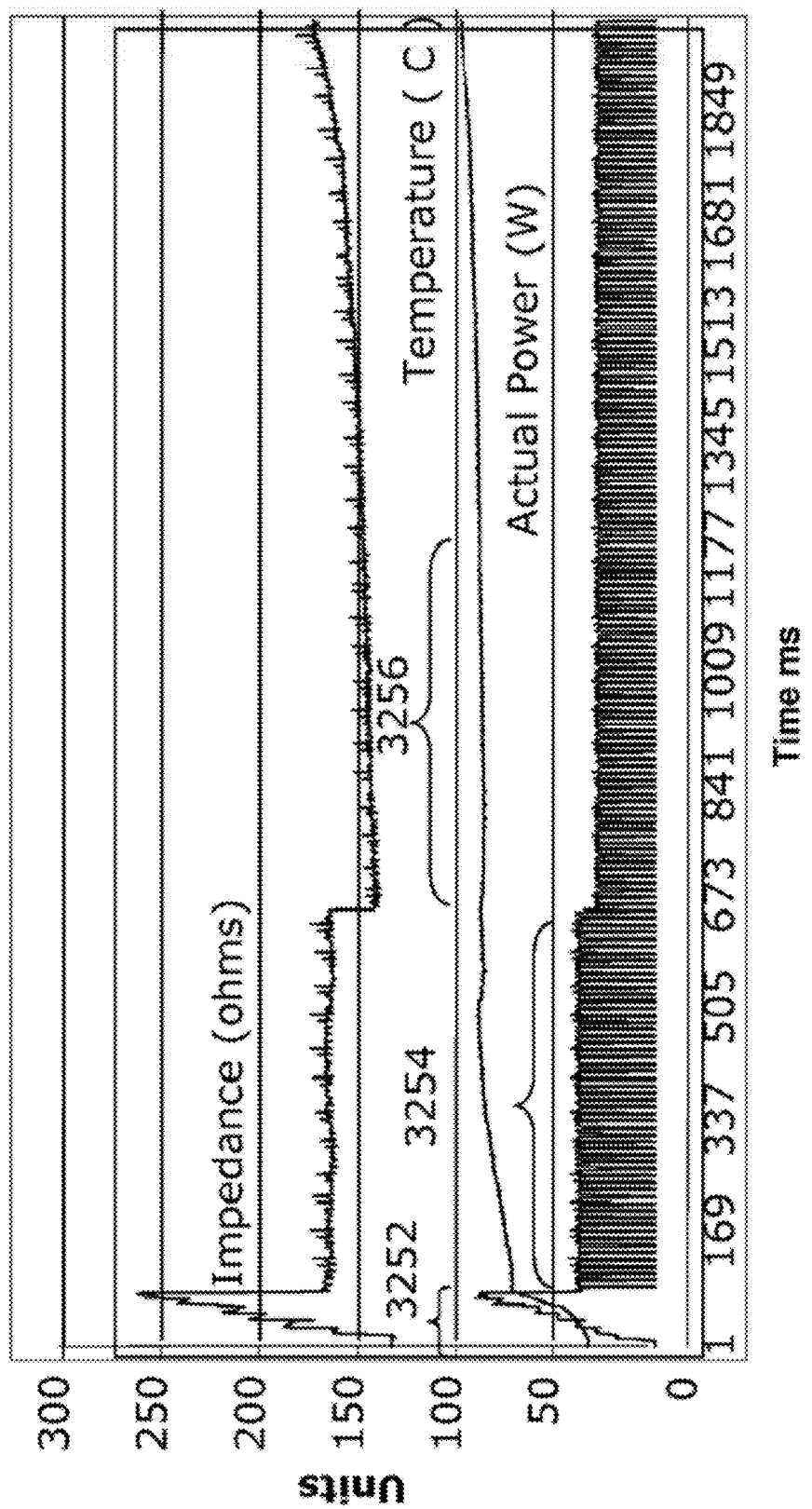
FIG. 27 is a graphic representation of a therapeutic energy protocol consistent with the present invention.

The therapeutic protocol 3250 of FIG. 27 is optimized for the therapeutic ablation of a human nerve having a diameter of approximately 1 millimeter. As shown on FIG. 27, the treatment protocol 3250 is generally designed to rapidly heat tissue during an initial phase 3252. Rapid heating during the initial phase has been shown to minimize perceived pain and reduce muscle stimulation from the subsequent application of pulsed RF energy. A second phase 3254 includes constant power application resulting in a slower ramp to a desired therapeutic tissue/probe temperature. As also shown on FIG. 27, a third phase 3256 includes the maintenance of a constant temperature at reduced power to grow the ablation lesion to a desired size.

Figure 26:
FIG. 26 is a tabular representation of a therapeutic energy protocol consistent with the present invention.

The therapeutic treatment protocol 3250 illustrated on FIGS. 26 and 27 is only one treatment protocol which has been found suitable for the ablation of a small motor nerve. Other treatment protocols may be developed for other or the same therapeutic goals. In all cases, the level of tissue ablation is substantially exponentially related to the product of time and temperature above 40.degree. C. as is well known in the art as the Arrhenius rate. Thermal heat transport through target tissue may be calculated with a finite difference algorithm. Tissue properties may be specified on a 2D mesh and such properties can be arbitrary functions of space and time. Arrhenius rate equations may be solved for the extent of ablation caused by elevated temperatures. In addition, optical and electrical properties which are characteristic of ablated tissue may be measured and determined through histological studies. Thus, various therapeutic protocols such as that illustrated in FIGS. 26 and 27 may be developed and optimized for the controlled achievement of desired therapeutic results. Preferably the therapeutic protocols are automatically delivered to assure that the selected energy bolus is precisely delivered.

The devices and systems described below are provided as examples of details of construction and arrangement of components. The invention includes variations of devices, systems and methods that capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

The invention claimed is:

1. A method of treating a nerve in a tissue region, the method comprising:
   positioning a working end of a device into the tissue region;
   where the device includes a stimulation mode and an energy delivery mode, the stimulation mode comprises at least a first parameter setting that stimulates the nerve at a first distance from the working end, and a second parameter setting that stimulates the nerve at a second distance from the working end, where the first distance is greater than the second distance, and where the device is configured to prevent activation of the energy delivery mode when the stimulation mode is in the first parameter setting;
   activating the device in the stimulation mode at the first parameter setting to observe a stimulation of the nerve;
   repositioning the working end of the device in the tissue region to move the working end closer to the nerve;
   re-activating the device in the stimulation mode at the second parameter setting to observe stimulation of the nerve and confirm repositioning of the working end of the device closer to the nerve; and
   activating the device in the energy delivery mode to create a first treatment zone on the nerve at a pre-determined treatment setting, where activating the device in the energy delivery mode causes the device to reset to the first parameter setting.

2. The method of claim 1, further comprising moving the working end in a direction relative to the nerve to create multiple treatment zones along the nerve.

3. The method of claim 2, where moving the working end of the device in the direction relative to the nerve comprises moving the working end of the device in a forward direction distally to a first treatment zone along the nerve such that a muscle associated with the nerve can be stimulated during stimulation of the nerve.

4. The method of claim 1, where positioning the working end of the device and repositioning the working end of the device occurs without removing the device from a puncture site.

5. The method of claim 4, further comprising performing moving the device in a plurality of directions without removing the device from the tissue region to increase an area for observing stimulation of the nerve.

6. The method of claim 1, further comprising injecting an anesthetic at or near the first treatment zone prior to activating the device in the energy delivery mode.

7. The method of claim 1, further comprising reducing a temperature of the surface of the skin above the treatment site prior to delivering energy.

8. The method of claim 1, further comprising the use of an external nerve stimulator to map the nerve anatomy on skin, prior to inserting the device, and using the map as a guide to identify target treatment locations.

9. The method of claim 1, where the first parameter setting comprises a first current setting and the second parameter setting comprises a second current setting, where the second current setting is less than the first current setting.

10. The method of claim 1, where the first parameter setting is fixed.

11. The method of claim 10, where the second parameter setting is adjustable.

12. The method of claim 1, where activating the device in the stimulation mode at the first parameter setting to observe the stimulation of the nerve comprises observing movement of a surface of the tissue region.

13. The method of claim 1, where activating the device in the stimulation mode at the first parameter setting to observe the stimulation of the nerve comprises performing electromyography on at least one muscle associated with the nerve.

14. The method of claim 1, where activating the device in the stimulation mode at the first parameter setting to observe the stimulation of the nerve comprises measuring an electrical impulse in at least one muscle associated with the nerve using a measuring electrode.

15. The method of claim 1, where the pre-determined treatment setting comprises a pre-determined temperature.

16. The method of claim 1, where the device includes a controller configured to power the device between the stimulation mode and the energy delivery mode.

17. The method of claim 1, where the device is capable of being manually overridden to the energy delivery mode when the stimulation mode is in the first parameter setting.

18. A method of treating a nerve in a tissue region, the method comprising:
positioning a device into the tissue region at a first location;
applying energy to the tissue region through the device at the first location using a first setting configured to stimulate the nerve within a first distance from a working end of the device;
observing for stimulation of the nerve;
re-applying energy to the tissue region through the device at a second location using a second setting configured to stimulate the nerve within a second distance from the working end of the device, where the second distance is less than the first distance;
re-assessing whether the nerve is stimulated at the second setting to determine if the second location is closer to the nerve than the first location;
applying therapeutic energy to the nerve to affect the ability of the nerve to transmit a neural signal using the device upon observing stimulation of the nerve using the second setting if the second location is closer to the nerve and monitoring the nerve for a pre-determined treatment setting.

19. The method of 18, wherein the device resets to the first setting after applying energy to the nerve, the method further comprising re-adjusting the device to the second setting and subsequently re-applying energy to the tissue region through the device at a subsequent location using a second setting configured to stimulate the nerve within the second distance from the working end of the device.

20. The method of claim 18, where re-applying energy to the tissue region through the device at the second location comprises moving the device in a direction relative to the nerve to create multiple treatment zones along the nerve.

21. The method of claim 20, where moving the device in the direction relative to the nerve comprises moving the device in a forward direction distally to the first location along the nerve such that a muscle associated with the nerve can be stimulated during stimulation of the nerve.

22. The method of claim 20, where positioning the device at the first location and the second location occurs without removing the device from a puncture site.

23. The method of claim 18, further comprising moving the device in a plurality of directions without removing the device from the tissue region prior to re-applying energy at the second location.

24. The method of claim 18, further comprising injecting an anesthetic at or near the tissue region at the first location site prior to applying energy to the tissue region.

25. The method of claim 18, further comprising reducing a temperature of the surface of the tissue region above the treatment site prior to applying energy to the nerve.

26. The method of claim 18, further comprising using an external nerve stimulator to map the nerve anatomy on the skin, prior to inserting the working end of the device, and using the map as a guide to identify target treatment locations.

27. The method of claim 18, where the first setting comprises a first current setting and the second setting comprises a second current setting, where the second current setting is less than the first current setting.

28. The method of claim 18, where observing stimulation of the nerve comprises observing for movement of a surface of the tissue region.

29. The method of claim 18, where observing stimulation of the nerve comprises performing electromyography on at least one muscle associated with the nerve.

30. The method of claim 18, where observing stimulation of the nerve comprises measuring an electrical impulse in at least one muscle associated with the nerve using a measuring electrode.

* * * * *